(12) United States Patent
Woo et al.

(10) Patent No.: US 9,637,768 B2
(45) Date of Patent: May 2, 2017

(54) METHOD FOR PREPARING SIALIC ACID DERIVATIVE

(71) Applicant: GENECHEM INC., Daejeon (KR)

(72) Inventors: Jin Suk Woo, Daejeon (KR); Byung-Gee Kim, Seoul (KR); Dae Hee Kim, Daejeon (KR); Yun Hee Choi, Seoul (KR); Jae-Kyung Song, Chungcheongnam-do (KR); Sun Youp Kang, Daejeon (KR); Won Min Seo, Daejeon (KR); Ji Young Yang, Daejeon (KR); Sang Mi Lee, Daejeon (KR)

(73) Assignee: GENECHEM INC., Daejeon (KR)

( * ) Notice: Subject to any disclaimer, the term of this patent is extended or adjusted under 35 U.S.C. 154(b) by 0 days.

(21) Appl. No.: 14/894,757

(22) PCT Filed: May 30, 2014

(86) PCT No.: PCT/KR2014/004823
§ 371 (c)(1),
(2) Date: Nov. 30, 2015

(87) PCT Pub. No.: WO2014/193183
PCT Pub. Date: Dec. 4, 2014

(65) Prior Publication Data
US 2016/0130621 A1    May 12, 2016

(30) Foreign Application Priority Data
May 31, 2013 (KR) .......... 10-2013-0062733

(51) Int. Cl.
| | | |
|---|---|---|
| C12P 19/18 | (2006.01) | |
| C12P 19/26 | (2006.01) | |
| C12P 19/60 | (2006.01) | |
| C07K 9/00 | (2006.01) | |
| C12P 19/12 | (2006.01) | |
| C12P 21/00 | (2006.01) | |
| C12P 19/44 | (2006.01) | |

(52) U.S. Cl.
CPC .............. *C12P 19/18* (2013.01); *C07K 9/008* (2013.01); *C12P 19/12* (2013.01); *C12P 19/26* (2013.01); *C12P 19/44* (2013.01); *C12P 19/60* (2013.01); *C12P 21/005* (2013.01); *Y02P 20/582* (2015.11)

(58) Field of Classification Search
None
See application file for complete search history.

(56) References Cited

U.S. PATENT DOCUMENTS

| 5,071,750 A | 12/1991 | Kragl et al. |
| 5,665,574 A | 9/1997 | Tsukada et al. |
| 5,994,105 A | 11/1999 | Tsukada et al. |
| 6,846,656 B1 | 1/2005 | Koizumi et al. |
| 2003/0109007 A1 | 6/2003 | Koizumi et al. |
| 2005/0260718 A1 | 11/2005 | Noguchi et al. |
| 2011/0207179 A1 | 8/2011 | Noguchi et al. |

FOREIGN PATENT DOCUMENTS

| JP | 3180190 A | 8/1991 |
| JP | 5211884 A | 8/1993 |
| JP | 104961 A | 1/1998 |
| JP | 2001136982 A | 5/2001 |
| KR | 1020060010706 A | 2/2006 |
| KR | 1020080055588 A | 6/2008 |
| KR | 100914525 B1 | 9/2009 |
| WO | 9526399 A1 | 10/1995 |
| WO | 2008072861 A1 | 6/2008 |

OTHER PUBLICATIONS

Sugiarto, G., et al., "Decreasing the sialidase activity of multifunctional Pasteurella multocida 2-3-sialyltransferase 1 (PmST1) by site-directed mutagenesis", "Molecular BioSystems", 2011, pp. 3021-3027, vol. 7.
Chappell, M., et al. "Enzyme-Catalyzed Synthesis of Oligosaccharides That Contain Functionalized Sialic Acids", ,"J. Am. Chem. Soc.", Apr. 9, 1997, pp. 3393-3394, vol. 119.
Han, N., et al., "Biotechnological production of human milk oligosaccharides", "Biotechnology Advances", Nov.-Dec. 2012, pp. 1268-1278, vol. 30.
Kim, M., et al., "Enzymes in carbohydrate synthesis: N-acetylneuraminic acid aldolase catalyzed reactions and preparation of N-acetyl-2-deoxy-D-neuraminic acid derivatives", "J. Am. Chem. Soc.", Sep. 1988, pp. 6481-6486, vol. 110.
Simon, E., et al., "Synthesis of CMP-NeuAc from N-acetylglucosamine: generation of CTP from CMP using adenylate kinase", "J. Am. Chem. Soc.", Oct. 1988, pp. 7159-7163, vol. 110.
Blayer, S., et al., "Alkaline biocatalysis for the direct synthesis of N-acetyl-D-neuraminic acid (Neu5Ac) from N-acetyl-D-glucosamine (GlcNAc)", "Biotechnology and Bioengineering", Jan. 1999, pp. 131-136, vol. 66, No. 2.
Kim, D., Doctoral Dissertation, "Glycosylation Including Sialydation of Small Molecule by Addition of Necleotide-Sugars", Department of Life Science and Biochemical Engineering, Biotechnology Major, Graduate School, Sun Moon University, Republic of Korea, Jun. 2011, pp. 1-173.

(Continued)

*Primary Examiner* — Anand Desai
(74) *Attorney, Agent, or Firm* — Hultquist, PLLC; Steven J. Hultquist

(57) ABSTRACT

The present invention relates to a method for preparing a sialic acid derivative characterized by performing both of a process for preparing CMP-N-acetylneuraminic acid using N-acetyl-D-glucosamine and a process for preparing the sialic acid (neuraminic acid) derivative that combines a sialic acid with a galactose derivative or a lactose derivative, together, in one reactor. According to the method for preparing a sialic acid derivative of the present invention, expensive cytidine 5'-monophosphate (CMP) is capable of being recycled in a reactor, such that an amount of the CMP introduced into the reactor may be reduced, and the sialic acid derivative is capable of being prepared at a significantly high efficiency by using cheap N-acetyl-D-glucosamine, and pyruvate as substrates.

6 Claims, 18 Drawing Sheets

(56) References Cited

OTHER PUBLICATIONS

Mahmoudian, M., et al., "An efficient process for production of N-acetylneuraminic acid using N-acetylneuraminic acid aldolase", "Enzyme and Microbial Technology", Apr. 1997, pp. 393-400, vol. 20.

Maru, I., et al., "Simple and Large-Scale Production of N-acetylneuraminic Acid from N-acetyl-d-glucosamine and Pyruvate Using N-acyl-d-glucosamine 2-epimerase and N-acetylneuraminate lyase", "Carbohydrate Research", 1998, pp. 575-578, vol. 306.

Tabata, K., et al. "Production of N-acetyl-D-neuraminic Acid by Coupling Bacteria Expressing N-acetyl-D-glucosamine 2-epimerase and N-acetyl-D-neuraminic Acid Synthetase", "Enzyme and Microbial Technology", 2002, pp. 327-333, vol. 30.

Note: For the non-patent Literature citations that no month of publicaiton is indicated, the year of publication is more than 1 year prior to the effective filing date of the present application.

A

B

HPLC

In mass analysis of FK506-M32-LS-SL sodium salt molecular ions were detected in a form of [M+Na]+ (m/z 1564.3)

1564.3

In mass analysis of FK506-M32-LA-SL, molecular ions were detected in a form of [M-2H]$^{2-}$ (m/z 1616.8)

1616.8

In mass analysis of DTX-M2'-LS-Lac, molecular ions
were detected in a form of [M+Na]⁺ (m/z 1255.3)

In mass analysis of DTX-M2'-LS-SL sodium salt, molecular ions
were detected in a form of [M+Na]⁺ (m/z 1568.0)

In mass analysis of Sial-gal-vancomycin, molecular ions were detected in a form of $[M+4H]^+$ (m/z 1905.4)

SEQUENCE LISTING

<160> NUMBER OF SEQ ID NOS: 39

<210> SEQ ID NO 1
<211> LENGTH: 391
<212> TYPE: PRT
<213> ORGANISM: Pasteurella multosida

<400> SEQUENCE: 1

Met Lys Thr Ile Thr Leu Tyr Leu Asp Pro Ala Ser Leu Pro Ala Leu
1               5                   10                  15

Asn Gln Leu Met Asp Phe Thr Gln Asn Asn Glu Asp Lys Thr His Pro
            20                  25                  30

Arg Ile Phe Gly Leu Ser Arg Phe Lys Ile Pro Asp Asn Ile Ile Thr
        35                  40                  45

Gln Tyr Gln Asn Ile His Phe Val Glu Leu Lys Asp Asn Arg Pro Thr
    50                  55                  60

Glu Ala Leu Phe Thr Ile Leu Asp Gln Tyr Pro Gly Asn Ile Glu Leu
65                  70                  75                  80

Asn Ile His Leu Asn Ile Ala His Ser Val Gln Leu Ile Arg Pro Ile
                85                  90                  95

Leu Ala Tyr Arg Phe Lys His Leu Asp Arg Val Ser Ile Gln Gln Leu
            100                 105                 110

Asn Leu Tyr Asp Asp Gly Ser Met Glu Tyr Val Asp Leu Glu Lys Glu
        115                 120                 125

Glu Asn Lys Asp Ile Ser Ala Glu Ile Lys Gln Ala Glu Lys Gln Leu
    130                 135                 140

Ser His Tyr Leu Leu Thr Gly Lys Ile Lys Phe Asp Asn Pro Thr Ile
145                 150                 155                 160

Ala Arg Tyr Val Trp Gln Ser Ala Phe Pro Val Lys Tyr His Phe Leu
                165                 170                 175

Ser Thr Asp Tyr Phe Glu Lys Ala Glu Phe Leu Gln Pro Leu Lys Glu
            180                 185                 190

-continued

```
Tyr Leu Ala Glu Asn Tyr Gln Lys Met Asp Trp Thr Ala Tyr Gln Gln
            195                 200                 205

Leu Thr Pro Glu Gln Gln Ala Phe Tyr Leu Thr Leu Val Gly Phe Asn
210                 215                 220

Asp Glu Val Lys Gln Ser Leu Glu Val Gln Gln Ala Lys Phe Ile Phe
225                 230                 235                 240

Thr Gly Thr Thr Thr Trp Gly Asn Thr Asp Val Arg Glu Tyr Tyr
            245                 250                 255

Ala Gln Gln Gln Leu Asn Leu Asn His Phe Thr Gln Ala Glu Gly
            260                 265                 270

Asp Leu Phe Ile Gly Asp His Tyr Lys Ile Tyr Phe Lys Gly His Pro
            275                 280                 285

Arg Gly Gly Glu Ile Asn Asp Tyr Ile Leu Asn Asn Ala Lys Asn Ile
290                 295                 300

Thr Asn Ile Pro Ala Asn Ile Ser Phe Glu Val Leu Met Met Thr Gly
305                 310                 315                 320

Leu Leu Pro Asp Lys Val Gly Val Ala Ser Ser Leu Tyr Phe Ser
            325                 330                 335

Leu Pro Lys Glu Lys Ile Ser His Ile Ile Phe Thr Ser Asn Lys Gln
            340                 345                 350

Val Lys Ser Lys Glu Asp Ala Leu Asn Asn Pro Tyr Val Lys Val Met
            355                 360                 365

Arg Arg Leu Gly Ile Ile Asp Glu Ser Gln Val Ile Phe Trp Asp Ser
            370                 375                 380

Leu Lys Gln Leu Gly Gly Gly
385                 390

<210> SEQ ID NO 2
<211> LENGTH: 391
<212> TYPE: PRT
<213> ORGANISM: Artificial Sequence
<220> FEATURE:
<223> OTHER INFORMATION: R313N

<400> SEQUENCE: 2

Met Lys Thr Ile Thr Leu Tyr Leu Asp Pro Ala Ser Leu Pro Ala Leu
1               5                   10                  15

Asn Gln Leu Met Asp Phe Thr Gln Asn Asn Glu Asp Lys Thr His Pro
            20                  25                  30

Arg Ile Phe Gly Leu Ser Arg Phe Lys Ile Pro Asp Asn Ile Ile Thr
        35                  40                  45

Gln Tyr Gln Asn Ile His Phe Val Glu Leu Lys Asp Asn Arg Pro Thr
    50                  55                  60

Glu Ala Leu Phe Thr Ile Leu Asp Gln Tyr Pro Gly Asn Ile Glu Leu
65                  70                  75                  80

Asn Ile His Leu Asn Ile Ala His Ser Val Gln Leu Ile Arg Pro Ile
                85                  90                  95

Leu Ala Tyr Arg Phe Lys His Leu Asp Arg Val Ser Ile Gln Gln Leu
            100                 105                 110

Asn Leu Tyr Asp Asp Gly Ser Met Glu Tyr Val Asp Leu Glu Lys Glu
        115                 120                 125

Glu Asn Lys Asp Ile Ser Ala Glu Ile Lys Gln Ala Glu Lys Gln Leu
    130                 135                 140

Ser His Tyr Leu Leu Thr Gly Lys Ile Lys Phe Asp Asn Pro Thr Ile
145                 150                 155                 160
```

```
Ala Arg Tyr Val Trp Gln Ser Ala Phe Pro Val Lys Tyr His Phe Leu
            165                 170                 175

Ser Thr Asp Tyr Phe Glu Lys Ala Glu Phe Leu Gln Pro Leu Lys Glu
        180                 185                 190

Tyr Leu Ala Glu Asn Tyr Gln Lys Met Asp Trp Thr Ala Tyr Gln Gln
    195                 200                 205

Leu Thr Pro Glu Gln Gln Ala Phe Tyr Leu Thr Leu Gly Phe Asn
210                 215                 220

Asp Glu Val Lys Gln Ser Leu Glu Val Gln Ala Lys Phe Ile Phe
225                 230                 235                 240

Thr Gly Thr Thr Thr Trp Glu Gly Asn Thr Asp Val Arg Glu Tyr Tyr
            245                 250                 255

Ala Gln Gln Gln Leu Asn Leu Leu Asn His Phe Thr Gln Ala Glu Gly
        260                 265                 270

Asp Leu Phe Ile Gly Asp His Tyr Lys Ile Tyr Phe Lys Gly His Pro
    275                 280                 285

Asn Gly Gly Glu Ile Asn Asp Tyr Ile Leu Asn Asn Ala Lys Asn Ile
        290                 295                 300

Thr Asn Ile Pro Ala Asn Ile Ser Phe Glu Val Leu Met Met Thr Gly
305                 310                 315                 320

Leu Leu Pro Asp Lys Val Gly Val Ala Ser Ser Leu Tyr Phe Ser
            325                 330                 335

Leu Pro Lys Glu Lys Ile Ser His Ile Ile Phe Thr Ser Asn Lys Gln
        340                 345                 350

Val Lys Ser Lys Glu Asp Ala Leu Asn Asn Pro Tyr Val Lys Val Met
    355                 360                 365

Arg Arg Leu Gly Ile Ile Asp Glu Ser Gln Val Ile Phe Trp Asp Ser
370                 375                 380

Leu Lys Gln Leu Gly Gly Gly
385                 390

<210> SEQ ID NO 3
<211> LENGTH: 391
<212> TYPE: PRT
<213> ORGANISM: Artificial Sequence
<220> FEATURE:
<223> OTHER INFORMATION: R313H

<400> SEQUENCE: 3

Met Lys Thr Ile Thr Leu Tyr Leu Asp Pro Ala Ser Leu Pro Ala Leu
1               5                   10                  15

Asn Gln Leu Met Asp Phe Thr Gln Asn Asn Glu Asp Lys Thr His Pro
            20                  25                  30

Arg Ile Phe Gly Leu Ser Arg Phe Lys Ile Pro Asp Asn Ile Ile Thr
        35                  40                  45

Gln Tyr Gln Asn Ile His Phe Val Glu Leu Lys Asp Asn Arg Pro Thr
    50                  55                  60

Glu Ala Leu Phe Thr Ile Leu Asp Gln Tyr Pro Gly Asn Ile Glu Leu
65                  70                  75                  80

Asn Ile His Leu Asn Ile Ala His Ser Val Gln Leu Ile Arg Pro Ile
            85                  90                  95

Leu Ala Tyr Arg Phe Lys His Leu Asp Arg Val Ser Ile Gln Gln Leu
        100                 105                 110

Asn Leu Tyr Asp Asp Gly Ser Met Glu Tyr Val Asp Leu Glu Lys Glu
    115                 120                 125
```

Glu Asn Lys Asp Ile Ser Ala Glu Ile Lys Gln Ala Glu Lys Gln Leu
130                 135                 140

Ser His Tyr Leu Leu Thr Gly Lys Ile Lys Phe Asp Asn Pro Thr Ile
145                 150                 155                 160

Ala Arg Tyr Val Trp Gln Ser Ala Phe Pro Val Lys Tyr His Phe Leu
                165                 170                 175

Ser Thr Asp Tyr Phe Glu Lys Ala Glu Phe Leu Gln Pro Leu Lys Glu
            180                 185                 190

Tyr Leu Ala Glu Asn Tyr Gln Lys Met Asp Trp Thr Ala Tyr Gln Gln
        195                 200                 205

Leu Thr Pro Glu Gln Gln Ala Phe Tyr Leu Thr Leu Val Gly Phe Asn
210                 215                 220

Asp Glu Val Lys Gln Ser Leu Glu Val Gln Gln Ala Lys Phe Ile Phe
225                 230                 235                 240

Thr Gly Thr Thr Thr Trp Glu Gly Asn Thr Asp Val Arg Glu Tyr Tyr
                245                 250                 255

Ala Gln Gln Gln Leu Asn Leu Leu Asn His Phe Thr Gln Ala Glu Gly
            260                 265                 270

Asp Leu Phe Ile Gly Asp His Tyr Lys Ile Tyr Phe Lys Gly His Pro
        275                 280                 285

His Gly Gly Glu Ile Asn Asp Tyr Ile Leu Asn Asn Ala Lys Asn Ile
290                 295                 300

Thr Asn Ile Pro Ala Asn Ile Ser Phe Glu Val Leu Met Met Thr Gly
305                 310                 315                 320

Leu Leu Pro Asp Lys Val Gly Val Ala Ser Ser Leu Tyr Phe Ser
                325                 330                 335

Leu Pro Lys Glu Lys Ile Ser His Ile Ile Phe Thr Ser Asn Lys Gln
            340                 345                 350

Val Lys Ser Lys Glu Asp Ala Leu Asn Asn Pro Tyr Val Lys Val Met
        355                 360                 365

Arg Arg Leu Gly Ile Ile Asp Glu Ser Gln Val Ile Phe Trp Asp Ser
370                 375                 380

Leu Lys Gln Leu Gly Gly Gly
385                 390

<210> SEQ ID NO 4
<211> LENGTH: 391
<212> TYPE: PRT
<213> ORGANISM: Artificial Sequence
<220> FEATURE:
<223> OTHER INFORMATION: T265S

<400> SEQUENCE: 4

Met Lys Thr Ile Thr Leu Tyr Leu Asp Pro Ala Ser Leu Pro Ala Leu
1               5                   10                  15

Asn Gln Leu Met Asp Phe Thr Gln Asn Asn Glu Asp Lys Thr His Pro
            20                  25                  30

Arg Ile Phe Gly Leu Ser Arg Phe Lys Ile Pro Asp Asn Ile Ile Thr
        35                  40                  45

Gln Tyr Gln Asn Ile His Phe Val Glu Leu Lys Asp Asn Arg Pro Thr
    50                  55                  60

Glu Ala Leu Phe Thr Ile Leu Asp Gln Tyr Pro Gly Asn Ile Glu Leu
65                  70                  75                  80

Asn Ile His Leu Asn Ile Ala His Ser Val Gln Leu Ile Arg Pro Ile
                85                  90                  95

```
Leu Ala Tyr Arg Phe Lys His Leu Asp Arg Val Ser Ile Gln Gln Leu
                100                 105                 110

Asn Leu Tyr Asp Asp Gly Ser Met Glu Tyr Val Asp Leu Glu Lys Glu
            115                 120                 125

Glu Asn Lys Asp Ile Ser Ala Glu Ile Lys Gln Ala Glu Lys Gln Leu
        130                 135                 140

Ser His Tyr Leu Leu Thr Gly Lys Ile Lys Phe Asp Asn Pro Thr Ile
145                 150                 155                 160

Ala Arg Tyr Val Trp Gln Ser Ala Phe Pro Val Lys Tyr His Phe Leu
                165                 170                 175

Ser Thr Asp Tyr Phe Glu Lys Ala Glu Phe Leu Gln Pro Leu Lys Glu
            180                 185                 190

Tyr Leu Ala Glu Asn Tyr Gln Lys Met Asp Trp Thr Ala Tyr Gln Gln
        195                 200                 205

Leu Thr Pro Glu Gln Gln Ala Phe Tyr Leu Thr Leu Val Gly Phe Asn
210                 215                 220

Asp Glu Val Lys Gln Ser Leu Glu Val Gln Gln Ala Lys Phe Ile Phe
225                 230                 235                 240

Ser Gly Thr Thr Thr Trp Glu Gly Asn Thr Asp Val Arg Glu Tyr Tyr
                245                 250                 255

Ala Gln Gln Gln Leu Asn Leu Leu Asn His Phe Thr Gln Ala Glu Gly
            260                 265                 270

Asp Leu Phe Ile Gly Asp His Tyr Lys Ile Tyr Phe Lys Gly His Pro
        275                 280                 285

Arg Gly Gly Glu Ile Asn Asp Tyr Ile Leu Asn Asn Ala Lys Asn Ile
290                 295                 300

Thr Asn Ile Pro Ala Asn Ile Ser Phe Glu Val Leu Met Met Thr Gly
305                 310                 315                 320

Leu Leu Pro Asp Lys Val Gly Val Ala Ser Ser Leu Tyr Phe Ser
                325                 330                 335

Leu Pro Lys Glu Lys Ile Ser His Ile Ile Phe Thr Ser Asn Lys Gln
            340                 345                 350

Val Lys Ser Lys Glu Asp Ala Leu Asn Asn Pro Tyr Val Lys Val Met
        355                 360                 365

Arg Arg Leu Gly Ile Ile Asp Glu Ser Gln Val Ile Phe Trp Asp Ser
370                 375                 380

Leu Lys Gln Leu Gly Gly Gly
385                 390

<210> SEQ ID NO 5
<211> LENGTH: 391
<212> TYPE: PRT
<213> ORGANISM: Artificial Sequence
<220> FEATURE:
<223> OTHER INFORMATION: R313N+T265S

<400> SEQUENCE: 5

Met Lys Thr Ile Thr Leu Tyr Leu Asp Pro Ala Ser Leu Pro Ala Leu
1               5                   10                  15

Asn Gln Leu Met Asp Phe Thr Gln Asn Asn Glu Asp Lys Thr His Pro
            20                  25                  30

Arg Ile Phe Gly Leu Ser Arg Phe Lys Ile Pro Asp Asn Ile Ile Thr
        35                  40                  45

Gln Tyr Gln Asn Ile His Phe Val Glu Leu Lys Asp Asn Arg Pro Thr
50                  55                  60
```

```
Glu Ala Leu Phe Thr Ile Leu Asp Gln Tyr Pro Gly Asn Ile Glu Leu
 65                  70                  75                  80

Asn Ile His Leu Asn Ile Ala His Ser Val Gln Leu Ile Arg Pro Ile
             85                  90                  95

Leu Ala Tyr Arg Phe Lys His Leu Asp Arg Val Ser Ile Gln Gln Leu
            100                 105                 110

Asn Leu Tyr Asp Asp Gly Ser Met Glu Tyr Val Asp Leu Glu Lys Glu
            115                 120                 125

Glu Asn Lys Asp Ile Ser Ala Glu Ile Lys Gln Ala Glu Lys Gln Leu
        130                 135                 140

Ser His Tyr Leu Leu Thr Gly Lys Ile Lys Phe Asp Asn Pro Thr Ile
145                 150                 155                 160

Ala Arg Tyr Val Trp Gln Ser Ala Phe Pro Val Lys Tyr His Phe Leu
                165                 170                 175

Ser Thr Asp Tyr Phe Glu Lys Ala Glu Phe Leu Gln Pro Leu Lys Glu
            180                 185                 190

Tyr Leu Ala Glu Asn Tyr Gln Lys Met Asp Trp Thr Ala Tyr Gln Gln
            195                 200                 205

Leu Thr Pro Glu Gln Gln Ala Phe Tyr Leu Thr Leu Val Gly Phe Asn
210                 215                 220

Asp Glu Val Lys Gln Ser Leu Glu Val Gln Gln Ala Lys Phe Ile Phe
225                 230                 235                 240

Ser Gly Thr Thr Thr Trp Glu Gly Asn Thr Asp Val Arg Glu Tyr Tyr
                245                 250                 255

Ala Gln Gln Gln Leu Asn Leu Leu Asn His Phe Thr Gln Ala Glu Gly
            260                 265                 270

Asp Leu Phe Ile Gly Asp His Tyr Lys Ile Tyr Phe Lys Gly His Pro
            275                 280                 285

Asn Gly Gly Glu Ile Asn Asp Tyr Ile Leu Asn Asn Ala Lys Asn Ile
        290                 295                 300

Thr Asn Ile Pro Ala Asn Ile Ser Phe Glu Val Leu Met Met Thr Gly
305                 310                 315                 320

Leu Leu Pro Asp Lys Val Gly Gly Val Ala Ser Ser Leu Tyr Phe Ser
                325                 330                 335

Leu Pro Lys Glu Lys Ile Ser His Ile Ile Phe Thr Ser Asn Lys Gln
            340                 345                 350

Val Lys Ser Lys Glu Asp Ala Leu Asn Asn Pro Tyr Val Lys Val Met
            355                 360                 365

Arg Arg Leu Gly Ile Ile Asp Glu Ser Gln Val Ile Phe Trp Asp Ser
370                 375                 380

Leu Lys Gln Leu Gly Gly Gly
385                 390

<210> SEQ ID NO 6
<211> LENGTH: 391
<212> TYPE: PRT
<213> ORGANISM: Artificial Sequence
<220> FEATURE:
<223> OTHER INFORMATION: R313H+T265S

<400> SEQUENCE: 6

Met Lys Thr Ile Thr Leu Tyr Leu Asp Pro Ala Ser Leu Pro Ala Leu
  1               5                  10                  15

Asn Gln Leu Met Asp Phe Thr Gln Asn Asn Glu Asp Lys Thr His Pro
             20                  25                  30
```

```
Arg Ile Phe Gly Leu Ser Arg Phe Lys Ile Pro Asp Asn Ile Ile Thr
         35                  40                  45
Gln Tyr Gln Asn Ile His Phe Val Glu Leu Lys Asp Asn Arg Pro Thr
 50                  55                  60
Glu Ala Leu Phe Thr Ile Leu Asp Gln Tyr Pro Gly Asn Ile Glu Leu
 65                  70                  75                  80
Asn Ile His Leu Asn Ile Ala His Ser Val Gln Leu Ile Arg Pro Ile
                 85                  90                  95
Leu Ala Tyr Arg Phe Lys His Leu Asp Arg Val Ser Ile Gln Gln Leu
            100                 105                 110
Asn Leu Tyr Asp Asp Gly Ser Met Glu Tyr Val Asp Leu Glu Lys Glu
        115                 120                 125
Glu Asn Lys Asp Ile Ser Ala Glu Ile Lys Gln Ala Glu Lys Gln Leu
130                 135                 140
Ser His Tyr Leu Leu Thr Gly Lys Ile Lys Phe Asp Asn Pro Thr Ile
145                 150                 155                 160
Ala Arg Tyr Val Trp Gln Ser Ala Phe Pro Val Lys Tyr His Phe Leu
                165                 170                 175
Ser Thr Asp Tyr Phe Glu Lys Ala Glu Phe Leu Gln Pro Leu Lys Glu
            180                 185                 190
Tyr Leu Ala Glu Asn Tyr Gln Lys Met Asp Trp Thr Ala Tyr Gln Gln
        195                 200                 205
Leu Thr Pro Glu Gln Gln Ala Phe Tyr Leu Thr Leu Val Gly Phe Asn
210                 215                 220
Asp Glu Val Lys Gln Ser Leu Glu Val Gln Gln Ala Lys Phe Ile Phe
225                 230                 235                 240
Ser Gly Thr Thr Thr Trp Glu Gly Asn Thr Asp Val Arg Glu Tyr Tyr
                245                 250                 255
Ala Gln Gln Gln Leu Asn Leu Asn His Phe Thr Gln Ala Glu Gly
            260                 265                 270
Asp Leu Phe Ile Gly Asp His Tyr Lys Ile Tyr Phe Lys Gly His Pro
        275                 280                 285
His Gly Gly Glu Ile Asn Asp Tyr Ile Leu Asn Asn Ala Lys Asn Ile
290                 295                 300
Thr Asn Ile Pro Ala Asn Ile Ser Phe Glu Val Leu Met Met Thr Gly
305                 310                 315                 320
Leu Leu Pro Asp Lys Val Gly Val Ala Ser Ser Leu Tyr Phe Ser
                325                 330                 335
Leu Pro Lys Glu Lys Ile Ser His Ile Phe Thr Ser Asn Lys Gln
            340                 345                 350
Val Lys Ser Lys Glu Asp Ala Leu Asn Asn Pro Tyr Val Lys Val Met
        355                 360                 365
Arg Arg Leu Gly Ile Ile Asp Glu Ser Gln Val Ile Phe Trp Asp Ser
370                 375                 380
Leu Lys Gln Leu Gly Gly Gly
385                 390

<210> SEQ ID NO 7
<211> LENGTH: 1173
<212> TYPE: DNA
<213> ORGANISM: Pasteurella multosida

<400> SEQUENCE: 7
atgaaaacaa tcacgctgta tttagatcct gcctccttac cggcattaaa tcagctgatg    60
```

```
gactttacgc aaaataatga agataaaaca catccacgta ttttttggtct ttctcgcttt      120 aaaatccctg acaacattat tacacagtat caaaatatcc atttcgtcga actcaaagat      180
aatcgtccca ctgaagcact ttttacgatt ttagatcaat accctggtaa cattgagtta      240
aatatacact taaatattgc tcattccgtt caattaattc gtccgatttt ggcatatcgt      300
tttaaacatt tagatcgtgt atcaattcag cagttaaatc tttatgacga tggctcaatg      360
gaatatgttg atttagaaaa agaagaaaat aaagatattt ccgcagaaat taagcaagca      420
gaaaaacaac tttctcacta tttgcttact ggcaaaataa aatttgataa cccaactatt      480
gctcgttatg tctggcaatc cgcgttccca gtaaaatatc attttttaag tacagactat      540
tttgaaaaag ccgaattttt acaaccacta aaagaatatt tagcagaaaa ttatcaaaaa      600
atggactgga ctgcttacca acagctgact ccagaacagc aagcattcta cttaacattg      660
gtaggcttca atgacgaagt caagcagtcg ctagaagtgc aacaagctaa atttatcttt      720
accggcacga caacttggga aggaaatacc gatgtgcgag aatactacgc acagcaacaa      780
cttaatttac ttaatcactt tacccaagct gagggcgatt tatttattgg tgatcattat      840
aaaatctact ttaaagggca tcctagaggt ggtgaaatta atgactacat tctgaacaat      900
gctaaaaata tcaccaatat ccctgccaat atttccttttg aagtattgat gatgacaggc      960
ttattacctg ataaagtggg tggtgttgca agttcactgt atttctcctt accaaaagaa     1020
aaaattagcc atattttttt cacatcgaat aaacaagtga aaagcaaaga agatgcgcta     1080
aataatccgt atgttaaggt catgcgtcgt ttaggtataa ttgacgaatc acaagtcatc     1140
ttttgggaca gtttaaaaca gttgggtgga ggt                                 1173
```

<210> SEQ ID NO 8
<211> LENGTH: 1173
<212> TYPE: DNA
<213> ORGANISM: Artificial Sequence
<220> FEATURE:
<223> OTHER INFORMATION: R313N

<400> SEQUENCE: 8

```
atgaaaacaa tcacgctgta tttagatcct gcctccttac cggcattaaa tcagctgatg       60
gactttacgc aaaataatga agataaaaca catccacgta ttttttggtct ttctcgcttt      120 aaaatccctg acaacattat tacacagtat caaaatatcc atttcgtcga actcaaagat      180
aatcgtccca ctgaagcact ttttacgatt ttagatcaat accctggtaa cattgagtta      240
aatatacact taaatattgc tcattccgtt caattaattc gtccgatttt ggcatatcgt      300
tttaaacatt tagatcgtgt atcaattcag cagttaaatc tttatgacga tggctcaatg      360
gaatatgttg atttagaaaa agaagaaaat aaagatattt ccgcagaaat taagcaagca      420
gaaaaacaac tttctcacta tttgcttact ggcaaaataa aatttgataa cccaactatt      480
gctcgttatg tctggcaatc cgcgttccca gtaaaatatc attttttaag tacagactat      540
tttgaaaaag ccgaattttt acaaccacta aaagaatatt tagcagaaaa ttatcaaaaa      600
atggactgga ctgcttacca acagctgact ccagaacagc aagcattcta cttaacattg      660
gtaggcttca atgacgaagt caagcagtcg ctagaagtgc aacaagctaa atttatcttt      720
accggcacga caacttggga aggaaatacc gatgtgcgag aatactacgc acagcaacaa      780
cttaatttac ttaatcactt tacccaagct gagggcgatt tatttattgg tgatcattat      840
aaaatctact ttaaagggca tcctaatggt ggtgaaatta atgactacat tctgaacaat      900
gctaaaaata tcaccaatat ccctgccaat atttccttttg aagtattgat gatgacaggc      960
```

```
ttattacctg ataaagtggg tggtgttgca agttcactgt atttctcctt accaaaagaa    1020
aaaattagcc atattatttt cacatcgaat aaacaagtga aaagcaaaga agatgcgcta    1080
aataatccgt atgttaaggt catgcgtcgt ttaggtataa ttgacgaatc acaagtcatc    1140
ttttgggaca gttaaaaaca gttgggtgga ggt                                 1173

<210> SEQ ID NO 9
<211> LENGTH: 1173
<212> TYPE: DNA
<213> ORGANISM: Artificial Sequence
<220> FEATURE:
<223> OTHER INFORMATION: R313H

<400> SEQUENCE: 9
atgaaaacaa tcacgctgta tttagatcct gcctccttac cggcattaaa tcagctgatg     60
gactttacgc aaaataatga agataaaaca catccacgta ttttttggtct ttctcgcttt    120 aaaatccctg acaacattat tacacagtat caaaatatcc atttcgtcga actcaaagat    180
aatcgtccca ctgaagcact ttttacgatt ttagatcaat accctggtaa cattgagtta    240
aatatacact aaatattgc tcattccgtt caattaattc gtccgatttt ggcatatcgt     300
tttaaacatt tagatcgtgt atcaattcag cagttaaatc tttatgacga tggctcaatg    360
gaatatgttg atttagaaaa agaagaaaat aaagatattt ccgcagaaat taagcaagca    420
gaaaaacaac tttctcacta tttgcttact ggcaaaataa aatttgataa cccaactatt    480
gctcgttatg tctggcaatc cgcgttccca gtaaaatatc attttttaag tacagactat    540
tttgaaaaag ccgaattttt acaaccacta aaagaatatt tagcagaaaa ttatcaaaaa    600
atggactgga ctgcttacca acagctgact ccagaacagc aagcattcta cttaacattg    660
gtaggcttca atgacgaagt caagcagtcg ctagaagtgc aacaagctaa atttatcttt    720
agtggcacga caacttggga aggaaatacc gatgtgcgag atactacgc acagcaacaa    780 cttaatttac ttaatcactt tacccaagct gagggcgatt tatttattgg tgatcattat    840
aaaatctact ttaaagggca tcctcatggt ggtgaaatta atgactacat tctgaacaat    900
gctaaaaata tcaccaatat ccctgccaat atttcctttg aagtattgat gatgacaggc    960
ttattacctg ataaagtggg tggtgttgca agttcactgt atttctcctt accaaaagaa   1020
aaaattagcc atattatttt cacatcgaat aaacaagtga aaagcaaaga agatgcgcta   1080
aataatccgt atgttaaggt catgcgtcgt ttaggtataa ttgacgaatc acaagtcatc   1140
ttttgggaca gttaaaaaca gttgggtgga ggt                                1173

<210> SEQ ID NO 10
<211> LENGTH: 1173
<212> TYPE: DNA
<213> ORGANISM: Artificial Sequence
<220> FEATURE:
<223> OTHER INFORMATION: T265S

<400> SEQUENCE: 10
atgaaaacaa tcacgctgta tttagatcct gcctccttac cggcattaaa tcagctgatg     60
gactttacgc aaaataatga agataaaaca catccacgta ttttttggtct ttctcgcttt    120 aaaatccctg acaacattat tacacagtat caaaatatcc atttcgtcga actcaaagat    180
aatcgtccca ctgaagcact ttttacgatt ttagatcaat accctggtaa cattgagtta    240
aatatacact aaatattgc tcattccgtt caattaattc gtccgatttt ggcatatcgt     300
```

```
tttaaacatt tagatcgtgt atcaattcag cagttaaatc tttatgacga tggctcaatg    360
gaatatgttg atttagaaaa agaagaaaat aaagatattt ccgcagaaat taagcaagca    420
gaaaaacaac tttctcacta tttgcttact ggcaaaataa aatttgataa cccaactatt    480
gctcgttatg tctggcaatc cgcgttccca gtaaaatatc atttttttaag tacagactat   540 tttgaaaaag ccgaattttt acaaccacta aaagaatatt tagcagaaaa ttatcaaaaa    600
atggactgga ctgcttacca acagctgact ccagaacagc aagcattcta cttaacattg    660
gtaggcttca atgacgaagt caagcagtcg ctagaagtgc aacaagctaa atttatcttt    720
agtggcacga caacttggga aggaaatacc gatgtgcgag aatactacgc acagcaacaa    780
cttaatttac ttaatcactt tacccaagct gagggcgatt tatttattgg tgatcattat    840
aaaatctact ttaagggca tcctagaggt ggtgaaatta atgactacat tctgaacaat     900
gctaaaaata tcaccaatat ccctgccaat atttcctttg aagtattgat gatgacaggc    960
ttattacctg ataaagtggg tggtgttgca agttcactgt atttctcctt accaaaagaa    1020
aaaattagcc atattatttt cacatcgaat aaacaagtga aaagcaaaga agatgcgcta   1080
aataatccgt atgttaaggt catgcgtcgt ttaggtataa ttgacgaatc acaagtcatc   1140
ttttgggaca gtttaaaaca gttgggtgga ggt                                1173

<210> SEQ ID NO 11
<211> LENGTH: 1173
<212> TYPE: DNA
<213> ORGANISM: Artificial Sequence
<220> FEATURE:
<223> OTHER INFORMATION: R313N+T265S

<400> SEQUENCE: 11
atgaaaacaa tcacgctgta tttagatcct gcctccttac cggcattaaa tcagctgatg    60
gactttacgc aaaataatga agataaaaca catccacgta ttttttggtct ttctcgcttt   120 aaaatccctg acaacattat tacacagtat caaaatatcc atttcgtcga actcaaagat   180
aatcgtccca ctgaagcact ttttacgatt ttagatcaat accctggtaa cattgagtta   240
aatatacact aaatattgc tcattccgtt caattaattc gtccgatttt ggcatatcgt    300
tttaaacatt tagatcgtgt atcaattcag cagttaaatc tttatgacga tggctcaatg    360
gaatatgttg atttagaaaa agaagaaaat aaagatattt ccgcagaaat taagcaagca    420
gaaaaacaac tttctcacta tttgcttact ggcaaaataa aatttgataa cccaactatt    480
gctcgttatg tctggcaatc cgcgttccca gtaaaatatc atttttttaag tacagactat   540 tttgaaaaag ccgaattttt acaaccacta aaagaatatt tagcagaaaa ttatcaaaaa    600
atggactgga ctgcttacca acagctgact ccagaacagc aagcattcta cttaacattg    660
gtaggcttca atgacgaagt caagcagtcg ctagaagtgc aacaagctaa atttatcttt    720
agcggcacga caacttggga aggaaatacc gatgtgcgag aatactacgc acagcaacaa    780
cttaatttac ttaatcactt tacccaagct gagggcgatt tatttattgg tgatcattat    840
aaaatctact ttaagggca tcctaatggt ggtgaaatta atgactacat tctgaacaat     900
gctaaaaata tcaccaatat ccctgccaat atttcctttg aagtattgat gatgacaggc    960
ttattacctg ataaagtggg tggtgttgca agttcactgt atttctcctt accaaaagaa    1020
aaaattagcc atattatttt cacatcgaat aaacaagtga aaagcaaaga agatgcgcta   1080
aataatccgt atgttaaggt catgcgtcgt ttaggtataa ttgacgaatc acaagtcatc   1140
ttttgggaca gtttaaaaca gttgggtgga ggt                                1173
```

<210> SEQ ID NO 12
<211> LENGTH: 1173
<212> TYPE: DNA
<213> ORGANISM: Artificial Sequence
<220> FEATURE:
<223> OTHER INFORMATION: R313H+T265S

<400> SEQUENCE: 12

| | | | | | |
|---|---|---|---|---|---|
| atgaaaacaa | tcacgctgta | tttagatcct | gcctccttac | cggcattaaa | tcagctgatg | 60 |
| gactttacgc | aaaataatga | agataaaaca | catccacgta | tttttggtct | ttctcgcttt | 120 |
| aaaatccctg | acaacattat | tacacagtat | caaaatatcc | atttcgtcga | actcaaagat | 180 |
| aatcgtccca | ctgaagcact | ttttacgatt | ttagatcaat | accctggtaa | cattgagtta | 240 |
| aatatacact | aaatattgc | tcattccgtt | caattaattc | gtccgatttt | ggcatatcgt | 300 |
| tttaaacatt | tagatcgtgt | atcaattcag | cagttaaatc | tttatgacga | tggctcaatg | 360 |
| gaatatgttg | atttagaaaa | agaagaaaat | aaagatattt | ccgcagaaat | taagcaagca | 420 |
| gaaaaacaac | tttctcacta | tttgcttact | ggcaaaataa | aatttgataa | cccaactatt | 480 |
| gctcgttatg | tctggcaatc | cgcgttccca | gtaaaatatc | atttttttaag | tacagactat | 540 |
| tttgaaaaag | ccgaattttt | acaaccacta | aaagaatatt | tagcagaaaa | ttatcaaaaa | 600 |
| atggactgga | ctgcttacca | acagctgact | ccagaacagc | aagcattcta | cttaacattg | 660 |
| gtaggcttca | atgacgaagt | caagcagtcg | ctagaagtgc | aacaagctaa | atttatcttt | 720 |
| agcggcacga | caacttggga | aggaaatacc | gatgtgcgag | aatactacgc | acagcaacaa | 780 |
| cttaatttac | ttaatcactt | tacccaagct | gagggcgatt | tatttattgg | tgatcattat | 840 |
| aaaatctact | ttaaagggca | tcctcatggt | ggtgaaatta | tgactacat | tctgaacaat | 900 |
| gctaaaaata | tcaccaatat | ccctgccaat | atttccttg | aagtattgat | gatgacaggc | 960 |
| ttattacctg | ataaagtggg | tggtgttgca | agttcactgt | atttctcctt | accaaaagaa | 1020 |
| aaaattagcc | atattatttt | cacatcgaat | aaacaagtga | aagcaaaga | agatgcgcta | 1080 |
| aataatccgt | atgttaaggt | catgcgtcgt | ttaggtataa | ttgacgaatc | acaagtcatc | 1140 |
| ttttgggaca | gtttaaaaca | gttgggtgga | ggt | | | 1173 |

<210> SEQ ID NO 13
<211> LENGTH: 483
<212> TYPE: PRT
<213> ORGANISM: Photobacterium damselae

<400> SEQUENCE: 13

Met Cys Asn Ser Asp Asn Thr Ser Leu Lys Glu Thr Val Ser Ser Asn
1               5                   10                  15

Ser Ala Asp Val Val Glu Thr Glu Thr Tyr Gln Leu Thr Pro Ile Asp
            20                  25                  30

Ala Pro Ser Ser Phe Leu Ser His Ser Trp Glu Gln Thr Cys Gly Thr
        35                  40                  45

Pro Ile Leu Asn Glu Ser Asp Lys Gln Ala Ile Ser Phe Asp Phe Val
    50                  55                  60

Ala Pro Glu Leu Lys Gln Asp Glu Lys Tyr Cys Phe Thr Phe Lys Gly
65                  70                  75                  80

Ile Thr Gly Asp His Arg Tyr Ile Thr Asn Thr Thr Leu Thr Val Val
                85                  90                  95

Ala Pro Thr Leu Glu Val Tyr Ile Asp His Ala Ser Leu Pro Ser Leu
            100                 105                 110

Gln Gln Leu Ile His Ile Ile Gln Ala Lys Asp Glu Tyr Pro Ser Asn
            115                 120                 125

Gln Arg Phe Val Ser Trp Lys Arg Val Thr Val Asp Ala Asp Asn Ala
        130                 135                 140

Asn Lys Leu Asn Ile His Thr Tyr Pro Leu Lys Gly Asn Asn Thr Ser
145                 150                 155                 160

Pro Glu Met Val Ala Ala Ile Asp Glu Tyr Ala Gln Ser Lys Asn Arg
                165                 170                 175

Leu Asn Ile Glu Phe Tyr Thr Asn Thr Ala His Val Phe Asn Asn Leu
            180                 185                 190

Pro Pro Ile Ile Gln Pro Leu Tyr Asn Asn Glu Lys Val Lys Ile Ser
            195                 200                 205

His Ile Ser Leu Tyr Asp Asp Gly Ser Ser Tyr Val Ser Leu Tyr
        210                 215                 220

Gln Trp Lys Asp Thr Pro Asn Lys Ile Glu Thr Leu Glu Gly Glu Val
225                 230                 235                 240

Ser Leu Leu Ala Asn Tyr Leu Ala Gly Thr Ser Pro Asp Ala Pro Lys
                245                 250                 255

Gly Met Gly Asn Arg Tyr Asn Trp His Lys Leu Tyr Asp Thr Asp Tyr
            260                 265                 270

Tyr Phe Leu Arg Glu Asp Tyr Leu Asp Val Glu Ala Asn Leu His Asp
        275                 280                 285

Leu Arg Asp Tyr Leu Gly Ser Ser Ala Lys Gln Met Pro Trp Asp Glu
        290                 295                 300

Phe Ala Lys Leu Ser Asp Ser Gln Gln Thr Leu Phe Leu Asp Ile Val
305                 310                 315                 320

Gly Phe Asp Lys Glu Gln Leu Gln Gln Gln Tyr Ser Gln Ser Pro Leu
                325                 330                 335

Pro Asn Phe Ile Phe Thr Gly Thr Thr Thr Trp Ala Gly Gly Glu Thr
            340                 345                 350

Lys Glu Tyr Tyr Ala Gln Gln Gln Val Asn Val Ile Asn Asn Ala Ile
        355                 360                 365

Asn Glu Thr Ser Pro Tyr Tyr Leu Gly Lys Asp Tyr Asp Leu Phe Phe
        370                 375                 380

Lys Gly His Pro Ala Gly Gly Val Ile Asn Asp Ile Ile Leu Gly Ser
385                 390                 395                 400

Phe Pro Asp Met Ile Asn Ile Pro Ala Lys Ile Ser Phe Glu Val Leu
                405                 410                 415

Met Met Thr Asp Met Leu Pro Asp Thr Val Ala Gly Ile Ala Ser Ser
            420                 425                 430

Leu Tyr Phe Thr Ile Pro Ala Asp Lys Val Asn Phe Ile Val Phe Thr
        435                 440                 445

Ser Ser Asp Thr Ile Thr Asp Arg Glu Glu Ala Leu Lys Ser Pro Leu
        450                 455                 460

Val Gln Val Met Leu Thr Leu Gly Ile Val Lys Glu Lys Asp Val Leu
465                 470                 475                 480

Phe Trp Ala

<210> SEQ ID NO 14
<211> LENGTH: 483
<212> TYPE: PRT
<213> ORGANISM: Artificial Sequence
<220> FEATURE:
<223> OTHER INFORMATION: I411T

<400> SEQUENCE: 14

```
Met Cys Asn Ser Asp Asn Thr Ser Leu Lys Glu Thr Val Ser Ser Asn
1               5                   10                  15

Ser Ala Asp Val Val Glu Thr Glu Thr Tyr Gln Leu Thr Pro Ile Asp
            20                  25                  30

Ala Pro Ser Ser Phe Leu Ser His Ser Trp Glu Gln Thr Cys Gly Thr
        35                  40                  45

Pro Ile Leu Asn Glu Ser Asp Lys Gln Ala Ile Ser Phe Asp Phe Val
    50                  55                  60

Ala Pro Glu Leu Lys Gln Asp Glu Lys Tyr Cys Phe Thr Phe Lys Gly
65                  70                  75                  80

Ile Thr Gly Asp His Arg Tyr Ile Thr Asn Thr Thr Leu Thr Val Val
                85                  90                  95

Ala Pro Thr Leu Glu Val Tyr Ile Asp His Ala Ser Leu Pro Ser Leu
            100                 105                 110

Gln Gln Leu Ile His Ile Ile Gln Ala Lys Asp Glu Tyr Pro Ser Asn
        115                 120                 125

Gln Arg Phe Val Ser Trp Lys Arg Val Thr Val Asp Ala Asp Asn Ala
    130                 135                 140

Asn Lys Leu Asn Ile His Thr Tyr Pro Leu Lys Gly Asn Asn Thr Ser
145                 150                 155                 160

Pro Glu Met Val Ala Ala Ile Asp Glu Tyr Ala Gln Ser Lys Asn Arg
                165                 170                 175

Leu Asn Ile Glu Phe Tyr Thr Asn Thr Ala His Val Phe Asn Asn Leu
            180                 185                 190

Pro Pro Ile Ile Gln Pro Leu Tyr Asn Asn Glu Lys Val Lys Ile Ser
        195                 200                 205

His Ile Ser Leu Tyr Asp Asp Gly Ser Ser Glu Tyr Val Ser Leu Tyr
    210                 215                 220

Gln Trp Lys Asp Thr Pro Asn Lys Ile Glu Thr Leu Glu Gly Glu Val
225                 230                 235                 240

Ser Leu Leu Ala Asn Tyr Leu Ala Gly Thr Ser Pro Asp Ala Pro Lys
                245                 250                 255

Gly Met Gly Asn Arg Tyr Asn Trp His Lys Leu Tyr Asp Thr Asp Tyr
            260                 265                 270

Tyr Phe Leu Arg Glu Asp Tyr Leu Asp Val Glu Ala Asn Leu His Asp
        275                 280                 285

Leu Arg Asp Tyr Leu Gly Ser Ser Ala Lys Gln Met Pro Trp Asp Glu
    290                 295                 300

Phe Ala Lys Leu Ser Asp Ser Gln Gln Thr Leu Phe Leu Asp Ile Val
305                 310                 315                 320

Gly Phe Asp Lys Glu Gln Leu Gln Gln Gln Tyr Ser Gln Ser Pro Leu
                325                 330                 335

Pro Asn Phe Ile Phe Thr Gly Thr Thr Trp Ala Gly Gly Glu Thr
            340                 345                 350

Lys Glu Tyr Tyr Ala Gln Gln Gln Val Asn Val Ile Asn Asn Ala Ile
        355                 360                 365

Asn Glu Thr Ser Pro Tyr Tyr Leu Gly Lys Asp Tyr Asp Leu Phe Phe
    370                 375                 380

Lys Gly His Pro Ala Gly Gly Val Ile Asn Asp Ile Ile Leu Gly Ser
385                 390                 395                 400

Phe Pro Asp Met Ile Asn Ile Pro Ala Lys Thr Ser Phe Glu Val Leu
```

```
                    405                 410                 415
Met Met Thr Asp Met Leu Pro Asp Thr Val Ala Gly Ile Ala Ser Ser
                420                 425                 430

Leu Tyr Phe Thr Ile Pro Ala Asp Lys Val Asn Phe Ile Val Phe Thr
            435                 440                 445

Ser Ser Asp Thr Ile Thr Asp Arg Glu Glu Ala Leu Lys Ser Pro Leu
        450                 455                 460

Val Gln Val Met Leu Thr Leu Gly Ile Val Lys Glu Lys Asp Val Leu
465                 470                 475                 480

Phe Trp Ala

<210> SEQ ID NO 15
<211> LENGTH: 483
<212> TYPE: PRT
<213> ORGANISM: Artificial Sequence
<220> FEATURE:
<223> OTHER INFORMATION: L433S

<400> SEQUENCE: 15

Met Cys Asn Ser Asp Asn Thr Ser Leu Lys Glu Thr Val Ser Ser Asn
1               5                   10                  15

Ser Ala Asp Val Val Glu Thr Glu Tyr Gln Leu Thr Pro Ile Asp
            20                  25                  30

Ala Pro Ser Ser Phe Leu Ser His Ser Trp Gln Thr Cys Gly Thr
        35                  40                  45

Pro Ile Leu Asn Glu Ser Asp Lys Gln Ala Ile Ser Phe Asp Phe Val
    50                  55                  60

Ala Pro Glu Leu Lys Gln Asp Glu Lys Tyr Cys Phe Thr Phe Lys Gly
65                  70                  75                  80

Ile Thr Gly Asp His Arg Tyr Ile Thr Asn Thr Leu Thr Val Val
                85                  90                  95

Ala Pro Thr Leu Glu Val Tyr Ile Asp His Ala Ser Leu Pro Ser Leu
            100                 105                 110

Gln Gln Leu Ile His Ile Ile Gln Ala Lys Asp Glu Tyr Pro Ser Asn
        115                 120                 125

Gln Arg Phe Val Ser Trp Lys Arg Val Thr Val Asp Ala Asp Asn Ala
130                 135                 140

Asn Lys Leu Asn Ile His Thr Tyr Pro Leu Lys Gly Asn Asn Thr Ser
145                 150                 155                 160

Pro Glu Met Val Ala Ala Ile Asp Glu Tyr Ala Gln Ser Lys Asn Arg
                165                 170                 175

Leu Asn Ile Glu Phe Tyr Thr Asn Thr Ala His Val Phe Asn Asn Leu
            180                 185                 190

Pro Pro Ile Ile Gln Pro Leu Tyr Asn Asn Glu Lys Val Lys Ile Ser
        195                 200                 205

His Ile Ser Leu Tyr Asp Asp Gly Ser Ser Tyr Val Ser Leu Tyr
    210                 215                 220

Gln Trp Lys Asp Thr Pro Asn Lys Ile Glu Thr Leu Glu Gly Glu Val
225                 230                 235                 240

Ser Leu Leu Ala Asn Tyr Leu Ala Gly Thr Ser Pro Asp Ala Pro Lys
                245                 250                 255

Gly Met Gly Asn Arg Tyr Asn Trp His Lys Leu Tyr Asp Thr Asp Tyr
            260                 265                 270

Tyr Phe Leu Arg Glu Asp Tyr Leu Asp Val Glu Ala Asn Leu His Asp
        275                 280                 285
```

```
Leu Arg Asp Tyr Leu Gly Ser Ala Lys Gln Met Pro Trp Asp Glu
        290                 295                 300

Phe Ala Lys Leu Ser Asp Ser Gln Gln Thr Leu Phe Leu Asp Ile Val
305                 310                 315                 320

Gly Phe Asp Lys Glu Gln Leu Gln Gln Gln Tyr Ser Gln Ser Pro Leu
                325                 330                 335

Pro Asn Phe Ile Phe Thr Gly Thr Thr Thr Trp Ala Gly Gly Glu Thr
                340                 345                 350

Lys Glu Tyr Tyr Ala Gln Gln Gln Val Asn Val Ile Asn Asn Ala Ile
                355                 360                 365

Asn Glu Thr Ser Pro Tyr Tyr Leu Gly Lys Asp Tyr Asp Leu Phe Phe
370                 375                 380

Lys Gly His Pro Ala Gly Gly Val Ile Asn Asp Ile Ile Leu Gly Ser
385                 390                 395                 400

Phe Pro Asp Met Ile Asn Ile Pro Ala Lys Ile Ser Phe Glu Val Leu
                405                 410                 415

Met Met Thr Asp Met Leu Pro Asp Thr Val Ala Gly Ile Ala Ser Ser
                420                 425                 430

Ser Tyr Phe Thr Ile Pro Ala Asp Lys Val Asn Phe Ile Val Phe Thr
                435                 440                 445

Ser Ser Asp Thr Ile Thr Asp Arg Glu Glu Ala Leu Lys Ser Pro Leu
450                 455                 460

Val Gln Val Met Leu Thr Leu Gly Ile Val Lys Glu Lys Asp Val Leu
465                 470                 475                 480

Phe Trp Ala

<210> SEQ ID NO 16
<211> LENGTH: 483
<212> TYPE: PRT
<213> ORGANISM: Artificial Sequence
<220> FEATURE:
<223> OTHER INFORMATION: L433T

<400> SEQUENCE: 16

Met Cys Asn Ser Asp Asn Thr Ser Leu Lys Glu Thr Val Ser Ser Asn
1               5                   10                  15

Ser Ala Asp Val Val Glu Thr Glu Thr Tyr Gln Leu Thr Pro Ile Asp
                20                  25                  30

Ala Pro Ser Ser Phe Leu Ser His Ser Trp Glu Gln Thr Cys Gly Thr
                35                  40                  45

Pro Ile Leu Asn Glu Ser Asp Lys Gln Ala Ile Ser Phe Asp Phe Val
        50                  55                  60

Ala Pro Glu Leu Lys Gln Asp Glu Lys Tyr Cys Phe Thr Phe Lys Gly
65                  70                  75                  80

Ile Thr Gly Asp His Arg Tyr Ile Thr Asn Thr Thr Leu Thr Val Val
                85                  90                  95

Ala Pro Thr Leu Glu Val Tyr Ile Asp His Ala Ser Leu Pro Ser Leu
                100                 105                 110

Gln Gln Leu Ile His Ile Ile Gln Ala Lys Asp Glu Tyr Pro Ser Asn
                115                 120                 125

Gln Arg Phe Val Ser Trp Lys Arg Val Thr Val Asp Ala Asp Asn Ala
        130                 135                 140

Asn Lys Leu Asn Ile His Thr Tyr Pro Leu Lys Gly Asn Asn Thr Ser
145                 150                 155                 160
```

Pro Glu Met Val Ala Ile Asp Glu Tyr Ala Gln Ser Lys Asn Arg
            165                 170                 175

Leu Asn Ile Glu Phe Tyr Thr Asn Thr Ala His Val Phe Asn Asn Leu
        180                 185                 190

Pro Pro Ile Ile Gln Pro Leu Tyr Asn Asn Glu Lys Val Lys Ile Ser
            195                 200                 205

His Ile Ser Leu Tyr Asp Asp Gly Ser Ser Gly Tyr Val Ser Leu Tyr
        210                 215                 220

Gln Trp Lys Asp Thr Pro Asn Lys Ile Glu Thr Leu Glu Gly Glu Val
225                 230                 235                 240

Ser Leu Leu Ala Asn Tyr Leu Ala Gly Thr Ser Pro Asp Ala Pro Lys
            245                 250                 255

Gly Met Gly Asn Arg Tyr Asn Trp His Lys Leu Tyr Asp Thr Asp Tyr
            260                 265                 270

Tyr Phe Leu Arg Glu Asp Tyr Leu Asp Val Glu Ala Asn Leu His Asp
            275                 280                 285

Leu Arg Asp Tyr Leu Gly Ser Ser Ala Lys Gln Met Pro Trp Asp Glu
            290                 295                 300

Phe Ala Lys Leu Ser Asp Ser Gln Gln Thr Leu Phe Leu Asp Ile Val
305                 310                 315                 320

Gly Phe Asp Lys Glu Gln Leu Gln Gln Gln Tyr Ser Gln Ser Pro Leu
            325                 330                 335

Pro Asn Phe Ile Phe Thr Gly Thr Thr Thr Trp Ala Gly Gly Glu Thr
            340                 345                 350

Lys Glu Tyr Tyr Ala Gln Gln Gln Val Asn Val Ile Asn Asn Ala Ile
            355                 360                 365

Asn Glu Thr Ser Pro Tyr Tyr Leu Gly Lys Asp Tyr Asp Leu Phe Phe
            370                 375                 380

Lys Gly His Pro Ala Gly Gly Val Ile Asn Asp Ile Ile Leu Gly Ser
385                 390                 395                 400

Phe Pro Asp Met Ile Asn Ile Pro Ala Lys Ile Ser Phe Glu Val Leu
            405                 410                 415

Met Met Thr Asp Met Leu Pro Asp Thr Val Ala Gly Ile Ala Ser Ser
            420                 425                 430

Thr Tyr Phe Thr Ile Pro Ala Asp Lys Val Asn Phe Ile Val Phe Thr
            435                 440                 445

Ser Ser Asp Thr Ile Thr Asp Arg Glu Glu Ala Leu Lys Ser Pro Leu
            450                 455                 460

Val Gln Val Met Leu Thr Leu Gly Ile Val Lys Glu Lys Asp Val Leu
465                 470                 475                 480

Phe Trp Ala

<210> SEQ ID NO 17
<211> LENGTH: 483
<212> TYPE: PRT
<213> ORGANISM: Artificial Sequence
<220> FEATURE:
<223> OTHER INFORMATION: I411T+L433S

<400> SEQUENCE: 17

Met Cys Asn Ser Asp Asn Thr Ser Leu Lys Glu Thr Val Ser Ser Asn
1               5                   10                  15

Ser Ala Asp Val Val Glu Thr Glu Thr Tyr Gln Leu Thr Pro Ile Asp
            20                  25                  30

Ala Pro Ser Ser Phe Leu Ser His Ser Trp Glu Gln Thr Cys Gly Thr

-continued

```
            35                  40                  45
Pro Ile Leu Asn Glu Ser Asp Lys Gln Ala Ile Ser Phe Asp Phe Val
 50                  55                  60

Ala Pro Glu Leu Lys Gln Asp Glu Lys Tyr Cys Phe Thr Phe Lys Gly
 65                  70                  75                  80

Ile Thr Gly Asp His Arg Tyr Ile Thr Asn Thr Thr Leu Thr Val Val
                     85                  90                  95

Ala Pro Thr Leu Glu Val Tyr Ile Asp His Ala Ser Leu Pro Ser Leu
                    100                 105                 110

Gln Gln Leu Ile His Ile Ile Gln Ala Lys Asp Glu Tyr Pro Ser Asn
                    115                 120                 125

Gln Arg Phe Val Ser Trp Lys Arg Val Thr Val Asp Ala Asp Asn Ala
                    130                 135                 140

Asn Lys Leu Asn Ile His Thr Tyr Pro Leu Lys Gly Asn Asn Thr Ser
145                 150                 155                 160

Pro Glu Met Val Ala Ala Ile Asp Glu Tyr Ala Gln Ser Lys Asn Arg
                    165                 170                 175

Leu Asn Ile Glu Phe Tyr Thr Asn Thr Ala His Val Phe Asn Asn Leu
                    180                 185                 190

Pro Pro Ile Ile Gln Pro Leu Tyr Asn Asn Glu Lys Val Lys Ile Ser
                    195                 200                 205

His Ile Ser Leu Tyr Asp Asp Gly Ser Ser Glu Tyr Val Ser Leu Tyr
                    210                 215                 220

Gln Trp Lys Asp Thr Pro Asn Lys Ile Glu Thr Leu Glu Gly Glu Val
225                 230                 235                 240

Ser Leu Leu Ala Asn Tyr Leu Ala Gly Thr Ser Pro Asp Ala Pro Lys
                    245                 250                 255

Gly Met Gly Asn Arg Tyr Asn Trp His Lys Leu Tyr Asp Thr Asp Tyr
                    260                 265                 270

Tyr Phe Leu Arg Glu Asp Tyr Leu Asp Val Glu Ala Asn Leu His Asp
                    275                 280                 285

Leu Arg Asp Tyr Leu Gly Ser Ser Ala Lys Gln Met Pro Trp Asp Glu
                    290                 295                 300

Phe Ala Lys Leu Ser Asp Ser Gln Gln Thr Leu Phe Leu Asp Ile Val
305                 310                 315                 320

Gly Phe Asp Lys Glu Gln Leu Gln Gln Gln Tyr Ser Gln Ser Pro Leu
                    325                 330                 335

Pro Asn Phe Ile Phe Thr Gly Thr Thr Thr Trp Ala Gly Gly Glu Thr
                    340                 345                 350

Lys Glu Tyr Tyr Ala Gln Gln Gln Val Asn Val Ile Asn Asn Ala Ile
                    355                 360                 365

Asn Glu Thr Ser Pro Tyr Tyr Leu Gly Lys Asp Tyr Asp Leu Phe Phe
                    370                 375                 380

Lys Gly His Pro Ala Gly Gly Val Ile Asn Asp Ile Leu Gly Ser
385                 390                 395                 400

Phe Pro Asp Met Ile Asn Ile Pro Ala Lys Thr Ser Phe Glu Val Leu
                    405                 410                 415

Met Met Thr Asp Met Leu Pro Asp Thr Val Ala Gly Ile Ala Ser Ser
                    420                 425                 430

Ser Tyr Phe Thr Ile Pro Ala Asp Lys Val Asn Phe Ile Val Phe Thr
                    435                 440                 445

Ser Ser Asp Thr Ile Thr Asp Arg Glu Glu Ala Leu Lys Ser Pro Leu
450                 455                 460
```

Val Gln Val Met Leu Thr Leu Gly Ile Val Lys Glu Lys Asp Val Leu
465                 470                 475                 480

Phe Trp Ala

<210> SEQ ID NO 18
<211> LENGTH: 483
<212> TYPE: PRT
<213> ORGANISM: Artificial Sequence
<220> FEATURE:
<223> OTHER INFORMATION: I411T+L433T

<400> SEQUENCE: 18

Met Cys Asn Ser Asp Asn Thr Ser Leu Lys Glu Thr Val Ser Ser Asn
1               5                   10                  15

Ser Ala Asp Val Val Glu Thr Glu Thr Tyr Gln Leu Thr Pro Ile Asp
                20                  25                  30

Ala Pro Ser Ser Phe Leu Ser His Ser Trp Glu Gln Thr Cys Gly Thr
            35                  40                  45

Pro Ile Leu Asn Glu Ser Asp Lys Gln Ala Ile Ser Phe Asp Phe Val
        50                  55                  60

Ala Pro Glu Leu Lys Gln Asp Glu Lys Tyr Cys Phe Thr Phe Lys Gly
65                  70                  75                  80

Ile Thr Gly Asp His Arg Tyr Ile Thr Asn Thr Thr Leu Thr Val Val
                85                  90                  95

Ala Pro Thr Leu Glu Val Tyr Ile Asp His Ala Ser Leu Pro Ser Leu
            100                 105                 110

Gln Gln Leu Ile His Ile Ile Gln Ala Lys Asp Glu Tyr Pro Ser Asn
        115                 120                 125

Gln Arg Phe Val Ser Trp Lys Arg Val Thr Val Asp Ala Asp Asn Ala
130                 135                 140

Asn Lys Leu Asn Ile His Thr Tyr Pro Leu Lys Gly Asn Asn Thr Ser
145                 150                 155                 160

Pro Glu Met Val Ala Ala Ile Asp Glu Tyr Ala Gln Ser Lys Asn Arg
                165                 170                 175

Leu Asn Ile Glu Phe Tyr Thr Asn Thr Ala His Val Phe Asn Asn Leu
            180                 185                 190

Pro Pro Ile Ile Gln Pro Leu Tyr Asn Asn Glu Lys Val Lys Ile Ser
        195                 200                 205

His Ile Ser Leu Tyr Asp Asp Gly Ser Ser Glu Tyr Val Ser Leu Tyr
210                 215                 220

Gln Trp Lys Asp Thr Pro Asn Lys Ile Glu Thr Leu Glu Gly Glu Val
225                 230                 235                 240

Ser Leu Leu Ala Asn Tyr Leu Ala Gly Thr Ser Pro Asp Ala Pro Lys
                245                 250                 255

Gly Met Gly Asn Arg Tyr Asn Trp His Lys Leu Tyr Asp Thr Asp Tyr
            260                 265                 270

Tyr Phe Leu Arg Glu Asp Tyr Leu Asp Val Glu Ala Asn Leu His Asp
        275                 280                 285

Leu Arg Asp Tyr Leu Gly Ser Ser Ala Lys Gln Met Pro Trp Asp Glu
290                 295                 300

Phe Ala Lys Leu Ser Asp Ser Gln Gln Thr Leu Phe Leu Asp Ile Val
305                 310                 315                 320

Gly Phe Asp Lys Glu Gln Leu Gln Gln Gln Tyr Ser Gln Ser Pro Leu
                325                 330                 335

```
Pro Asn Phe Ile Phe Thr Gly Thr Thr Thr Trp Ala Gly Gly Glu Thr
                340                 345                 350

Lys Glu Tyr Tyr Ala Gln Gln Val Asn Val Ile Asn Asn Ala Ile
            355                 360                 365

Asn Glu Thr Ser Pro Tyr Tyr Leu Gly Lys Asp Tyr Asp Leu Phe Phe
        370                 375                 380

Lys Gly His Pro Ala Gly Val Ile Asn Asp Ile Ile Leu Gly Ser
385                 390                 395                 400

Phe Pro Asp Met Ile Asn Ile Pro Ala Lys Thr Ser Phe Glu Val Leu
                405                 410                 415

Met Met Thr Asp Met Leu Pro Asp Thr Val Ala Gly Ile Ala Ser Ser
                420                 425                 430

Thr Tyr Phe Thr Ile Pro Ala Asp Lys Val Asn Phe Ile Val Phe Thr
            435                 440                 445

Ser Ser Asp Thr Ile Thr Asp Arg Glu Glu Ala Leu Lys Ser Pro Leu
        450                 455                 460

Val Gln Val Met Leu Thr Leu Gly Ile Val Lys Glu Lys Asp Val Leu
465                 470                 475                 480

Phe Trp Ala

<210> SEQ ID NO 19
<211> LENGTH: 1449
<212> TYPE: DNA
<213> ORGANISM: Photobacterium damselae

<400> SEQUENCE: 19
atgtgtaata gtgacaatac cagcttgaaa gaaacggtaa gctctaattc tgcagatgta      60
gtagaaacag aaacttacca actgacaccg attgatgctc ctagctcttt tttatctcat     120
tcttgggagc aaacatgtgg cacacctatc ttgaatgaaa gtgacaagca agcgatatct     180
tttgattttg ttgctccaga gttaaagcaa gatgaaaagt attgttttac ttttaaaggt     240
attacaggcg atcataggta tatcacaaat acaacattaa ctgttgttgc acctacgcta     300
gaagtttaca tcgatcatgc atccttacca tcgctacagc agcttatcca cattattcaa     360 gcaaagatg aatacccaag taatcaacgt tttgtctctt ggaagcgtgt aactgttgat     420
gctgataatg ccaataagtt aaacattcat acttatccat aaaaggcaa taatacctca     480 ccagaaatgg tggcagcgat tgatgagtat gctcagagca aaaatcgatt gaatatagag     540
ttctatacaa atacagctca tgtttttaat aatttaccac ctattattca acctttatat     600
aataacgaga aggtgaaaat ttctcatatt agtttgtatg atgatggttc ttctgaatat     660
gtaagtttat atcaatggaa agatacacca aataagatag aacattaga aggtgaagta     720 tcgcttcttg ctaattattt agcaggaaca tctccggatg caccaaaagg aatgggaaat     780
cgttataact ggcataaatt atatgacact gattattact ttttgcgcga agattacctt     840
gacgttgaag caaacctaca tgatttacgt gattatttag gctcttccgc aaagcaaatg     900
ccatgggatg aatttgctaa attatctgat tctcagcaaa cactatttt agatattgtg     960 ggttttgata agagcaatt gcaacaacaa tattcacaat ccccactacc aaactttatt    1020
tttaccggca caacaacttg ggctggggggg gaaacgaaag agtattatgc tcagcaacaa    1080
gtaaatgtga ttaataatgc gatcaatgaa actagccctt attatttagg taaagactac    1140
gatctatttt tcaagggggca tcctgctggt ggcgttatta acgacatcat tcttggaagc    1200
ttccctgata tgatcaatat tccagccaag atttcatttg aggtcttgat gatgacggat    1260
```

-continued

```
atgttgcctg atacagtagc tggtattgcg agctctctgt acttcacaat tcctgccgat     1320
aaagttaatt ttattgtatt tacttcatct gacactatta ctgatcgtga agaggctctt     1380
aaatcaccat tagtacaagt gatgctaacg ttgggtattg ttaaagaaaa agatgttctg     1440
ttctgggct                                                             1449
```

<210> SEQ ID NO 20
<211> LENGTH: 1449
<212> TYPE: DNA
<213> ORGANISM: Artificial Sequence
<220> FEATURE:
<223> OTHER INFORMATION: I411T

<400> SEQUENCE: 20

```
atgtgtaata gtgacaatac cagcttgaaa gaaacggtaa gctctaattc tgcagatgta      60
gtagaaacag aaacttacca actgacaccg attgatgctc ctagctcttt tttatctcat     120
tcttgggagc aaacatgtgg cacacctatc ttgaatgaaa gtgacaagca agcgatatct     180
tttgattttg ttgctccaga gttaaagcaa gatgaaaagt attgttttac ttttaaaggt     240
attacaggcg atcataggta tatcacaaat acaacattaa ctgttgttgc acctacgcta     300
gaagtttaca tcgatcatgc atccttacca tcgctacagc agcttatcca cattattcaa     360 gcaaagatg aatacccaag taatcaacgt tttgtctctt ggaagcgtgt aactgttgat     420
gctgataatg ccaataagtt aaacattcat acttatccat aaaaggcaa taatacctca     480 ccagaaatgg tggcagcgat tgatgagtat gctcagagca aaaatcgatt gaatatagag     540
ttctatacaa atacagctca tgtttttaat aatttaccac ctattattca acctttatat    600
aataacgaga aggtgaaaat ttctcatatt agtttgtatg atgatggttc ttctgaatat    660
gtaagtttat atcaatggaa agatacacca aataagatag aaacattaga aggtgaagta    720
tcgcttcttg ctaattattt agcaggaaca tctccggatg caccaaaagg aatgggaaat    780
cgttataact ggcataaatt tatgacact gattattact ttttgcgcga agattacctt    840
gacgttgaag caaacctaca tgatttacgt gattatttag gctcttccgc aaagcaaatg    900
ccatgggatg aatttgctaa attatctgat tctcagcaaa cactattttt agatattgtg    960
ggttttgata agagcaatt gcaacaacaa tattcacaat ccccactacc aaactttatt    1020
tttaccggca caacaacttg ggctggggggg gaaacgaaag agtattatgc tcagcaacaa   1080
gtaaatgtga ttaataatgc gatcaatgaa actagcccctt attatttagg taaagactac   1140
gatctatttt tcaagggggca tcctgctggt ggcgttatta cgacatcat tcttggaagc    1200 ttccctgata tgatcaatat tccagccaag acttcatttg aggtcttgat gatgacggat    1260
atgttgcctg atacagtagc tggtattgcg agctctctgt acttcacaat tcctgccgat    1320
aaagttaatt ttattgtatt tacttcatct gacactatta ctgatcgtga agaggctctt    1380
aaatcaccat tagtacaagt gatgctaacg ttgggtattg ttaaagaaaa agatgttctg    1440
ttctgggct                                                           1449
```

<210> SEQ ID NO 21
<211> LENGTH: 1449
<212> TYPE: DNA
<213> ORGANISM: Artificial Sequence
<220> FEATURE:
<223> OTHER INFORMATION: L433S

<400> SEQUENCE: 21

```
atgtgtaata gtgacaatac cagcttgaaa gaaacggtaa gctctaattc tgcagatgta      60
```

```
gtagaaacag aaacttacca actgacaccg attgatgctc ctagctcttt tttatctcat      120
tcttgggagc aaacatgtgg cacacctatc ttgaatgaaa gtgacaagca agcgatatct      180
tttgattttg ttgctccaga gttaaagcaa gatgaaaagt attgttttac ttttaaaggt      240
attacaggcg atcataggta tatcacaaat acaacattaa ctgttgttgc acctacgcta      300
gaagtttaca tcgatcatgc atccttacca tcgctacagc agcttatcca cattattcaa      360
gcaaaagatg aatacccaag taatcaacgt tttgtctctt ggaagcgtgt aactgttgat      420
gctgataatg ccaataagtt aaacattcat acttatccat aaaaggcaa taatacctca       480 ccagaaatgg tggcagcgat tgatgagtat gctcagagca aaaatcgatt gaatatagag      540
ttctatacaa atacagctca tgtttttaat aatttaccac ctattattca acctttatat      600
aataacgaga aggtgaaaat ttctcatatt agtttgtatg atgatggttc ttctgaatat      660
gtaagtttat atcaatggaa agatacacca aataagatag aaacattaga aggtgaagta      720
tcgcttcttg ctaattattt agcaggaaca tctccggatg caccaaaagg aatgggaaat      780
cgttataact ggcataaatt atatgacact gattattact ttttgcgcga agattacctt      840
gacgttgaag caaacctaca tgatttacgt gattatttag gctcttccgc aaagcaaatg      900
ccatgggatg aatttgctaa attatctgat tctcagcaaa cactattttt agatattgtg      960
ggttttgata aagagcaatt gcaacaacaa tattcacaat ccccactacc aaactttatt     1020
tttaccggca caacaacttg ggctggggg gaaacgaaag agtattatgc tcagcaacaa     1080
gtaaatgtga ttaataatgc gatcaatgaa actagcccct tattatttagg taaagactac     1140 gatctatttt tcaaggggca tcctgctggt ggcgttatta acgacatcat tcttggaagc     1200
ttccctgata tgatcaatat tccagccaag acttcatttg aggtcttgat gatgacggat     1260
atgttgcctg atacagtagc tggtattgcg agctctagtt acttcacaat tcctgccgat     1320
aaagttaatt ttattgtatt tacttcatct gacactatta ctgatcgtga agaggctctt     1380
aaatcaccat tagtacaagt gatgctaacg ttgggtattg ttaaagaaaa agatgttctg     1440
ttctgggct                                                            1449
```

<210> SEQ ID NO 22
<211> LENGTH: 1449
<212> TYPE: DNA
<213> ORGANISM: Artificial Sequence
<220> FEATURE:
<223> OTHER INFORMATION: L433T

<400> SEQUENCE: 22

```
atgtgtaata gtgacaatac cagcttgaaa gaaacggtaa gctctaattc tgcagatgta       60
gtagaaacag aaacttacca actgacaccg attgatgctc ctagctcttt tttatctcat      120
tcttgggagc aaacatgtgg cacacctatc ttgaatgaaa gtgacaagca agcgatatct      180
tttgattttg ttgctccaga gttaaagcaa gatgaaaagt attgttttac ttttaaaggt      240
attacaggcg atcataggta tatcacaaat acaacattaa ctgttgttgc acctacgcta      300
gaagtttaca tcgatcatgc atccttacca tcgctacagc agcttatcca cattattcaa      360
gcaaaagatg aatacccaag taatcaacgt tttgtctctt ggaagcgtgt aactgttgat      420
gctgataatg ccaataagtt aaacattcat acttatccat aaaaggcaa taatacctca       480 ccagaaatgg tggcagcgat tgatgagtat gctcagagca aaaatcgatt gaatatagag      540
ttctatacaa atacagctca tgtttttaat aatttaccac ctattattca acctttatat      600
```

| | |
|---|---|
| aataacgaga aggtgaaaat ttctcatatt agtttgtatg atgatggttc ttctgaatat | 660 |
| gtaagtttat atcaatggaa agatacacca aataagatag aaacattaga aggtgaagta | 720 |
| tcgcttcttg ctaattattt agcaggaaca tctccggatg caccaaaagg aatgggaaat | 780 |
| cgttataact ggcataaatt atatgacact gattattact ttttgcgcga agattacctt | 840 |
| gacgttgaag caaacctaca tgatttacgt gattatttag gctcttccgc aaagcaaatg | 900 |
| ccatgggatg aatttgctaa attatctgat tctcagcaaa cactattttt agatattgtg | 960 |
| ggttttgata aagagcaatt gcaacaacaa tattcacaat ccccactacc aaactttatt | 1020 |
| tttaccggca caacaacttg ggctggggg gaaacgaaag agtattatgc tcagcaacaa | 1080 |
| gtaaatgtga ttaataatgc gatcaatgaa actagccctt attatttagg taaagactac | 1140 |
| gatctatttt tcaaggggca tcctgctggt ggcgttatta acgacatcat tcttggaagc | 1200 |
| ttccctgata tgatcaatat tccagccaag acttcatttg aggtcttgat gatgacggat | 1260 |
| atgttgcctg atacagtagc tggtattgcg agctctacgt acttcacaat tcctgccgat | 1320 |
| aaagttaatt ttattgtatt tacttcatct gacactatta ctgatcgtga agaggctctt | 1380 |
| aaatcaccat tagtacaagt gatgctaacg ttgggtattg ttaaagaaaa agatgttctg | 1440 |
| ttctgggct | 1449 |

<210> SEQ ID NO 23
<211> LENGTH: 1449
<212> TYPE: DNA
<213> ORGANISM: Artificial Sequence
<220> FEATURE:
<223> OTHER INFORMATION: I411T + L433S

<400> SEQUENCE: 23

| | |
|---|---|
| atgtgtaata gtgacaatac cagcttgaaa gaaacggtaa gctctaattc tgcagatgta | 60 |
| gtagaaacag aaacttacca actgacaccg attgatgctc ctagctcttt tttatctcat | 120 |
| tcttgggagc aaacatgtgg cacacctatc ttgaatgaaa gtgacaagca agcgatatct | 180 |
| tttgattttg ttgctccaga gttaaagcaa gatgaaaagt attgttttac ttttaaaggt | 240 |
| attacaggcg atcataggta tatcacaaat acaacattaa ctgttgttgc acctacgcta | 300 |
| gaagtttaca tcgatcatgc atccttacca tcgctacagc agcttatcca cattattcaa | 360 |
| gcaaaagatg aatacccaag taatcaacgt tttgtctctt ggaagcgtgt aactgttgat | 420 |
| gctgataatg ccaataagtt aaacattcat acttatccat taaaaggcaa taatacctca | 480 |
| ccagaaatgg tggcagcgat tgatgagtat gctcagagca aaaatcgatt gaatatagag | 540 |
| ttctatacaa atacagctca tgttttaat aatttaccac ctattattca acctttatat | 600 |
| aataacgaga aggtgaaaat ttctcatatt agtttgtatg atgatggttc ttctgaatat | 660 |
| gtaagtttat atcaatggaa agatacacca aataagatag aaacattaga aggtgaagta | 720 |
| tcgcttcttg ctaattattt agcaggaaca tctccggatg caccaaaagg aatgggaaat | 780 |
| cgttataact ggcataaatt atatgacact gattattact ttttgcgcga agattacctt | 840 |
| gacgttgaag caaacctaca tgatttacgt gattatttag gctcttccgc aaagcaaatg | 900 |
| ccatgggatg aatttgctaa attatctgat tctcagcaaa cactattttt agatattgtg | 960 |
| ggttttgata aagagcaatt gcaacaacaa tattcacaat ccccactacc aaactttatt | 1020 |
| tttaccggca caacaacttg ggctggggg gaaacgaaag agtattatgc tcagcaacaa | 1080 |
| gtaaatgtga ttaataatgc gatcaatgaa actagccctt attatttagg taaagactac | 1140 |
| gatctatttt tcaaggggca tcctgctggt ggcgttatta acgacatcat tcttggaagc | 1200 |

```
ttccctgata tgatcaatat tccagccaag acttcatttg aggtcttgat gatgacggat    1260
atgttgcctg atacagtagc tggtattgcg agctctagtt acttcacaat tcctgccgat    1320
aaagttaatt ttattgtatt tacttcatct gacactatta ctgatcgtga agaggctctt    1380
aaatcaccat tagtacaagt gatgctaacg ttgggtattg ttaaagaaaa agatgttctg    1440
ttctgggct                                                           1449
```

<210> SEQ ID NO 24
<211> LENGTH: 1449
<212> TYPE: PRT
<213> ORGANISM: Artificial Sequence
<220> FEATURE:
<223> OTHER INFORMATION: I411T + L433T

<400> SEQUENCE: 24

```
Ala Thr Gly Thr Gly Thr Ala Ala Thr Ala Gly Thr Gly Ala Cys Ala
1               5                   10                  15

Ala Thr Ala Cys Cys Ala Gly Cys Thr Thr Gly Ala Ala Ala Gly Ala
            20                  25                  30

Ala Ala Cys Gly Gly Thr Ala Ala Gly Cys Thr Cys Thr Ala Ala Thr
        35                  40                  45

Thr Cys Thr Gly Cys Ala Gly Ala Thr Gly Thr Ala Gly Thr Ala Gly
    50                  55                  60

Ala Ala Ala Cys Ala Gly Ala Ala Cys Thr Thr Ala Cys Cys Ala
65                  70                  75                  80

Ala Cys Thr Gly Ala Cys Ala Cys Cys Gly Ala Thr Thr Gly Ala Thr
            85                  90                  95

Gly Cys Thr Cys Cys Thr Ala Gly Cys Thr Cys Thr Thr Thr Thr Thr
            100                 105                 110

Thr Ala Thr Cys Thr Cys Ala Thr Thr Cys Thr Thr Gly Gly Gly Ala
        115                 120                 125

Gly Cys Ala Ala Ala Cys Ala Thr Gly Thr Gly Gly Cys Ala Cys Ala
    130                 135                 140

Cys Cys Thr Ala Thr Cys Thr Thr Gly Ala Ala Thr Gly Ala Ala Ala
145                 150                 155                 160

Gly Thr Gly Ala Cys Ala Ala Gly Cys Ala Ala Gly Cys Gly Ala Thr
            165                 170                 175

Ala Thr Cys Thr Thr Thr Thr Gly Ala Thr Thr Thr Gly Thr Thr
        180                 185                 190

Gly Cys Thr Cys Cys Ala Gly Ala Gly Thr Thr

```
            305                 310                 315                 320
Ala Thr Cys Cys Thr Thr Ala Cys Cys Ala Thr Cys Gly Cys Thr Ala
                325                 330                 335
Cys Ala Gly Cys Ala Gly Cys Thr Thr Ala Thr Cys Cys Ala Cys Ala
                340                 345                 350
Thr Thr Ala Thr Thr Cys Ala Ala Gly Cys Ala Ala Ala Gly Ala
                355                 360                 365
Thr Gly Ala Ala Thr Ala Cys Cys Ala Ala Gly Thr Ala Ala Thr
        370                 375                 380
Cys Ala Ala Cys Gly Thr Thr Thr Gly Thr Cys Thr Cys Thr Thr
385                 390                 395                 400
Gly Gly Ala Ala Gly Cys Gly Thr Gly Thr Ala Ala Cys Thr Gly Thr
                405                 410                 415
Thr Gly Ala Thr Gly Cys Thr Gly Ala Thr Ala Thr Gly Cys Cys
        420                 425                 430
Ala Ala Thr Ala Ala Gly Thr Thr Ala Ala Cys Ala Thr Thr Cys
        435                 440                 445
Ala Thr Ala Cys Thr Thr Ala Thr Cys Cys Ala Thr Thr Ala Ala Ala
    450                 455                 460
Ala Gly Gly Cys Ala Ala Thr Ala Thr Ala Cys Cys Thr Cys Ala
465                 470                 475                 480
Cys Cys Ala Gly Ala Ala Ala Thr Gly Gly Thr Gly Gly Cys Ala Gly
                485                 490                 495
Cys Gly Ala Thr Thr Gly Ala Thr Gly Ala Gly Thr Ala Thr Gly Cys
                500                 505                 510
Thr Cys Ala Gly Ala Gly Cys Ala Ala Ala Ala Thr Cys Gly Ala
        515                 520                 525
Thr Thr Gly Ala Ala Thr Ala Gly Ala Gly Thr Thr Cys Thr
        530                 535                 540
Ala Thr Ala Cys Ala Ala Ala Thr Ala Cys Ala Gly Cys Thr Cys Ala
545                 550                 555                 560
Thr Gly Thr Thr Thr Thr Thr Ala Ala Thr Ala Ala Thr Thr Ala
                565                 570                 575
Cys Cys Ala Cys Cys Thr Ala Thr Thr Ala Thr Cys Ala Ala Cys
                580                 585                 590
Cys Thr Thr Thr Ala Thr Ala Thr Ala Ala Cys Gly Ala
                595                 600                 605
Gly Ala Ala Gly Gly Thr Gly Ala Ala Ala Thr Thr Thr Cys Thr
        610                 615                 620
Cys Ala Thr Ala Thr Thr Ala Gly Thr Thr Thr Gly Thr Ala Thr Gly
625                 630                 635                 640
Ala Thr Gly Ala Thr Gly Gly Thr Thr Cys Thr Cys Thr Gly Ala
                645                 650                 655
Ala Thr Ala Thr Gly Thr Ala Ala Gly Thr Thr Ala Thr Ala Thr
                660                 665                 670
Cys Ala Ala Thr Gly Gly Ala Ala Ala Gly Ala Thr Ala Cys Ala Cys
            675                 680                 685
Cys Ala Ala Ala Thr Ala Ala Gly Ala Thr Ala Gly Ala Ala Ala Cys
            690                 695                 700
Ala Thr Thr Ala Gly Ala Ala Gly Gly Thr Gly Ala Ala Gly Thr Ala
705                 710                 715                 720
Thr Cys Gly Cys Thr Thr Cys Thr Thr Gly Cys Thr Ala Ala Thr Thr
                725                 730                 735
```

```
Ala Thr Thr Thr Ala Gly Cys Ala Gly Gly Ala Ala Cys Ala Thr Cys
                740                 745                 750

Thr Cys Cys Gly Gly Ala Thr Gly Cys Ala Cys Ala Ala Ala
            755                 760                 765

Gly Gly Ala Ala Thr Gly Gly Ala Ala Thr Cys Gly Thr Thr
        770                 775                 780

Ala Thr Ala Ala Cys Thr Gly Gly Cys Ala Thr Ala Ala Thr Thr
785                 790                 795                 800

Ala Thr Ala Thr Gly Ala Cys Ala Cys Thr Gly Ala Thr Ala Thr
                805                 810                 815

Thr Ala Cys Thr Thr Thr Thr Thr Gly Cys Gly Cys Gly Ala Ala Gly
        820                 825                 830

Ala Thr Thr Ala Cys Cys Thr Gly Ala Cys Gly Thr Thr Gly Ala
            835                 840                 845

Ala Gly Cys Ala Ala Cys Cys Thr Ala Cys Ala Thr Gly Ala Thr
    850                 855                 860

Thr Thr Ala Cys Gly Thr Gly Ala Thr Thr Ala Thr Thr Ala Gly
865                 870                 875                 880

Gly Cys Thr Cys Thr Cys Cys Gly Cys Ala Ala Gly Cys Ala
                885                 890                 895

Ala Ala Thr Gly Cys Cys Ala Thr Gly Gly Ala Thr Gly Ala Ala
            900                 905                 910

Thr Thr Thr Gly Cys Thr Ala Ala Ala Thr Thr Ala Thr Cys Thr Gly
        915                 920                 925

Ala Thr Thr Cys Thr Cys Ala Gly Cys Ala Ala Cys Ala Cys Thr
    930                 935                 940

Ala Thr Thr Thr Thr Thr Ala Gly Ala Thr Ala Thr Gly Thr Gly
945                 950                 955                 960

Gly Gly Thr Thr Thr Thr Gly Ala Thr Ala Ala Ala Gly Ala Gly Cys
                965                 970                 975

Ala Ala Thr Thr Gly Cys Ala Ala Cys Ala Ala Cys Ala Ala Thr Ala
            980                 985                 990

Thr Thr Cys Ala Cys Ala Ala Thr  Cys Cys Cys Cys Ala  Cys Thr Ala
        995                 1000                1005

Cys Cys  Ala Ala Ala Cys Thr  Thr Thr Ala Thr Thr  Thr Thr Thr
    1010                1015                1020

Ala Cys  Cys Gly Gly Cys Ala  Cys Ala Ala Cys Ala  Ala Cys Thr
    1025                1030                1035

Thr Gly  Gly Gly Cys Thr Gly  Gly Gly Gly Gly Gly  Gly Ala Ala
    1040                1045                1050

Ala Cys  Gly Ala Ala Ala Gly  Ala Gly Thr Ala Thr  Thr Ala Thr
    1055                1060                1065

Gly Cys  Thr Cys Ala Gly Cys  Ala Ala Cys Ala Ala  Gly Thr Ala
    1070                1075                1080

Ala Ala  Thr Gly Thr Gly Ala  Thr Thr Ala Ala Thr  Ala Ala Thr
    1085                1090                1095

Gly Cys  Gly Ala Thr Cys Ala  Ala Thr Gly Ala Ala  Ala Cys Thr
    1100                1105                1110

Ala Gly  Cys Cys Cys Thr Thr  Ala Thr Ala Thr  Thr Thr Ala
    1115                1120                1125

Gly Gly  Thr Ala Ala Ala Gly  Ala Cys Thr Ala Cys  Gly Ala Thr
    1130                1135                1140
```

-continued

Cys Thr Ala Thr Thr Thr Thr Cys Ala Ala Gly Gly Gly Gly
    1145                1150                1155

Cys Ala Thr Cys Cys Thr Gly Cys Thr Gly Gly Thr Gly Gly Cys
    1160                1165                1170

Gly Thr Thr Ala Thr Thr Ala Ala Cys Gly Ala Cys Ala Thr Cys
    1175                1180                1185

Ala Thr Thr Cys Thr Thr Gly Gly Ala Ala Gly Cys Thr Thr Cys
    1190                1195                1200

Cys Cys Thr Gly Ala Thr Ala Thr Gly Ala Thr Cys Ala Ala Thr
    1205                1210                1215

Ala Thr Thr Cys Cys Ala Gly Cys Cys Ala Ala Gly Ala Cys Thr
    1220                1225                1230

Thr Cys Ala Thr Thr Thr Gly Ala Gly Gly Thr Cys Thr Thr Gly
    1235                1240                1245

Ala Thr Gly Ala Thr Gly Ala Cys Gly Gly Ala Thr Ala Thr Gly
    1250                1255                1260

Thr Thr Gly Cys Cys Thr Gly Ala Thr Ala Cys Ala Gly Thr Ala
    1265                1270                1275

Gly Cys Thr Gly Gly Thr Ala Thr Thr Gly Cys Gly Ala Gly Cys
    1280                1285                1290

Thr Cys Thr Ala Cys Cys Thr Ala Cys Thr Thr Cys Ala Cys Ala
    1295                1300                1305

Ala Thr Thr Cys Cys Thr Gly Cys Cys Gly Ala Thr Ala Ala Ala
    1310                1315                1320

Gly Thr Thr Ala Ala Thr Thr Thr Thr Ala Thr Thr Gly Thr Ala
    1325                1330                1335

Thr Thr Thr Ala Cys Thr Thr Cys Ala Thr Cys Thr Gly Ala Cys
    1340                1345                1350

Ala Cys Thr Ala Thr Thr Ala Cys Thr Gly Ala Thr Cys Gly Thr
    1355                1360                1365

Gly Ala Ala Gly Ala Gly Gly Cys Thr Cys Thr Ala Ala Ala
    1370                1375                1380

Thr Cys Ala Cys Cys Ala Thr Thr Ala Gly Thr Ala Cys Ala Ala
    1385                1390                1395

Gly Thr Gly Ala Thr Gly Cys Thr Ala Ala Cys Gly Thr Thr Gly
    1400                1405                1410

Gly Gly Thr Ala Thr Thr Gly Thr Thr Ala Ala Ala Gly Ala Ala
    1415                1420                1425

Ala Ala Ala Gly Ala Thr Gly Thr Thr Cys Thr Gly Thr Thr Cys
    1430                1435                1440

Thr Gly Gly Gly Cys Thr
    1445

<210> SEQ ID NO 25
<211> LENGTH: 394
<212> TYPE: PRT
<213> ORGANISM: Bacteroides fragilis

<400> SEQUENCE: 25

Met Asn Thr Thr Glu Tyr Leu Gln Thr Trp Ser Asp Ser Tyr Lys Asn
1               5                   10                  15

Asp Met Ile Ser Asn Ile Met Pro Phe Trp Met Lys Tyr Gly Trp Asp
            20                  25                  30

Arg Lys Asn Gly Gly Val Tyr Thr Cys Val Asp Arg Asp Gly Gln Leu
        35                  40                  45

```
Met Asp Thr Thr Lys Ser Val Trp Phe Gln Gly Arg Phe Ala Phe Thr
 50                  55                  60
Cys Ser Tyr Ala Tyr Asn His Ile Glu Arg Asn Thr Glu Trp Leu Ala
 65                  70                  75                  80
Ala Ala Lys Ser Thr Leu Asp Phe Ile Glu Ala His Cys Phe Asp Thr
                 85                  90                  95
Asp Gly Arg Met Phe Phe Glu Val Thr Glu Thr Gly Leu Pro Ile Arg
                100                 105                 110
Lys Arg Arg Tyr Val Phe Ser Glu Thr Phe Ala Ala Ile Ala Met Ser
                115                 120                 125
Glu Tyr Ala Ile Ala Ser Gly Asp His Ser Tyr Ala Val Lys Ala Leu
130                 135                 140
Lys Leu Phe Asn Asp Ile Arg His Phe Leu Ser Thr Pro Gly Ile Leu
145                 150                 155                 160
Glu Pro Lys Tyr Cys Glu Arg Val Gln Met Lys Gly His Ser Ile Ile
                165                 170                 175
Met Ile Leu Ile Asn Val Ala Ser Arg Ile Arg Ala Ala Ile Asn Asp
                180                 185                 190
Pro Val Leu Asp Arg Gln Ile Glu Glu Ser Ile Ala Ile Leu His Lys
                195                 200                 205
Asp Phe Met His Pro Glu Phe Lys Ala Leu Leu Glu Thr Val Gly Pro
210                 215                 220
Asn Gly Glu Phe Ile Asp Thr Asn Ala Thr Arg Thr Ile Asn Pro Gly
225                 230                 235                 240
His Cys Ile Glu Thr Ser Trp Phe Ile Leu Glu Glu Ala Lys Asn Arg
                245                 250                 255
Asn Trp Asp Lys Glu Met Val Asp Thr Ala Leu Thr Ile Leu Asp Trp
                260                 265                 270
Ser Trp Glu Trp Gly Trp Asp Lys Gly Tyr Gly Gly Ile Ile Asn Phe
                275                 280                 285
Arg Asp Cys Arg Asn Leu Pro Ser Gln Asp Tyr Ala His Asp Met Lys
                290                 295                 300
Phe Trp Trp Pro Gln Thr Glu Ala Ile Ile Ala Thr Leu Tyr Ala Tyr
305                 310                 315                 320
Gln Ala Thr Lys Asn Glu Lys Tyr Leu Ala Met His Lys Gln Ile Ser
                325                 330                 335
Asp Trp Thr Tyr Ala His Phe Pro Asp Ala Glu Phe Gly Glu Trp Tyr
                340                 345                 350
Gly Tyr Leu His Arg Asp Gly Thr Ile Ser Gln Pro Ala Lys Gly Asn
                355                 360                 365
Leu Phe Lys Gly Pro Phe His Ile Pro Arg Met Met Thr Lys Gly Tyr
370                 375                 380
Ala Leu Cys Gln Glu Leu Leu Ser Glu Lys
385                 390

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
ctgccatggt tatgaatact acag                                    24
```

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
aatggatcct tatttttctg acag                                          24

<210> SEQ ID NO 28
<211> LENGTH: 893
<212> TYPE: DNA
<213> ORGANISM: Escherichia coli

<400> SEQUENCE: 28
atggcaacga atttacgtgg cgtaatggct gcactcctga ctccttttga ccaacaacaa    60
gcactggata aagcgagtct gcgtcgcctg gttcagttca atattcagca gggcatcgac   120
ggtttatacg tgggtggttc gaccggcgag gcctttgtac aaagcctttc cgagcgtgaa   180
caggtactgg aaatcgtcgc cgaagagggc aaaggtaaga ttaaactcat cgcccacgtc   240
ggttgcgtca cgaccgccga aagccaacaa cttgcggcat cggctaaacg ttatggcttc   300
gatgccgtct ccgccgtcac gccgttctac tatccttca gctttgaaga acactgcgat   360
cactatcggg caattattga ttcggcggat ggtttgccga tggtggtgta caacattcca   420
gccctgagtg gggtaaaaact gaccctggat cagatcaaca cacttgttac attgcctggc   480
gtaggtgcgc tgaaacagac ctctggcgat ctctatcaga tggagcagat ccgtcgtgaa   540
catcctgatc ttgtgctcta taacggttac ggagaaatct tcgcctctgg tctgctggcg   600
ggcgctgatg tggtatcgg cagtacctac aacatcatgg gctggcgcta tcagggatc   660 gttaaggcgc tgaaagaagg cgatatccag accgcgcaga aactgcaaac tgaatgcaat   720
aaagtcattg atttactgat caaaacgggc gtattccgcg gcctgaaaac tgtcctccat   780
tatatggatg tcgtttctgt gccgctgtgc cgcaaaccgt ttggaccggt agatgaaaaa   840
tatcagccag aactgaaggc gctggcccag cagttgatgc mgagcgcggg tga          893

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
ggtatccatg gcaacgaatt tacg                                          24

<210> SEQ ID NO 30
<211> LENGTH: 23
<212> TYPE: DNA
<213> ORGANISM: Artificial Sequence
<220> FEATURE:
<223> OTHER INFORMATION: primer

<400> SEQUENCE: 30
ggtaggctcg agcgagggga aac                                           23

<210> SEQ ID NO 31
<211> LENGTH: 663
<212> TYPE: DNA
<213> ORGANISM: Escherichia coli

<400> SEQUENCE: 31

```
atgaagacat acaagattgc cgttgatggg cctgctgcga gcggaaaaag cagcacatcc    60
gacttggttg caaggaaact ggggttttcc catctgatat ctggaaatct gtatagagct   120
gtgacatatg gtctggtaag gcgctttgga gaggtgcgtc caggagacga ggaacagaaa   180
agatttgttc ttgagctgag tatagaggta aggaacaaca gggtattcct agacggagag   240
gacgtgtcgg agagcctccg taaggaggtg gtcgaccgcc acgttgtttc tgttgcaagg   300
gagaaatata tccgggaaaa agtgtttaca attcagaggt cggtgataga ccttgagaag   360
agggaatag ttgtggatgg aagagatata gccaccagga taatgccaaa tgcagatctg   420
aaggtgtttc ttacagcaag cccggagacg agggccagaa aagatacat ggaaggcggg    480
tctgagtcct acgaggaact gctcgagtcc ataaaaaaaa gagatcacaa cgatagaaca   540
agggagcatg atccccttgt tgccacctgc gattctattg ttatcgaaaa tgacagcatg   600
acattggagg aaacagccga cgaaatcata aggctcttca aagagtaga gtcttttaat   660
taa                                                                  663
```

<210> SEQ ID NO 32
<211> LENGTH: 29
<212> TYPE: DNA
<213> ORGANISM: Artificial Sequence
<220> FEATURE:
<223> OTHER INFORMATION: primer

<400> SEQUENCE: 32

```
catatgacgg caattgcccc ggttattac                                       29
```

<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33

```
gaattcggtc gcttatgcga gagcc                                           25
```

<210> SEQ ID NO 34
<211> LENGTH: 1203
<212> TYPE: DNA
<213> ORGANISM: Escherichia coli

<400> SEQUENCE: 34

```
atgtcgagta agttagtact ggttctgaac tgcggtagtt cttcactgaa atttgccatc    60
atcgatgcag taaatggtga agagtacctt tctggtttag ccgaatgttt ccacctgccc   120
gaagcacgta tcaaatggaa aatggacggc aataaacagg aagcggcttt aggtgcaggc   180
gccgctcaca gcgaagcgct caactttatc gttaatacta ttctggcaca aaaaccagaa   240
ctgtctgcgc agctgactgc tatcggtcac cgtatcgtac acggcggcga aaagtatacc   300
agctccgtag tgatcgatga gtctgttatt cagggtatca agatgcagc ttcttttgca    360
ccgctgcaca cccggctca cctgatcggt atcgaagaag ctctgaaatc tttcccacag    420
ctgaaagaca aaaacgttgc tgtatttgac accgcgttcc accagactat gccggaagag   480
tcttacctct acgccctgcc ttacaacctg tacaaagagc acggcatccg tcgttacggc   540
gcgcacggca ccagccactt ctatgtaacc caggaagcgg caaaaatgct gaacaaaccg   600
```

```
gtagaagaac tgaacatcat cacctgccac ctgggcaacg gtggttccgt ttctgctatc    660
cgcaacggta atgcgttga cacctctatg ggcctgaccc cgctggaagg tctggtcatg    720
ggtacccgtt ctggtgatat cgatccggcg atcatcttcc acctgcacga caccctgggc    780
atgagcgttg acgcaatcaa caaactgctg accaaagagt ctggcctgct gggtctgacc    840
gaagtgacca gcgactgccg ctatgttgaa gacaactacg cgacgaaaga agacgcgaag    900
cgcgcaatgg acgtttactg ccaccgcctg gcgaaataca tcggtgccta cactgcgctg    960
atggatggtc gtctggacgc tgttgtattc actggtggta tcggtgaaaa tgccgcaatg   1020
gttcgtgaac tgtctctggg caaactgggc gtgctgggct ttgaagttga tcatgaacgc   1080
aacctggctg cacgtttcgg caaatctggt ttcatcaaca aagaaggtac ccgtcctgcg   1140
gtggttatcc caaccaacga agaactggtt atcgcgcaag acgcgagccg cctgactgcc   1200
tga                                                                 1203

<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
catatgtcga gtaagttagt ttctg                                          25

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
gaatcctcag gcagtcaggc ggctcgcgtc                                     30

<210> SEQ ID NO 37
<211> LENGTH: 687
<212> TYPE: DNA
<213> ORGANISM: Neisseria meningitidis

<400> SEQUENCE: 37
atggaaaaac aaaatattgc ggttatactt gcgcgccaaa actccaaagg attgccatta     60
aaaaatctcc ggaaaatgaa tggcatatca ttacttggtc atacaattaa tgctgctata    120
tcatcaaagt gttttgaccg cataattgtt tcgactgatg gcgggttaat tgcagaagaa    180
gctaaaaatt tcggtgtcga agtcgtccta cgccctgcag agctggcctc cgatacagcc    240
agctctattt caggtgtaat acatgcttta gaaacaattg gcagtaattc cggcacagta    300
accctattac aaccaaccag tccattacgc acaggggctc atattcgtga agctttttct    360
ctatttgatg agaaaataaa aggatccgtt gtctctgcat gcccaatgga gcatcatcca    420
ctaaaaaccc tgcttcaaat caataatggc gaatatgccc ccatgcgcca tctaagcgat    480
ttggagcagc ctcgccaaca attacctcaa gcatttaggc ctaatggtgc aatttacatt    540
aatgatactg cttcactaat tgcaaataat tgttttttta tcgccccaac caaactttat    600
attatgtctc atcaagactc tatcgatatt gatactgagc ttgatttaca acaggcagaa    660
aacattctta atcacaagga aagctaa                                       687
```

```
<210> SEQ ID NO 38
<211> LENGTH: 27
<212> TYPE: DNA
<213> ORGANISM: Artificial Sequence
<220> FEATURE:
<223> OTHER INFORMATION: primer

<400> SEQUENCE: 38
aagcatatgg aaaaacaaaa tattgcg                                         27

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
gtggaattct tagctttcct tgtg                                            24
```

METHOD FOR PREPARING SIALIC ACID DERIVATIVE

CROSS-REFERENCE TO RELATED APPLICATIONS

This application is a U.S. national phase under the provisions of 35 U.S.C. §371 of International Patent Application No. PCT/KR14/04823 filed May 30, 2014, which in turn claims priority of Korean Patent Application No. 10-2013-0062733 filed May 31, 2013. The disclosures of such international patent application and Korean priority patent application are hereby incorporated herein by reference in their respective entireties, for all purposes.

TECHNICAL FIELD

The present invention relates to a method for preparing a sialic acid derivative characterized by performing both of a process for preparing CMP-N-acetylneuraminic acid (CMP-NeuAc) from N-acetyl-D-glucosamine (GlcNAc) and a process for preparing the sialic acid (neuraminic acid) derivative comprising combining of a sialic acid with a derivative including galactose such as lactose, or the like, together, in one reactor.

BACKGROUND ART

Sugar, which is one of biomolecule that is the most widely and abundantly present in nature, is the most common molecule involved in recognition and signaling in cell. Most sugar constituent units may be added to the aglycon, when being activated by nucleic acids. Nucleotide-sugar has an activated form of monosaccharide, and serves as a donor in a transglycosylation reaction by glycosyltransferase. However, the transglycosylation still has problems in that reactivity of the glycosyltransferase is weak, utilization of activated glycan constituent units is limited, and the like.

Recently, as research into a structure and function of sugar chain has been rapidly conducted, usage development of the sugar chain as drug or functional material including oligosaccharide, sugar lipids, glycoproteins, and the like, having physiological activities has been actively conducted. Among them, a sialic acid-containing sugar chain containing N-acetylneuraminic acid (NeuAc) at the end is a sugar chain having important functions as cell adhesion or a role as an acceptor in virus infection, and the like.

The sialic acid-containing sugar chain is generally synthesized by catalysis of sialyltransferase. The sialyltransferase is an enzyme transferring sialic acid to acceptors such as a sugar chain, and the like, using CMP-N-acetylneuraminic acid as a sugar supplier. However, practically, CMP-N-acetylneuraminic acid used as the sugar supplier is significantly expensive and only a small amount corresponding to a reagent level is supplied.

As a method for preparing CMP-N-acetylneuraminic acid, a synthesis method by CMP-N-acetylneuraminic acid synthetase enzyme, using cytidine 5'-triphosphate (CTP) and N-acetylneuraminic acid (NeuAc) as substrates, has been known. However, since CTP and NeuAc are expensive raw materials, CMP-N-acetylneuraminic acid to be synthesized by directly using the raw materials is also expensive.

As a method for preparing CMP-N-acetylneuraminic acid (CMP-NeuAc), the following methods have been reported: (1) a method for preparing CMP-NeuAc from N-acetyl-D-mannosamine (ManNAc) using N-acetylneuraminic acid lyase or N-acetylneuraminic acid synthetase (*J. Am. Chem. Soc.*, 110:6481, 1988; *J. Am. Chem. Soc.*, 110:7159, 1988; Japanese Patent Laid-Open Publication No. Hei 10-4961), (2) a method for preparing N-acetylneuraminic acid (NeuAc) by converting N-acetyl-D-glucosamine (GlcNAc) into N-acetyl-D-mannosamine (ManNAc) under alkaline conditions and adding N-acetylneuraminic acid lyase or N-acetylneuraminic acid synthetase thereto (Japanese Patent Laid-Open Publication No. Hei 5-211884; Biotechnol. Bioeng., 66:2, 1999; Enzyme Microb. Technol., 20, 1997), (3) a method for preparing NeuAc from N-acetyl-D-glucosamine (GlcNAc) using N-acetylglucosamine (GlcNAc) 2-epimerase catalyzing conversion from GlcNAc into ManNAc, N-acetylneuraminic acid lyase or N-acetylneuraminic acid synthetase (WO 95/26399; Japanese Patent Laid-Open Publication No. Hei 3-180190; Japanese Patent Laid-Open Publication No. 2001-136982), (4) a method for synthesizing CMP-N-acetylneuraminic acid using *E. coli* and yeast cells, and the like.

However, the method (1) has a problem in that N-acetyl-D-mannosamine (ManNAc) is expensive raw material, and the method (2) has a problem in that a process for purifying ManNAc from a mixture of GlcNAc and N-acetyl-D-mannosamine (ManNAc) is extremely complicated even though N-acetyl-D-glucosamine (GlcNAc) is a cheap raw material. In addition, since GlcNAc2-epimerase used in the method (3) requires ATP (adenosine triphosphate), the method (3) has problems in that it is required to add expensive ATP or produce ATP from ATP precursor, adenine, using microorganism. The method (4) has a problem in that the use of *Escherichia coli* (*E. coli*) and yeast cells is complicated in view of process.

Korean Patent Laid-Open Publication No. 10-2006-0010706 discloses a method for preparing CMP-N-acetylneuraminic acid by adding cytidine 5'-monophosphate (CMP), N-acetyl-D-glucosamine, pyruvate (sodium pyruvate) and a yeast to a transformant into which a co-expression vector including a gene encoding N-acetylglucosamine-2-epimerase and a gene encoding N-acetylneuraminic acid aldolase is introduced to thereby synthesize neuraminic acid, and further adding a CMP-N-acetylneuraminic acid synthetase, or adding cytidine 5'-monophosphate (CMP), N-acetyl-D-glucosamine, pyruvate and a yeast to a transformant into which a co-expression vector including a gene encoding N-acetylneuraminic acid aldolase and a gene encoding CMP-N-acetylneuraminic acid synthetase is introduced. However, the method has problems in that various steps need to be performed in preparing CMP-N-acetylneuraminic acid, and a conversion yield from cytidine 5'-monophosphate (CMP) used as a substrate into cytidine 5'-triphosphate (CTP) is low.

Glycans including sialyl oligosaccharides and fucose in glycoproteins and glycolipids play a significantly important role in biological processes in various ways.

However, the conventional known reactions for combining sialic acid with derivatives of biologically active materials have disadvantages in that the sialyl acid derivatives are prepared by sialyltransferase, using expensive CMP-N-acetylneuraminic acid as a starting material, and the preparation efficiency is also low. Further, technology for preparing sialic acid derivative using N-acetyl-D-glucosamine as a starting material has disadvantages in that preparation efficiency of the sialic acid derivative is low since activity range and activity of the sialyltransferase are reduced (Kim, Dae-Hee, Sun Moon graduate School of Science doctoral dissertation, 2011).

Accordingly, the present inventors made an effort to develop a method for preparing a sialic acid derivative of a biologically active material at a high efficiency and a low cost, found that when a step of preparing CMP-N-acetylneuraminic acid using N-acetyl-D-glucosamine and cytidine 5'-monophosphate (CMP) as starting materials and a step of preparing a biologically active material derivative combined with sialic acid from the prepared CMP-N-acetylneuraminic acid are performed in a single reactor, using a sialyltransferase mutant, cytidine 5'-monophosphate (CMP) which is expensive raw material, is capable of being recycled, and a sialic acid derivative of the biologically active material is capable of being prepared at a high yield, and completed the present invention.

DISCLOSURE

Technical Problem

An object of the present invention is to provide a method for preparing a sialic acid derivative at a high yield and a low cost.

In order to achieve the object, the present invention provides a method for preparing a sialic acid derivative comprising: (a) preparing a sialic acid derivative of a compound including sialyllactose or galactose residues by adding a compound including cytidine 5'-monophosphate (CMP), acetyl phosphate, nucleotide triphosphate (NTP), N-acetyl-D-glucosamine (GlcNAc), Sodium pyruvate, and galactose residues as substrates, and reacting a reaction solution including cytidine 5'-monophosphate kinase (CMK), acetate kinase (ACK), CMP-N-acetylneuraminic acid synthetase (CMP-NeuAc synthetase: NEU), N-acetylglucosamine-2-epimerase (GlcNAc-2-epimerase: NANE), N-acetylneuraminic acid aldolase (NeuAc aldolase, NAN) and sialyltransferase in a single reactor; and (b) obtaining the prepared sialic acid derivative of the compound including sialyllactose or galactose residues prepared according to the step (a).

Other features and exemplary embodiments of the present invention will become apparent from the following detailed description and the accompanying claims.

DESCRIPTION OF DRAWINGS

FIG. 2(a) shows results under pH 4.5 to 6.0, and FIG. 2(b) shows results under pH 6.5 to 7.0.

BEST MODEL

Figure 1:
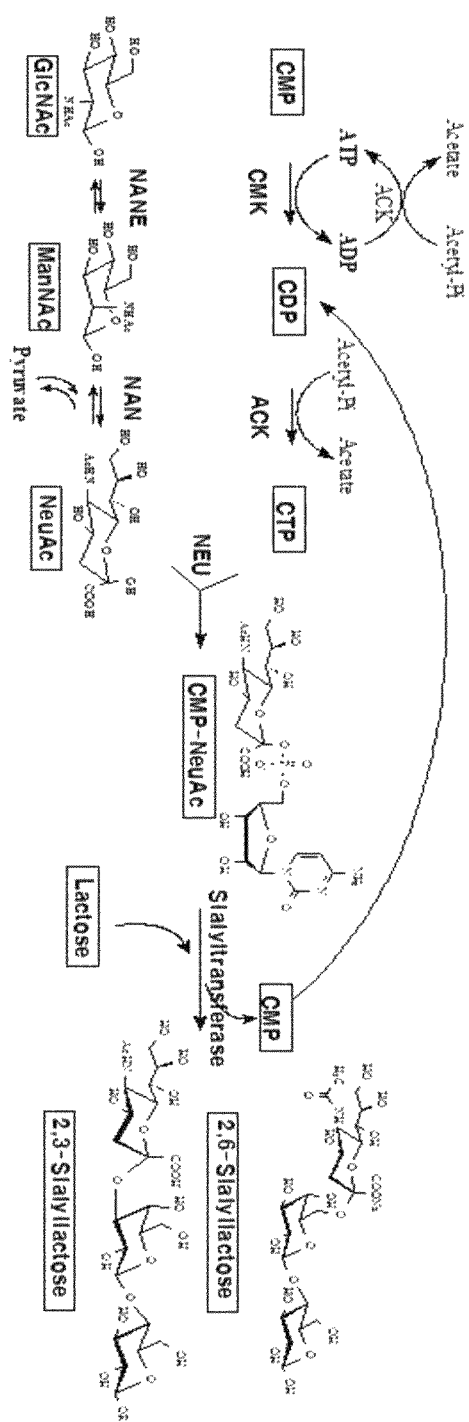
FIG. 1 shows a synthesis process for preparing 2,3-sialyllactose and 2,6-sialyllactose by one-pot reaction (integrated batch type) according to an exemplary embodiment of the present invention.

As far as it is not defined in other ways, all technical and scientific terms used in the present specification have the same meaning as being generally appreciated by those skilled in the art to which the present invention pertains. In general, the nomenclature used in the present specification is well known in technical fields and generally used.

The present invention provides a method for preparing a sialic acid derivative comprising: (a) preparing a sialic acid derivative of a compound including sialyllactose or galactose residues by adding a compound including cytidine 5'-monophosphate (CMP), acetyl phosphate, nucleotide triphosphate (NTP), N-acetyl-D-glucosamine (GlcNAc), Sodium pyruvate, and galactose residues as substrates, and reacting a reaction solution including cytidine 5'-monophosphate kinase (CMK), acetate kinase (ACK), CMP-N-acetylneuraminic acid synthetase (CMP-NeuAc synthetase: NEU), N-acetylglucosamine-2-epimerase (GlcNAc-2-epimerase: NANE), N-acetylneuraminic acid aldolase (NeuAc aldolase, NAN) and sialyltransferase in a single reactor; and (b) obtaining the prepared sialic acid derivative of the compound including sialyllactose or galactose residues prepared according to the step (a).

According to the method for preparing the sialic acid derivative of the present invention, cytidine 5'-monophosphate (CMP) which is an expensive substrate may be recycled and the sialic acid derivative may be prepared at a high yield by performing both of a process for preparing CMP-N-acetylneuraminic acid from N-acetyl-D-glucosamine and a process for preparing the sialic acid (neuraminic acid) derivative that combines a sialic acid with a derivative including galactose, together, in one reactor.

The conventional method for preparing the sialic acid derivative is a process for combining a sialic acid with a derivative including lactose or galactose by sialyltransferase, using CMP-N-acetylneuraminic acid as a starting material. However, since the CMP-N-acetylneuraminic acid is significantly expensive material, a large amount of cost is consumed in preparing the sialic acid derivative.

In order to solve the problems, the present inventors developed a method for preparing CMP-N-acetylneuraminic acid at a high yield using cytidine 5'-monophosphate (CMP) and a trace amount of NTP, and various substrates and enzymes while utilizing novel N-acetylglucosamine-2-epimerase enzyme derived from *bacteroides fragilis* NCTC 9343 (Korean Patent No. 0888513).

When CMP-N-acetylneuraminic acid and lactose react with sialyltransferase, the sialic acid is transferred to the lactose, thereby preparing sialyllactose and cytidine 5'-monophosphate (CMP). In the conventional method for preparing sialyllactose, the process for preparing CMP-N-acetylneuraminic acid using cytidine 5'-monophosphate (CMP) as a substrate and the process for transferring the sialic acid, are performed in different reactors, respectively, and accordingly, cytidine 5'-monophosphate (CMP) to be prepared, could not be recycled.

In the present invention, since the process for preparing CMP-N-acetylneuraminic acid from cytidine 5'-monophosphate (CMP) and the process for preparing the sialic acid derivative and cytidine 5'-monophosphate (CMP) in a derivative including CMP-N-acetylneuraminic acid and galactose such as lactose, or the like, by sialyltransferase, are performed in the same reactor, cytidine 5'-monophosphate (CMP) prepared by the sialic acid transfer reaction, may be recycled in the process for preparing CMP-N-acetylneuraminic acid.

FIG. 1 shows a synthesis process for preparing 2,3-sialyllactose and 2,6-sialyllactose in a single reactor according to an exemplary embodiment of the present invention.

In an exemplary embodiment of the present invention, sialyllactose is prepared from N-acetyl glucosamine (GlcNAc), pyruvate (sodium pyruvate), cytidine 5'-monophosphate (CMP), and the like, which are cheap substrate in vitro, by one-pot reaction. A conversion rate of sialyllactose at a preparation rate of CMP-N-acetylneuraminic acid (7.5 mM/hr to 8.5 mM/hr) is 650% based on cytidine 5'-monophosphate (CMP) and 81% based on N-acetyl-D-glucosamine (GlcNAc). A purification yield of sialyllactose having purity of 98% or more is 75%. Preparation of sialyllactose by a reusing system of cytidine 5'-monophosphate (CMP) in situ was performed successfully using a cell extract enzyme.

In another aspect of the present invention, upon comparing the method for preparing sialyllactose by one-pot reaction according to the present invention with the conventional method for preparing sialyllactose by two-pot reaction, it was confirmed that in the method for preparing sialyllactose by one-pot reaction according to the present invention, an amount of sialyllactose was doubled even though a concentration of cytidine 5'-monophosphate (CMP) to be added is reduced to 1/5 (Table 4).

In the present invention, sialyltransferase may be α-2,3-sialyltransferase, α-2,6-sialyltransferase, or α-2,8-sialyltransferase, preferably, 2,3-sialyltransferase or 2,6-sialyltransferase.

In an exemplary embodiment of the present invention, in order to develop sialyltransferase having high activity even under the same activity condition with cytidine 5'-monophosphate kinase (CMK), acetate kinase (ACK), NeuAc aldolase (NAN), CMP-NeuAc synthetase (NEU), and GlcNAc-2-epimerase (NANE) which are enzymes involved in preparation of CMP-N-acetylneuraminic acid, a mutant enzyme having high activity under the same condition as other enzymes was developed by mutating α-2,3-sialyltransferase derived from *Pasteurella multocida* and α-2,6-sialyltransferase derived from *Photobacterium damselae*. The α-2,3-sialyltransferase derived from *Pasteurella multocida* has the amino acid sequence of SEQ ID NO: 1. An R289 α-2,3-sialyltransferase mutant derived from the *Pasteurella multocida* amino acid sequence of SEQ ID NO: 1 has the amino acid sequence of SEQ ID NO: 2. More generally, α-2,3-sialyltransferase mutants usefully employed in accordance with the present disclosure may comprise N, H, T or Y substitution from R in the 289th amino acid of α-2,3-sialyltransferase having an amino acid sequence of SEQ ID NO:1 or N or S substitution from T in the 241st amino acid of α-2,3-sialyltransferase having an amino acid sequence of SEQ ID NO:1. In specific embodiments, the α-2,3-sialyltransferase mutant has an amino acid sequence represented by one selected from the group consisting of SEQ ID Nos: 2-6. In this respect, it is noted that R313 mutant substitutions referred to hereinafter are to be understood as R289 mutant substitutions derived from α-2,3-sialyltransferase having an amino acid sequence of SEQ ID NO:1, and that T265 mutant substitutions referred to hereinafter are to be understood as T241 mutant substitutions derived from α-2,3-sialyltransferase having an amino acid sequence of SEQ ID NO:1.

Therefore, α-2,3-sialyltransferase of the present invention is characterized by a mutant enzyme of α-2,3-sialyltransferase having any one amino acid sequence of SEQ ID NOS: 2 to 6, and α-2,6-sialyltransferase of the present invention is characterized by a mutant enzyme of α-2,6-sialyltransferase having any one amino acid sequence of SEQ ID NOS: 14 to 18.

Preferably, the method for preparing the sialic acid derivative according to the present invention is performed at 25 to 38° C. in view of activity temperature of each enzyme involved in the reaction, and at pH 7 to 9 in view of activity pH of each enzyme involved in the reaction.

In the present invention, as GlcNAc-2-epimerase, NANE, an enzyme having amino acid sequence of SEQ ID NO: 25 which is N-acetylglucosamine-2-epimerase enzyme derived from *bacteroides fragilis* NCTC 9343 is preferably used, but the present invention is not limited thereto.

In the present invention, the compound including the galactose residue may be a derivative including galactose of a compound selected from the group consisting of monosaccharides, oligosaccharides, linkers, flavonoids, anti-cancer agents, antibiotics, immunosuppressants and antibodies.

In the present invention, the monosaccharide may be glucose, N-acetyl-D-glucosamine, mannose, and the like, the linker may be a functional group which is linkable using ester or amide bond, for example, the linker means a linker capable of linking formyl, acetyl group, propionyl group, butyl group, acryl group, ethylsuccinyl group, succinyl group, aminohexyl group, and the like.

A mutant of α-2,6-sialyltransferase used in the present invention is derived from *Photobacterium damselae* strain and is included in GT family 80 as the same as 2,6-sialyltransferase derived from *Pasteurella* genus in view of structure folding and sequence of glycosyltransferase. Even in α-2,6-sialyltransferase derived from *Photobacterium*, an activity of α-2,6-sialyltransferase and sialyltransferase was recently revealed, but since the activity of the side-reaction is significantly smaller than that of the transference activity (150 times or more) of 2,6-sialic acid, it is regarded that most of the activity is the transference activity of 2,6-sialic acid. α-2,6-sialyltransferase has advantages in that the side reaction rarely occurs, most of the activity is the transference activity of 2,6-sialic acid, and substrate specificity is various, but has disadvantages in that difference in enzyme activity is low by 5 to 6 times as compared to α-2,3-sialyltransferase derived from *Pasteurella*.

In order to increase preparation efficiency of various sialyl oligosaccharides having 2,3 and 2,6 combinations, it is required to produce mutants in which functions of α-2,3 and α-2,6 sialyltransferases having various substrate specificities as defined above are improved, and to utilize the mutants for production of sialyl oligosaccharides.

Biosynthesis of CMP-N-acetylneuraminic acid which is a sialic acid donor of sialyltransferase by five enzymes has the best productivity at neutral pH. Meanwhile, the sialic acid transfer reaction by α-2,3-sialyltransferase has the best reactivity at pH 8 to 9. That is, α-2,3-sialyltransferase has activity at a wide range of pH, but the activity is resulted from multi-functional characteristics showing side reaction below neutral pH. Since 2,3-sialic lactose is additionally prepared by α-2,3-sialyltransferase below neutral pH, two steps of reaction including a step of preparing CMP-N-acetylneuraminic acid at neutral pH and converting pH of a buffer solution to pH 8 to 9, and a step of applying α-2,3-sialyltransferase are performed in the conventional reaction. Accordingly, α-2,3-sialyltransferase may inhibit production of the side-reaction, thereby performing integrated batch type reaction, and rapidly performing a catalytic reaction, whereby productivity and efficiency of various 2,3-sialyl derivatives including 2,3-sialyllactose may be improved.

In order to produce mutants of sialyltransferase in the present invention, a hybrid method, that is, a semi-rational method was used. The hybrid method is a combination of directed evolution and rational design, having an object of securing only a small number of mutant libraries in good quality. The hybrid method refers to perform the mutation by analyzing a target portion of protein and selecting specific amino acid residues using sequences, structures, and functions of protein, and computer programs.

In the present invention, sialyltransferase, which is Leloir glycosyltransferase, indicates an enzyme transferring N-acetylneuraminic acid to an acceptor sugar material from CMP-N-acetylneuraminic acid. Lactose which is an acceptor substrate is oligosaccharide consisting of Galβ1,4Glc (galactose and glucose are bound with each other by β1,4 bond).

2,3-sialyl oligosaccharide and 2,6-sialyl oligosaccharide mean oligosaccharides in which N-acetylneuraminic acid (sialic acid) is bound to galactose portion by a2,3 or a2,6 bond, and other sugars may be further bound to the galactose or glucose. 2,3- and 2,6-sialyllactose means triose consisting of Neu5Aca2,3/2,6Galβ,4Glc (sialic acid is bound to galactose of lactose by α-2,3 or α-2,6 bond).

In the present invention, whole cell reaction means a reaction using cell contents by disrupting the cells including specific enzyme or using total of whole cells without separating and purifying the enzyme. The reaction of the present invention may be performed in the manner of the whole cell reaction, and may be performed by independently adding each purified enzyme, and by purifying each enzyme and fixing each enzyme in a bead form.

In the present invention, site directed mutagenesis refers to introduction of changes in nucleotide sequence defined at the designated location of a gene, and saturation mutagenesis refers to introduction of changes in various base sequences at the designated location of a gene. The saturation mutagenesis refers to introduction of mutation through PCR by inserting NNK codon on a primer having complimentary sequence to be bound to a template strand, instead of sequence to be mutated. Here, in the NNK codon, N means A, T, G, C of nucleotide, and K means T, G.

The vector means a polynucleotide consisting of single-stranded, double-stranded, circular or supercoiled DNA or RNA, and may include components which are operably linkable at an appropriate distance to produce a recombinant protein.

The components may include replication origin, promoter, enhancer, 5'mRNA leader sequence, ribosomal binding site, nucleic acid cassette, termination and polyadenylation sites, or selectable label format, and the like, and one or more of the components may be omitted depending on specific applications. The nucleic acid cassette may include a restriction enzyme site for inserting recombinant protein to be expressed. In a functional vector, the nucleic acid cassette may contain a nucleic acid sequence to be expressed, including translation initiation and termination region, and vectors capable of inserting the two types of cassettes into the vector are used as needed, and the above-mentioned functions may be additionally sequenced.

Genes inserted into the recombinant vector may be *E. coli* for expression, such as BW25113 (DE3), BL21 (DE3), and the like, but may vary depending on the type of the inserted vectors. The vectors and expression strains may be easily selected by a person skilled in the art.

According to another embodiment of the present invention, Lewis X could be successfully obtained using LacNAc as a lactose derivative. According to the prevent invention, various functional oligosaccharides such as sialyl Lewis X(SLeX) may be prepared.

According to still another embodiment of the present invention, in order to synthesize sialyl vancomycin derivatives, enzymatic approach using two glycosyltransferases, β1,4-GalT and α-2,3-SiaT was used, and the combination of galactose and sialic acid at the vancomycin portion and the glucose portion of pseudo-vancomycin was proven. Further, as the MIC test result, the antibiotic activity against MRSA and VSEF of derivatives including galactose was higher than or equal to that of the derivative including galactose/sialic acid. The sialyltransferase having the relaxed substrate specificity according to the present invention may be applied to sialylation of small molecules in nature bound with other glycopeptide antibiotics or sugars such as polyketide or nonribosomal peptide.

EXAMPLE

Hereinafter, the present invention will be described in detail with reference to the following Examples. However, the following examples are only for exemplifying the present invention, and it will be obvious to those skilled in the art that the scope of the present invention is not construed to be limited to these examples.

Example 1

Preparation of Mutants of Sialyltransferase

In α-2,3-sialyltransferase used in the present invention, a substrate binding pocket portion was confirmed from a crystal structure, and in 2,6-sialyltransferase used in the present invention, a substrate binding pocket portion was confirmed from a model structure having a crystal structure of α-2,6-sialyltransferase derived from other *Photobacterium* as a template. Residues positioned within 5~20 Å from CMP-N-acetylneuraminic acid and an acceptor substrate were selected from each of α-2,3 sialyltransferase and 2,6-sialyltransferase.

The wild-type α-2,3-sialyltransferase used in the present invention is derived from *Pasteurella multocida* (ATCC15742) and the wild-type α-2,6-sialyltransferase is derived from *Photobacterium damselae* (ATCC29690).

In the present invention, multiple sequence alignment using the sequence information of bioinformatics was performed while excluding residues preserving amino acid residues at a specific position in the protein structure, as mutation residues. In order to select functional residues to perform saturation mutagenesis among the residues selected as above in the substrate-binding residues, site directed mutagenesis was performed with alanine. The substitution with alanine may interpret whether a specific residue contributes to an important catalyst activity due to action with the substrate, like removal of the residue. After the substitution with alanine, enzyme activity was measured by colorimetry and compared with wild type strain in view of activity difference.

Further, in the present invention, alanine substitution mutants maintaining the folding degree of protein as compared to the wild type strain, were selected. Consequently, in the alanine substitution mutants of each of α-2,3 and α-2,6-sialyltransferase, residues showing activity of at least 30%, preferably at least 50%, and more preferably at least 60% as compared to the wild type strain, and maintaining the folding of protein were selected as functional residues to perform the saturation mutagenesis which is a next step.

By performing the saturation mutagenesis on the residues of the alanine substitution mutants maintaining the folding of the enzyme and original activity while leaving residues essentially contributing to interaction with the substrate, that is, contributing to main activity of the sialic acid transfer in the catalytic reaction, neutral drift of the enzyme is capable of being induced to produce an enzyme-substrate complex in an active form which is more properly fitted to the substrate through the saturation mutagenesis as compared to the wild type strain.

1-1: Performance of Saturation Mutagenesis on Functional Residues of Sialyltransferase and Search of Mutants The entire vector was subjected to PCR using a primer into which NNK sequence (a sequence where N is A, C, G or T, K is G or T) is introduced, the NNK sequence obtained by randomly replacing AGA and ACC sequences corresponding to amino acid positions 313 and 265 of α-2,3-sialyltransferase, thereby constructing a library. Since α-2,3-sialyltransferase of the present invention has a form in which 24 amino acids are removed at N-terminal, the amino acid at $25^{th}$ position from the first methionine sequence is methionine.

The entire vector was subjected to PCR using a primer into which NNK sequence (a sequence where N is A, C, G or T, K is G or T) is introduced, the NNK sequence obtained by randomly replacing ATT and CTG sequences corresponding to amino acid positions 411 and 433 of α-2,6-sialyltransferase, thereby constructing a library. In α-2,6-sialyltransferase of the present invention, methionine is the first amino acid when counting from the first methionine sequence. In order to remove the original plasmid, the amplified gene of the sialyltransferase including the vector sequence was treated with Dpn enzyme and transformed into *E. coli* DH5α. Mutant genes were extracted from all of generated colonies and transformed into *E. coli* BW25113 (DE3). The transformed individual colonies were inoculated in the LB medium (500 μL) containing ampicillin in 96 well and shake-cultured at 30 to 37° C. for 18 to 24 hours, and then some of the culture liquid was inoculated in new LB medium (500 μL) containing 100 μg mL$^{-1}$ ampicillin and IPTG and cultured at 18 to 30° C. for 18 to 40 hours. The cultured cells were centrifuged and re-suspended in 1~10 mM Tris buffer (100 μL). Then, among them, whole cells (10 μL) were used for the mutant search reaction, or cells (50 μL) were re-suspended with BugBuster protein extraction reagent, followed by centrifugation to obtain a cell extract, and then, some of the cell extract (10 μL) was used for a mutant search reaction. The reaction proceeded while simultaneously adding the whole cell (10 μL) or cell extract (10 μL) to a reaction solution (90 μL) containing 1~10 mM Tris buffer, 1~5 mM CMP-N-acetylneuraminic acid and lactose and 0.1~1 mM pH indicator, and the reaction rate for 10 to 30 minutes at a time interval of one minute was observed as compared to the wild type strain.

The wild type strain and mutants of sialyltransferase transformed into *E. coli* BW25113 (DE3) were expressed using the inducer IPTG in a culture volume of 50 mL, and purified to obtain only pure protein using Ni-NTA column, and specific activity and kinetic parameters were measured.

Specific activities of single amino acid substitution mutants of α-2,3- and α-2,6-sialyltransferase were analyzed through enzyme activity analysis method using the pH indicator with the same amount of each protein, and were calculated as activity (unit) per enzyme (mg) when conversion yield of 10 to 25% relative to the initial acceptor substrate concentration is exhibited by performing the reaction for 5-10 minutes, and the results were shown in Table 1.

The saturation mutagenesis was performed on the selected functional residues of α-2,3-sialyltransferase, through PCR using NNK codon, and screened through colorimetry using a pH indicator on the mutant libraries.

Mutants in which change in absorbance over time is increased as compared to the wild type strain, were primarily searched, and the mutants were cultured to obtain cell extract. Then, in the cell extract, an initial reaction rate was calculated by unit per volume (mL) of cell extract.

In the mutants of α-2,3-sialyltransferase, the arginine of R313 is positioned on a loop near glucose of lactose. For the mutants of R313, the mutants substituted with amino acids having small size such as alanine and glycine exhibited neutral activity as compared to the wild type strain, and the mutants substituted with hydrophilic amino acids such as serine, threonine, tyrosine, aspartic acid, asparagine, histidine exhibited activity 1.5 times higher than that of the wild type strain.

For the mutants of T265 positioned within 20 Å of the CMP-N-acetylneuraminic acid, it was observed that the mutants substituted with glycine, serine, and asparagine exhibited activity similar to or higher than that of the wild type strain.

As a result obtained by comparing the mutants of R313 with the wild type strain in view of relative specific activity, R313 mutants could accept various mutants relatively, and among them, specific activity of R313N was 231% as compared to the wild type strain which was the highest among the single mutant. In addition, the relative specific activity of the mutants of T265 as compared to the wild type strain was shown in Table 1.

TABLE 1

Activity of α-2,3 and α-2,6 sialyltransferase

| 효소 (α2,3PST) | Rel. Specific Ac (%) | 효소 (α2,6PdST) | Rel. Specific Ac (%) |
|---|---|---|---|
| WT | 100 | WT | 100 |
| R313N | 231 | I411T | 198 |
| R313H | 146 | L433S | 289 |
| R313T | 129 | L433T | 296 |
| R313Y | 125 | I411T/L433S | 194 |
| R313D | 108 | I411T/L433T | 510 |
| T265N | 126 | | |
| T265S | 116 | | |
| T265G | 94 | | |
| R313N/T265S | 216 | | |
| R313H/T265S | 237 | | |

Meanwhile, similar to the selected functional residues of α-2,3-sialyltransferase, the saturation mutagenesis was performed on the selected functional residues of α-2,6-sialyltransferase through PCR using NNK codon, and screened through colorimetry using a pH indicator on the mutant libraries. I411 and L433 are positioned within 5~20 Å from the CMP-N-acetylneuraminic acid. Among the mutants of L433, L433S and L433T exhibited activity increased by 3 times compared to the wild type strain. It was observed that among the mutants of I411, I411T exhibited activity increased by 2 times compared to the wild type strain. In the wild type α-2,6-sialyltransferase, expression in pET28a vector was increased as compared to pET15b vector, and accordingly, the searched mutants were cloned in the pET28a vector and the specific activities thereof were confirmed (Table 1).

1-2: Analysis of Characterization of Mutants of α-2,3 Sialyltransferase

R313N which is the single amino acid substitution mutant of R313 of α-2,3-sialyltransferase in the present invention is a protein having amino acid sequence of SEQ ID NO: 2 and having hydrophilic amino acid sequence at 313th position, and DNA encoding the protein of SEQ ID NO: 2 has amino acid sequences of SEQ ID NO: 8, and may also include all DNA sequences encoding the amino acids.

In addition, R313H has amino acid sequence of SEQ ID NO: 3, and may include protein having hydrophilic amino acid sequence at the 313th position of the amino acid and even all enzymes having the sialic acid transfer activity with 97% or more homology including the mutant sequence. DNA encoding the protein of SEQ ID NO: 3 has amino acid sequences of SEQ ID NO: 9 and may also include all DNA sequences encoding the amino acids.

Further, T265S has amino acid sequence of SEQ ID NO: 4, and may include protein having hydrophilic amino acid sequence at the 265th position of the amino acid and even all enzymes having the sialic acid transfer activity with 97% or more homology including the mutant sequence. DNA encoding the protein of SEQ ID NO: 3 has amino acid sequences of SEQ ID NO: 10 and may also include all DNA sequences encoding the amino acids.

Further, combinatorial mutants of R313N and T265S have amino acid sequences of SEQ ID NO: 5, and combinatorial mutants of R313H and T265S have amino acid sequences of SEQ ID NO: 6. Further, the mutants may include protein having hydrophilic amino acid sequence at the 313th position and the 265th position of the amino acid and even all enzymes having the sialic acid transfer activity with 97% or more homology including the mutant sequence. DNA encoding the protein of SEQ ID NO: 5 has amino acid sequences of SEQ ID NO: 11, and DNA encoding the protein of SEQ ID NO: 6 has amino acid sequences of SEQ ID NO: 12 and may also include all DNA sequence encoding the amino acids.

Examples having homology of 97% or more with the mutants of the specified α-2,3-sialyltransferase include mutated sequence of the mutant, and may include sequences derived from *Pasteurella* genus, particularly, *multocida* species, as sequences specified or predicted as having activity of α-2,3-sialyltransferase.

Further, in the present invention, combinatorial mutants for the single amino acid substitution mutant of R313 and the single amino acid substitution mutant of T265 of α-2,3-sialyltransferase having high specific activity were constructed, and among the combinatorial mutants, R313H/T265S and R313N/T265S had high specific activity of 237% and 216%, respectively, relative to the wild type strain. In order to appreciate the effect of each mutation on the donor substrate and the acceptor substrate, kinetic parameters for a single amino acid substitution mutant and a combinatorial mutant were measured.

The measured kinetic parameters were analyzed by the mutant search method using the colorimetry, and the initial reaction rate when conversion yield of 10 to 25% relative to the substrate concentration of the initial acceptor is exhibited at an interval of every 30 seconds by performing the reaction for 5-10 minutes at room temperature, was measured. The kinetic parameters were measured on both of the two donor substrate, CMP-N-acetylneuraminic acid, and the acceptor substrate, lactose, and the substrate concentration had a range from 0.1 to 30 mM. The kinetic parameters, $k_{cat}$ and $K_m$, were obtained from nonlinear regression analysis of Michaelis-Menten equation using Sigma Plot (SigmaPlot) program. The kinetic parameters on the wild type strain and the mutants of α-2,3-sialyltransferase were shown in Table 2.

TABLE 2 kinetic parameters of α-2,3-sialyltransferase

| Enzyme (a2,3 PST) | CMP-Neu5Ac[a] | | | Lac[b] | | |
|---|---|---|---|---|---|---|
| | $k_{cat}$ (s$^{-1}$) | $K_m$ (mM) | $k_{cat}/K_m$ (s$^{-1}$ mM$^{-1}$) | $k_{cat}$ (s$^{-1}$) | $K_m$ (mM) | $k_{cat}/K_m$ (s$^{-1}$ mM$^{-1}$) |
| WT | 12.9 | 1.83 | 7.01 | 57.4 | 2.31 | 24.8 |
| R313N | 23.9 | 2.51 | 9.51 | 89.9 | 2.55 | 35.2 |
| R313H | 26.8 | 3.24 | 8.26 | 80.5 | 2.68 | 30.1 |
| T265S | 22.1 | 2.23 | 9.91 | 63.2 | 2.43 | 26.1 |
| R313N/T265S | 36.9 | 3.33 | 11.1 | 82.4 | 2.21 | 37.3 |
| R313H/T265S | 43.4 | 3.94 | 11.0 | 73.9 | 1.65 | 44.8 |

In R313N and R313H which are single amino acid substitution mutants, the $k_{cat}$ was increased with respect to CMP-N-acetylneuraminic acid and lactose, and $k_{cat}/K_m$ of R313N and R313H with respect to two substrates were increased by about 1.4 times and about 1.2 times relative to the wild type strain, respectively. In R313N/T265S and R313H/T265S which are combinatorial mutants, the $k_{cat}$ was increased with respect to the two substrates, and $k_{cat}/K_m$ of R313N/T265S and R313H/T265S with respect to CMP-N-acetylneuraminic acid was increased by about 1.6 times. Further, in R313N/T265S and R313H/T265S, $k_{cat}/K_m$ with respect to lactose were increased by about 1.5 times and about 1.8 times relative to the wild type strain, respectively.

Figure 2:
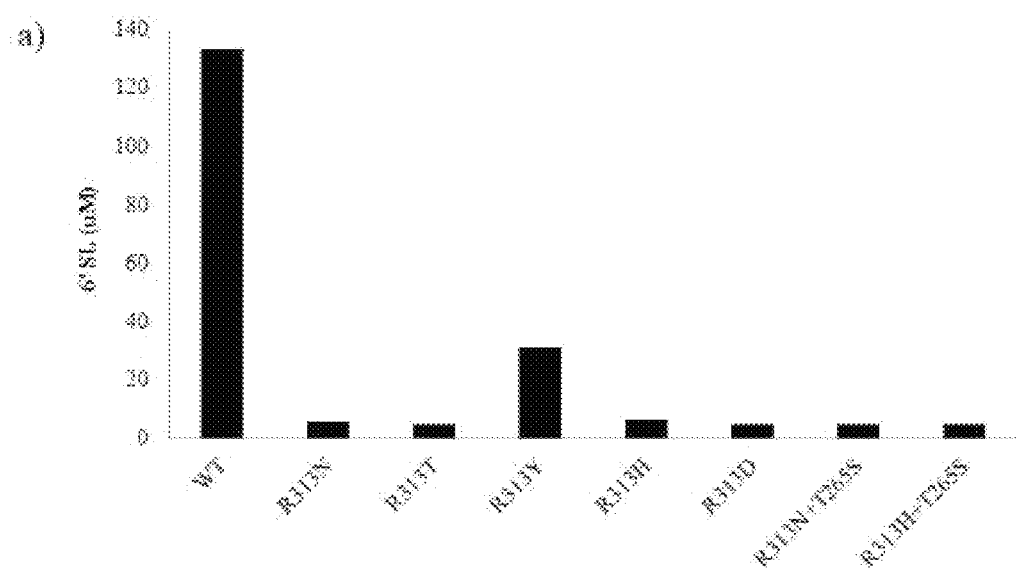
FIG. 2 shows confirmation of 2,6 sialic acid transfer side reactions of α-2,3-sialyltransferase mutants.
Figure 2:
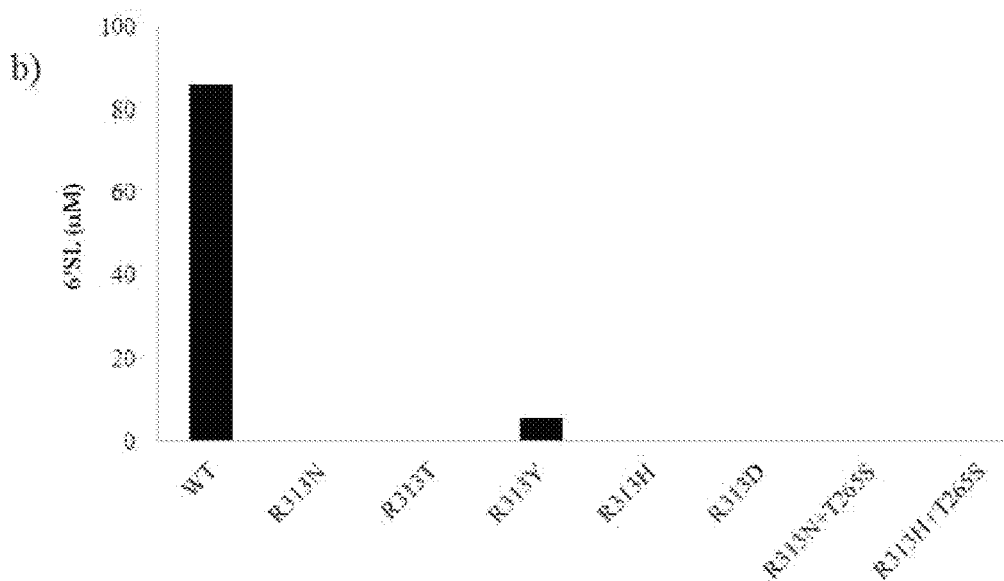

In the present invention, it was also confirmed that when replacing arginine at 313th position of amino acid of α-2,3-sialyltransferase to be converted into other hydrophilic amino acids (N, D, Y, T, H), specific activity of the enzyme was increased and 2,6-sialic acid transfer side reaction with respect to these mutants was confirmed. As results obtained by measuring 2,6-sialic acid transfer side reaction of R313N, R313D, R313Y, R313T, R313H and the combinatorial mutants, R313N/T265S and R313H/T265S at pH 4.5~7.0 at which 2,6-sialic acid transfer side reaction occurs, the production amount of 2,6-sialyllactose was reduced by 4-30 times in pH 4.5 to 6.0 (FIG. 2a) as compared to the wild type strain. At pH 6.5 to pH 7.0 (FIG. 2b), all of the production amount of 2,6-sialyllactose disappeared except for R313Y (reduced by 15 times). The results were shown in FIG. 2.

1-3: Analysis of Characterization of Mutants of α-2,6 Sialyltransferase having a small size or hydrophilic amino acid sequence at the 411th position and the 433th position of the amino acid and even all enzymes having the sialic acid transfer activity with 55% or more homology including the mutant sequence. DNA encoding the protein of SEQ ID NO: 17 has amino acid sequences of SEQ ID NO: 23, and DNA encoding the protein of SEQ ID NO: 19 has amino acid sequences of SEQ ID NO: 24 and may also include all DNA sequence encoding the amino acids.

Examples having homology of 55% or more with the mutants of the specified α-2,6-sialyltransferase include mutated sequence of the mutant, and may include sequences derived from Photobacterium genus, particularly, Photobacterium damselae, Photobacterium leiognathi species, as sequences specified or predicted as having activity of α-2,6-sialyltransferase. Further, sequences of Photobacterium Jt-Ish-224 α-2,6-sialyltransferase which is a template protein forming a protein model structure of the present invention may be included since it has a homology of 55% with α-2,6-sialyltransferase of the present invention.

In the present invention, combinatorial mutants for the single amino acid substitution mutant of I411T of α-2,6 sialyltransferase having high specific activity and the single amino acid substitution mutants of L433S and L433T were constructed, and I411T/L433S and I411T/L433T among the combinatorial mutants had high specific activity of 194% and 510%, respectively, relative to the wild type strain. In order to appreciate the effect of each mutation on the donor substrate and the acceptor substrate, kinetic parameters for a single amino acid substitution mutant and a combinatorial mutant were measured. The results were shown in Table 3.

TABLE 3 kinetic parameters for α-2,6 sialyltransferase

| Enzymes (a2,6 PdST) | CMP-Neu5Ac$^a$ | | | Lac$^b$ | | |
|---|---|---|---|---|---|---|
| | $k_{cat}$ (s$^{-1}$) | $K_m$ (mM) | $k_{cat}/K_m$ (s$^{-1}$ mM$^{-1}$) | $k_{cat}$ (s$^{-1}$) | $K_m$ (mM) | $k_{cat}/K_m$ (s$^{-1}$ mM$^{-1}$) |
| WT | 3.99 | 5.47 | 0.73 | 4.45 | 9.03 | 0.49 |
| I411T | 11.1 | 6.36 | 1.75 | 25.7 | 28.4 | 0.90 |
| L433S | 18.3 | 9.54 | 1.92 | 85.4 | 59.1 | 1.45 |
| L433T | 10.4 | 2.11 | 4.90 | 73.2 | 56.7 | 1.29 |
| I411T/L433S | 17.4 | 11.9 | 1.47 | 113 | 78.5 | 1.31 |
| I411T/L433T | 18.1 | 3.09 | 5.86 | 119 | 57.0 | 1.90 |

In the present invention, I411T which is the single amino acid substitution mutant of I411 of α-2,6-sialyltransferase has amino acid sequence of SEQ ID NO: 14, and may include protein having a small size or hydrophilic amino acid sequence at the 411th position of the amino acid and even all enzymes having activity of the sialic acid transfer with 55% or more homology including the mutant sequence. DNA encoding the protein of SEQ ID NO: 14 has amino acid sequences of SEQ ID NO: 20 and may also include all DNA sequence encoding the amino acids.

In addition, L433S has amino acid sequence of SEQ ID NO: 15, and L433T has amino acid sequence of SEQ ID NO: 16 and may include protein having hydrophilic amino acid sequence at the 433th position of the amino acid and even all enzymes having activity of the sialic acid transfer with 55% or more homology including the mutant sequence. DNA encoding the protein of SEQ ID NOS: 15 and 16 has amino acid sequences of SEQ ID NOS: 21 and 22 and may also include all DNA sequences encoding the amino acids.

Further, combinatorial mutants of I411T and L433S have amino acid sequences of SEQ ID NO: 17, and combinatorial mutants of I411T and L433T have amino acid sequences of SEQ ID NO: 18. Further, the mutants may include protein With respect to the acceptor substrate, lactose, in all mutants, the binding force with the acceptor substrate, lactose, was reduced, but $k_{cat}$ was increased from 6 times up to 27 times as compared to the wild type strain. In single mutants, I411T, L433S and L433T, $k_{cat}/K_m$ was increased by 1.8 times, 3 times and 2.6 times, respectively, and $k_{cat}/K_m$ of the combinatorial mutants, I411T/L433S and I411T/L433T, was increased by 2.7 times and 3.9 times, respectively, as compared to the wild type strain.

Meanwhile, with respect to the donor substrate, CMP-N-acetylneuraminic acid, in the single amino acid substitution mutants, I411T and L433S, $k_{cat}/K_m$ was increased by 2.4 times and 2.6 times, respectively, as compared to the wild type strain. In L433T, the affinity with the substrate was also increased, such that $k_{cat}/K_m$ was increased by 6.7 times as compared to the wild type strain. In combinatorial mutants, I411T/L433S and I411T/L433T, $k_{cat}$ was increased by 4.5 times as compared to the wild type strain, and $k_{cat}/K_m$ was increased by 2 times and 8 times, respectively, as compared to the wild type strain.

The mutants of α-2,3- and α-2,6-sialyltransferase produced by the present invention may be applied to various oligosaccharide substrates including galactose portions by including N-acetyl-lactosamine (LacNAc), azido β-D-galactopyranosyl-(1-4)-β-D-glucopyranoside (LacβN3), 3-azidopropyl β-D-galactopyranosyl-(1-4)-β-D-glucopyranoside (LacβProN3), methyl β-D-galactopyranosyl-(1-4)-β-D-glucopyranoside (LacβOMe) which are disaccharide acceptor substrate as well as the above-described lactose acceptor substrate.

Further, the mutants of α-2,3- and α-2,6-sialyltransferase produced by the present invention may be applied to various derivative substrates including CMP-deaminoneuraminic acid (CMP-KDN), CMP-N-glycolylneuraminic acid (CMP-Neu5Gc) as well as the above-described CMP-N-acetylneuraminic acid acceptor substrate.

Example 2

Preparation of Enzyme for Synthesizing CMP-N-Acetylneuraminic Acid

In order to prepare CMP-N-acetylneuraminic acid which is an intermediate material of the sialylation reaction, enzymes to be used were prepared.

The enzymes used for preparing CMP-N-acetylneuraminic acid from N-acetyl-D-glucosamine were cytidine 5'-monophosphate kinase (CMK), acetate kinase (ACK), N-acetylneuraminic acid aldolase (NeuAc aldolase: NAN), CMP-N-acetylneuraminic acid synthetase (CMP-NeuAc synthetase: NEU), and N-acetylglucosamine-2-epimerase (GlcNAc-2-epimerase: NANE) and the enzyme for preparing 2,3-sialyllactose by reacting CMP-N-acetylneuraminic acid with lactose was α-2,3-sialyltransferase, and the enzyme for preparing α-2,6-sialyllactose by reacting CMP-N-acetylneuraminic acid with lactose was α-2,6-sialyltransferase.

The method for preparing the enzymes used in preparing CMP-N-acetylneuraminic acid from N-acetyl-D-glucosamine was described in Korean Patent Laid-Open Publication No. 10-2008-0055588 in detail.

The method for preparing the enzymes was summarized briefly as follows:

(1) Preparation of N-Acetylglucosamine-2-Epimerase (GlcNAc 2-Epimerase: NANE)

In order to clone the nanE gene encoding N-acetylglucosamine-2-epimerase (GlcNAc 2-epimerase, SEQ ID NO: 25) from genome of *Bacteroides fragilis* NCTC 9343 strain, the nanE gene was amplified by PCR using chromosomal DNA of the *Bacteroides fragilis* NCTC 9343 strain as a template and using primers of SEQ ID NO: 26 and SEQ ID NO: 27.

SEQ ID NO: 26:  5'-ct gcc atg gtt atg aat act aca g

SEQ ID NO: 27:  5'-aat gga tcc tta ttt ttc tga cag

The amplified PCR product was purified, cut by restriction enzymes NcoI and BamHI, and linked to plasmid pET28a(+)(Novagen) T4 DNA (Takara), using ligase, the plasmid being cut by the same restriction enzymes NcoI and BamHI, thereby constructing a recombinant vector pNANe. The recombinant vector was introduced into *E. coli* BL21 (DE3) (Invitrogen) to obtain *E. coli*/pNANe.

(2) Preparation of N-Acetylneuraminic Acid Aldolase (NeuAc Aldolase)

In order to clone the nanA gene (SEQ ID NO: 28) encoding N-acetylneuraminic acid aldolase (NeuAc aldolase), the nanA gene was amplified by PCR using chromosomal DNA of the *E. coli* K-12 C600 (KCTC 1116) strain as a template and using primers of SEQ ID NO: 29 and SEQ ID NO: 30.

SEQ ID NO: 29:  5'-ggtatccatggcaacgaatttacg

SEQ ID NO: 30:  5'-ggtaggctcgagcgaggggaaac

The amplified PCR product was purified, cut by restriction enzymes NcoI and XhoI, and linked to plasmid pET32a(+)(Novagen) T4 DNA (Takara), using ligase, the plasmid being cut by the same restriction enzymes NcoI and XhoI, thereby constructing a recombinant vector pNANa. The pNANa was introduced into *E. coli* BL21(DE3)pLysS (Invitrogen) to obtain *E. coli*/pNANa.

(3) Preparation of Cytidine 5'-Monophosphate Kinase (CMK)

In order to clone the CMK gene (SEQ ID NO: 31) encoding cytidine 5'-monophosphate kinase, the CMK gene was amplified by PCR using chromosomal DNA of the *E. coli* K-12 (KCTC 1116) strain as a template and using primers of SEQ ID NO: 32 and SEQ ID NO: 33.

SEQ ID NO: 32:  5'-cat atg acg gca att gcc ccg gtt att ac

SEQ ID NO: 33:  5'-gaa ttc ggt cgc tta tgc gag agc c

The amplified PCR product was purified, cut by restriction enzymes NdeI and EcoRI, and linked to plasmid pET22b(+)(Novagen) T4 DNA (Takara), using ligase, the plasmid being cut by the same restriction enzymes NdeI and EcoRI, thereby constructing a recombinant vector pCMK. The pCMK was introduced into *E. coli* BL21(DE3)pLysS (Invitrogen) to obtain *E. coli*/pCMK.

(4) Preparation of Acetate Kinase (ACK)

In order to clone the ACK gene (SEQ ID NO: 34) encoding acetate kinase, the ACK gene was amplified by PCR using chromosomal DNA of the *E. coli* K-12 (KCTC 1116) strain as a template and using primers of SEQ ID NO: 35 and SEQ ID NO: 36.

SEQ ID NO: 35:  5'-catatgtcgagtaagttagtttctg

SEQ ID NO: 36:  5'-gaatcctcaggcagtcaggcggctcgcgtc

The amplified PCR product was purified, cut by restriction enzymes NdeI and EcoRI, and linked to plasmid pET24ma(+)(Novagen) T4 DNA (Takara), using ligase, the plasmid being cut by the same restriction enzymes NdeI and EcoRI, thereby constructing a recombinant vector pACKa. The pACKa was introduced into *E. coli* BL21(DE3) pLysS (Invitrogen) to obtain *E. coli*/pACKa.

(5) Preparation of CMP-N-Acetylneuraminic Acid Synthetase (CMP-NeuNAc Synthetase: NEU)

In order to clone the NEU gene (SEQ ID NO: 37) encoding CMP-NeuNAc synthetase (NEU), the NEU gene was amplified by PCR using chromosomal DNA of the *Neisseria meningitides* (Koram Biotech) strain as a template and using primers of SEQ ID NO: 38 and SEQ ID NO: 39.

SEQ ID NO: 38:  5'-aagcatatggaaaaacaaaatattgcg

SEQ ID NO: 39:  5'-gtggaattcttagctttccttgtg

The amplified PCR product was purified, cut by restriction enzymes NdeI and EcoRI, and linked to plasmid pET32ma(+)(Novagen) T4 DNA (Takara), using ligase, the plasmid being cut by the same restriction enzymes NdeI and EcoRI, thereby constructing a recombinant vector pSYNb. The pSYNb was introduced into *E. coli* BL21(DE3) (Invitrogen) to obtain *E. coli*/pSYNb.

500 ml of each seed obtained by culturing transformants *E. coli*/pNANe, *E. coli*/pNANa, *E. coli*/pCMK, *E. coli*/pACKa and *E. coli*/pSYNb in LB medium was inoculated in 5 l of main culture LB medium, and 4 hours later, 1-2 mM IPTG as an expression inducer was added to induce high expression of protein. When the density value of cell (OD600) was about 3 to 5, cells were harvested. The obtained cells were lysed by ultrasound or French press, and the degree of each enzyme expression was confirmed by SDS-PAGE gel. The enzymes such as cytidine 5'-monophosphate kinase (CMK), acetate kinase (ACK), NeuAc aldolase (NAN), CMP-NeuAc synthetase (NEU), and GlcNAc-2-epimerase (NANE) were precipitated by ammonium sulfate, and purified by ion exchange resin column (Protein Purification Techniques Second Edition, Oxford University Press, 2001).

Example 3

One-Pot Sialylation of Lactose Using α-2,3-Sialyltransferase

One-pot sialylation of lactose was performed by using enzyme reaction solution including α-2,3-sialyltransferase prepared in Examples 1 and 2 (PST2,3st R313N) CMK, ACK, NeuAc aldolase (NAN), CMP-NeuAc synthetase (NEU), and GlcNAc-2-epimerase (NANE) and using N-acetyl-D-glucosamine, pyruvate, and lactose as substrates.

Chemical reaction formula producing 2,3-sialyllactose or 2,6-sialyllactose from N-acetyl-D-glucosamine was shown in FIG. 1, and it shows that since the reaction is performed in a single reactor, cytidine 5'-monophosphate (CMP) which is an expensive substrate is capable of being recycled.

Reaction mixture [5~10 mM CMP (Shanghai QZU Bioscience & Biotechnology), 20~80 mM GlcNAc (Shanghai Jiubang Chemical), 40~120 mM Sodium pyruvate (ZMC Inc), 40~120 mM Lactose (DMV Inc), 20 mM MgCl$_2$.H$_2$O (Duksan), 1 mM Nucleotide triphosphate (NTP, sigma), 80~300 mM Acetyl phosphate (sigma), 50 mM Tris HCl buffer (pH 7.0), pH was maintained to be 6.5~8.0 with 37° C. 2M NaOH] was mixed with CMK, ACK, NeuAc aldolase (NAN), CMP-NeuAc synthetase (NEU) and GlcNAc-2-epimerase (NANE), and α-2,3-sialyltransferase (PST2,3st R313N), followed by stirring in a reactor to perform reaction for 5 to 12 hours.

Figure 3:
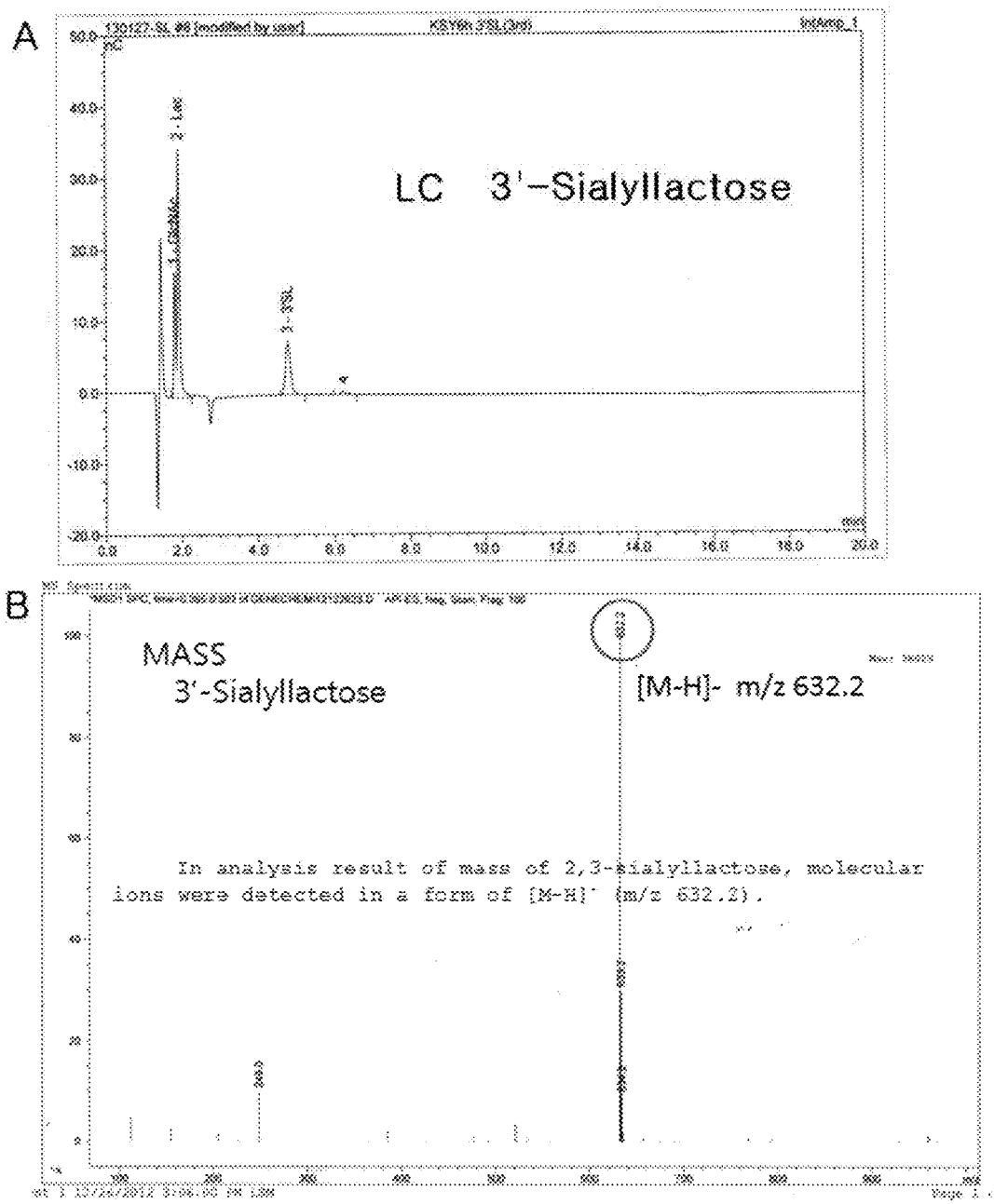
FIG. 3 shows results of 2,3-sialyllactose synthesized by one-pot reaction of the present invention, confirmed by LC (FIG. 3A) and Mass (FIG. 3B).

As analysis results of LC and Mass, it could be confirmed that α-2,3-sialyllactose was synthesized (FIG. 3). In LC, Dionex DX-500 Chromatography system was used, and conditions were as follows:
Column: CarboPac PA100 Analytical Column(P/N 043055) with guard (P/N 043054)
Flow: 1 ml/min
Run time: 20 min
Injection volume: 25 μl
Detection: ED40 Electrochemical Detector (gold electrode)
Eluent: 100 mM NaOH/100 mM NaOAc.

In analysis result of mass of 2,3-sialyllactose, molecular ions were detected in a form of [M-H]$^-$ (m/z 632.2).

Figure 4:
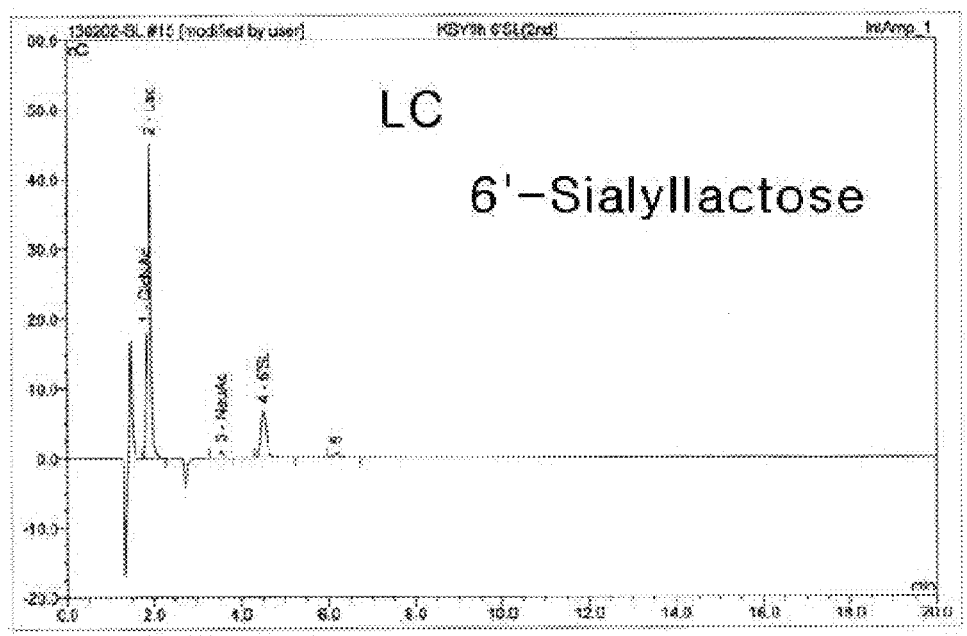
FIG. 4 shows results of 2,6-sialyllactose synthesized by one-pot reaction of the present invention, confirmed by LC (FIG. 4A) and Mass (FIG. 4B).
Figure 4:
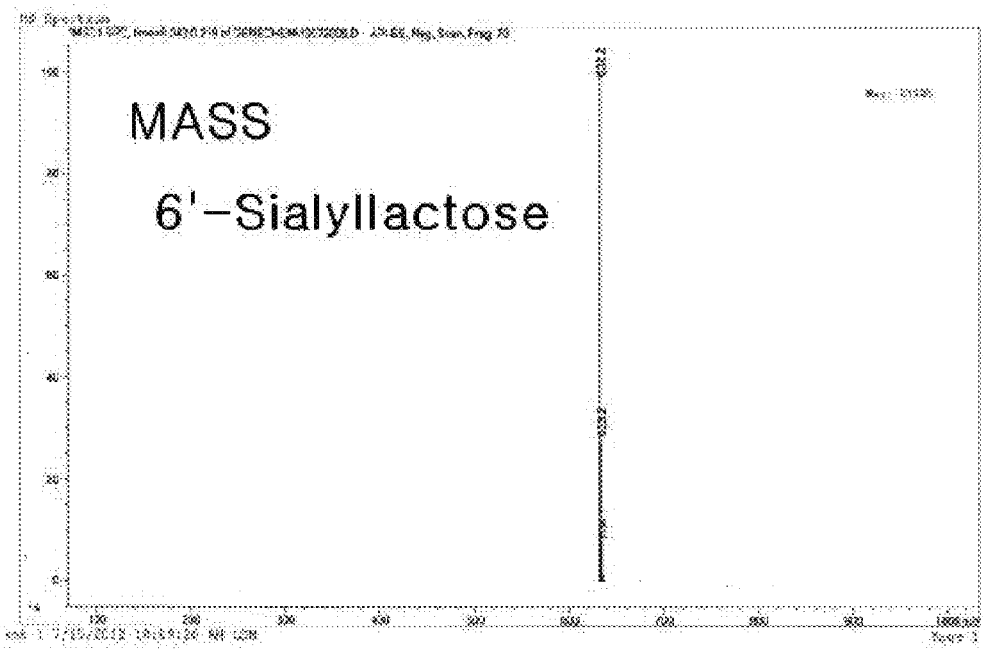

2,6-sialyllactose was synthesized by the same method as 2,3-sialyllactose except for adding α-2,6-sialyltransferase (2,6STN L433S) instead of using α-2,3-sialyltransferase (FIG. 4).

Example 4

Comparison Between One-Pot Sialylation of Lactose and the Conventional Method

Production amount of sialyllactose obtained by a method for preparing sialyllactose using substrate concentrations of Table 4 by the same one-pot method as Example 3 and production amount of sialyllactose obtained by the conventional method for preparing sialyllactose by the conventional two-pot method were compared.

In the conventional two-pot method, reaction mixture [50 mM CMP, 100 mM GlcNAc, 100 mM Sodium pyruvate, 20 mM MgCl$_2$.H$_2$O, 1 mM Nucleotide triphosphate (NTP), 300 mM Acetyl phosphate, 50 mM Tris HCl buffer (pH 7.0) 7 l, pH was maintained to be 6.5~8.0 with 37° C. 2M NaOH] was mixed with CMK, ACK, NeuAc aldolase (NAN), CMP-NeuAc synthetase (NEU) and GlcNAc-2-epimerase (NANE) prepared by Example 2, followed by stirring in a reactor to perform reaction for 5 to 12 hours, thereby synthesizing CMP-N-acetylneuraminic acid.

100 mM lactose was added to about 40 mM CMP-N-acetylneuraminic acid as synthesized above in 50 mM Tris HCl (Ph 7.5) buffer, and α-2,3-sialyltransferase was added thereto, thereby preparing sialyllactose. Then, as compared to a standard curve of standard sialyllactose (Sigma), an amount of sialyllactose was measured by LC.

TABLE 4

| difference between the present invention and conventional method | | conventional method (Two step) | the present invention using sialyltransferase (One step) |
|---|---|---|---|
| Main substrate for Synthesis | CMP | 50 mM | 10 mM |
| | N-acetyl-D-glucosamine | 100 mM | 80 mM |
| | pyruvate | 100 mM | 80 mM |
| | Acetyl phosphate | 300 mM | 200 mM |
| | lactose | 100 mM | 80 mM |
| production amount of sialyllactose | | 20 g/L | 40 g/L |

As a result, as shown in Table 4, according to the method for preparing sialyllactose by one-pot reaction of the present invention, it was confirmed that the production amount of sialyllactose was increased by twice as much even though the concentration of CMP decreased to be 1/5.

Example 5

One-Pot Sialylation of Galactose

Figure 5:
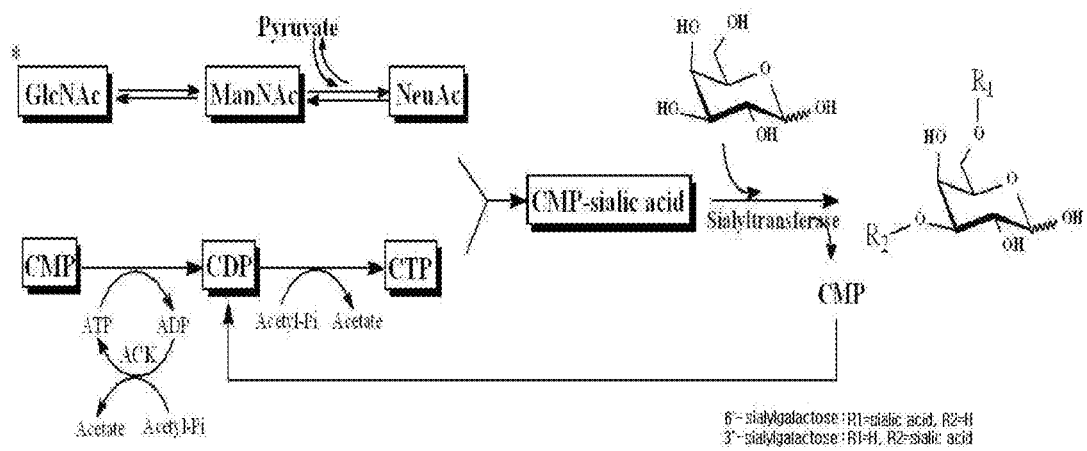
FIG. 5 shows a synthesis process for preparing sialyl galactose by one-pot reaction of the present invention.

Sialylation of galactose (Sigma) which is monosaccharide was performed, and the sialylation was shown in FIG. 5.

Reaction mixture [5~10 mM CMP, 20~80 mM GlcNAc, 40~120 mM Sodium pyruvate, 40~120 mM Taxol galactose derivative, 20 mM MgCl$_2$.H$_2$O, 1 mM Nucleotide triphosphate (NTP), 80~300 mM Acetyl phosphate, 50 mM Tris HCl buffer (pH 7.0), pH was maintained to be 6.5~8.0 with 37° C. 2M NaOH] was mixed with CMK, ACK, NeuAc aldolase (NAN), CMP-NeuAc synthetase (NEU) and GlcNAc-2-epimerase (NANE), and α-2,3-sialyltransferase (PST2,3st R313N), followed by stirring in a reactor to perform reaction for 5 to 12 hours.

Figure 6:
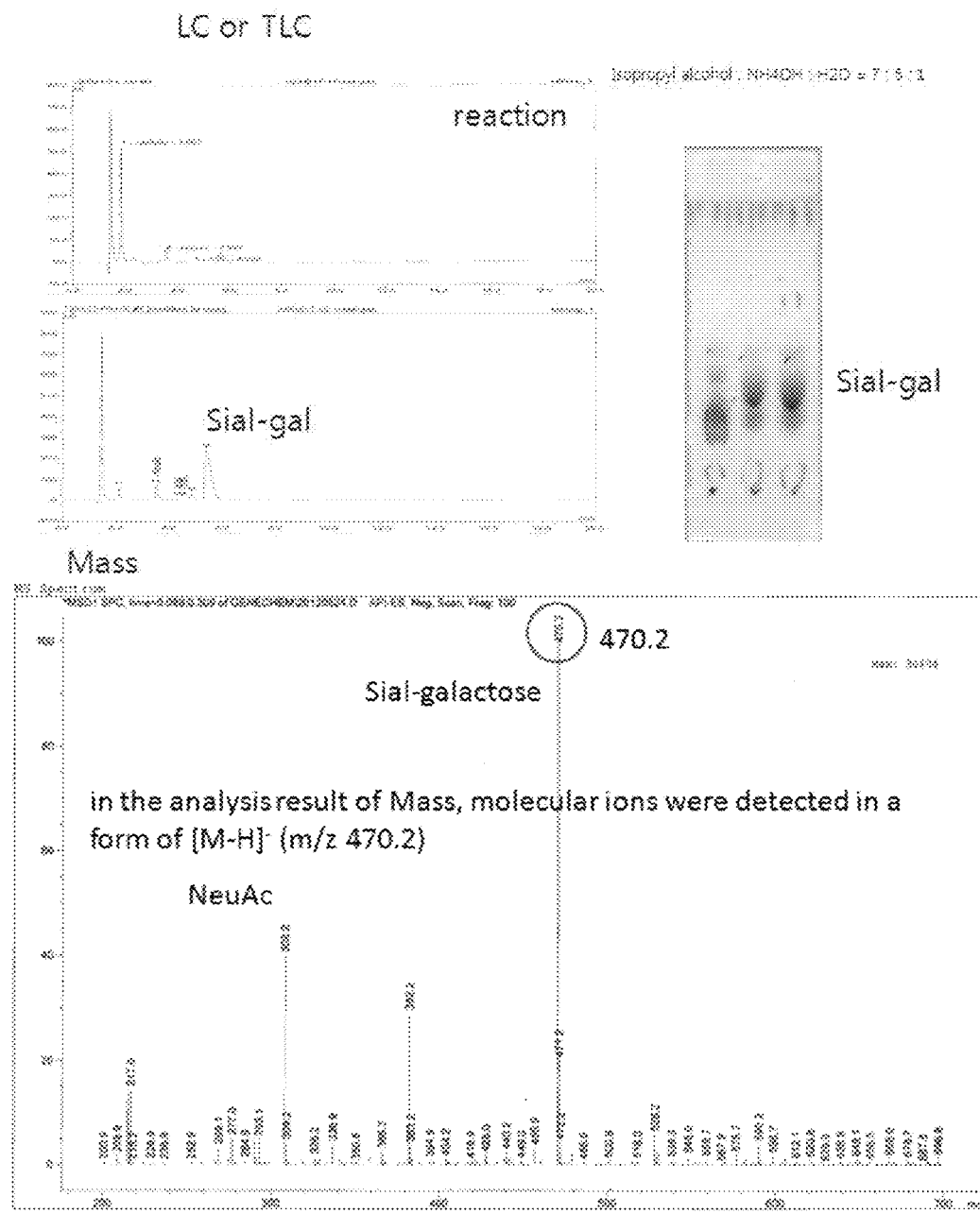
FIG. 6 shows results of sialyl galactose synthesized by one-pot reaction of the present invention, confirmed by TLC (FIG. 5A) and Mass (FIG. 5B).

As analysis result of LC, Mass and TLC, it was confirmed that sialyl galactose was synthesized, and in the analysis result of Mass, molecular ions were detected in a form of [M-H]$^-$ (m/z 470.2) (FIG. 6).

Example 6

Preparation of Sialic Acid Derivative of Linker

Figure 7:
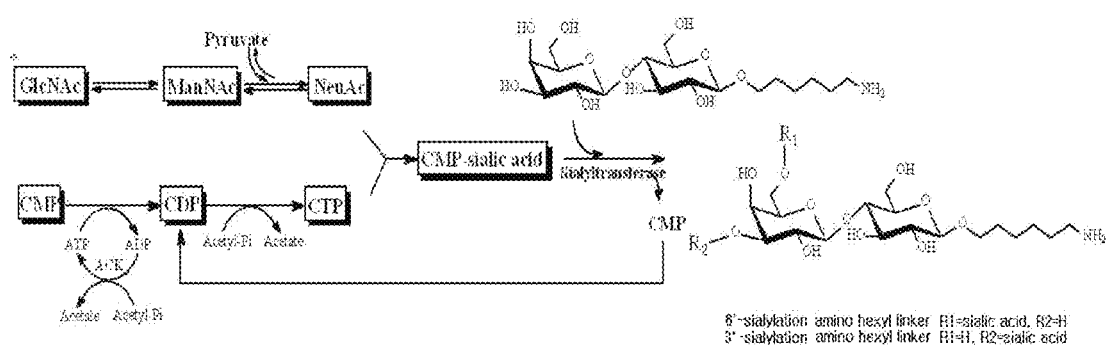
FIG. 7 shows a synthesis process of a sialic acid derivative of a linker coupled with lactose.

Sialylation of aminohexyl linker including galactose as terminal residue was performed, and the sialylation was shown in FIG. 7.

Reaction mixture [5~10 mM CMP, 20~80 mM GlcNAc, 40~120 mM Sodium pyruvate, 40~120 mM aminohexyl linker at terminal of galactose, 20 mM MgCl$_2$.H$_2$O, 1 mM Nucleotide triphosphate (NTP), 80~300 mM Acetyl phosphate, 50 mM Tris HCl buffer (pH 7.0), pH was maintained to be 6.5~8.0 with 37° C. 2M NaOH] was mixed with CMK, ACK, NeuAc aldolase (NAN), CMP-NeuAc synthetase (NEU) and GlcNAc-2-epimerase (NANE), and α-2,3-sialyltransferase, respectively, followed by stirring in a reactor to perform reaction for 5 to 12 hours.

Figure 8:
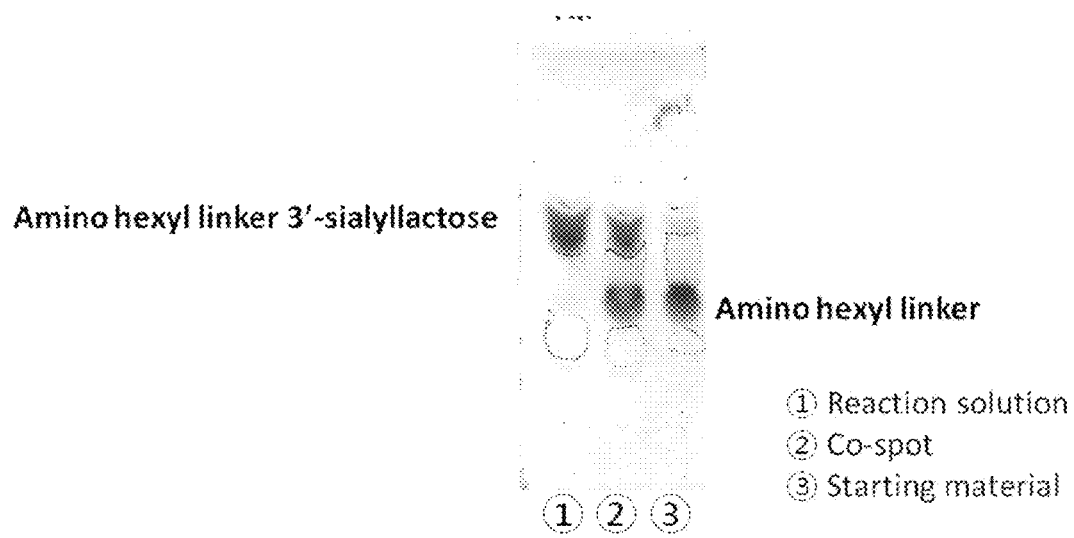
FIG. 8 shows results of aminohexyl linker 2,3-sialyllactose of a linker combined with lactose synthesized by one-pot reaction of the present invention, confirmed by TLC and Mass.
Figure 8:
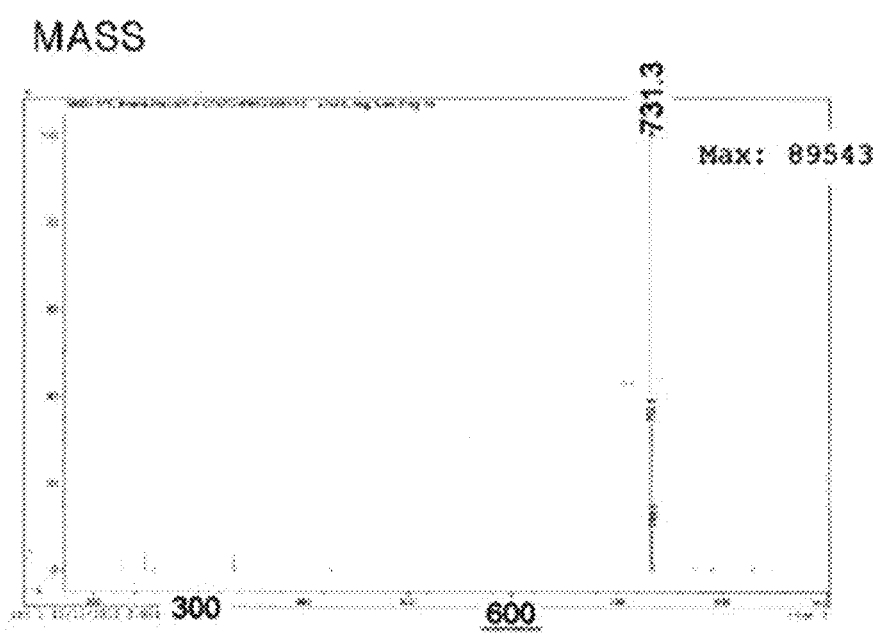

As analysis result of TLC and Mass, it was confirmed that 2,3-sialyllactose-linker was synthesized, and in analysis result of Mass, molecular ions were detected in a form of [M-H]$^-$ (m/z 731.3) (FIG. 8).

Example 7

Preparation of Sialic Acid Derivative of Flavonoid

Figure 9:
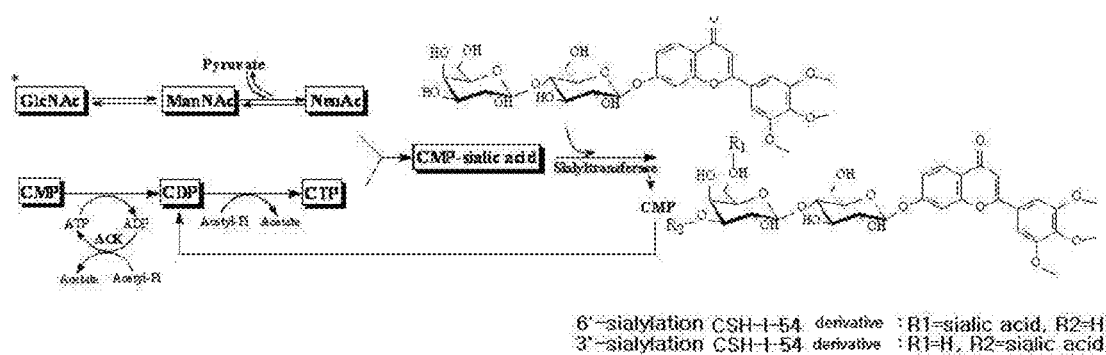
FIG. 9 shows a synthesis process of a sialic acid derivative of a derivative including galactose residue of flavonoid CSH-I-54.

Sialylation of lactose derivative of flavonoid CSH-I-54 having a structure of Chemical Formula 1 was performed, and the sialylation was shown in FIG. 9.

[Chemical Formula 1]

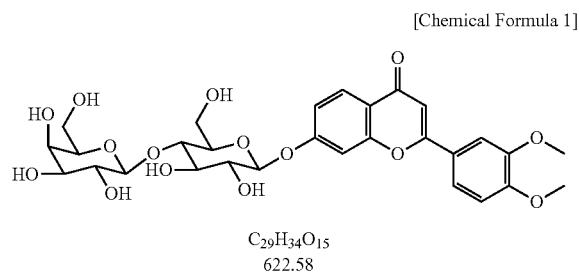 [SMILES: COc1ccc(-c2cc(=O)c3ccc(OC4OC(CO)C(OC5OC(CO)C(O)C(O)C5O)C(O)C4O)cc3o2)cc1OC]

C$_{29}$H$_{34}$O$_{15}$
622.58

Reaction mixture [5~10 mM CMP, 20~80 mM GlcNAc, 40~120 mM Sodium pyruvate, 40~120 mM lactose derivative of flavonoid CSH-I-54, 20 mM MgCl$_2$.H$_2$O, 1 mM Nucleotide triphosphate (NTP), 80~300 mM Acetyl phosphate, 50 mM Tris HCl buffer (pH 7.0), pH was maintained to be 6.5~8.0 with 37° C. 2M NaOH] was mixed with CMK, ACK, NeuAc aldolase (NAN), CMP-NeuAc synthetase (NEU) and GlcNAc-2-epimerase (NANE), and α-2,3-sialyltransferase, respectively, followed by stirring in a reactor to perform reaction for 5 to 12 hours.

Synthesis of 2,3-sialyllactose-CSH-I-54 was confirmed by LC and Mass, and LC analysis conditions were as follows:

Column: Thermo ODS Hypersil (250*4.6 mm)
Detection: UV 340 nm
Temp.: R.T
Flow rate: 1 mL/min
Inj. Volume: 20 μl
Mobile phase: A buffer: 0.1 M TEAA
B buffer: CH$_3$CN
Initial: B conc. 0%

| | |
|---|---|
| 15 min | 70% |
| 20 min | 100% |
| 22 min | 100% |
| 25 min | 0% |
| 30 min | 0%. |

Figure 10:
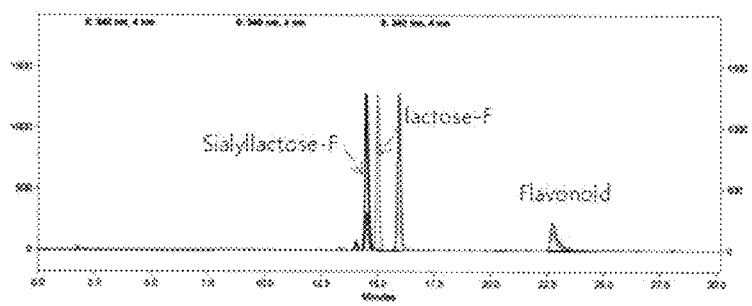
FIG. 10 shows results of 2,3-sialyllactose-CSH-I-54 synthesized by one-pot reaction of the present invention, confirmed by LC and Mass.
Figure 10:
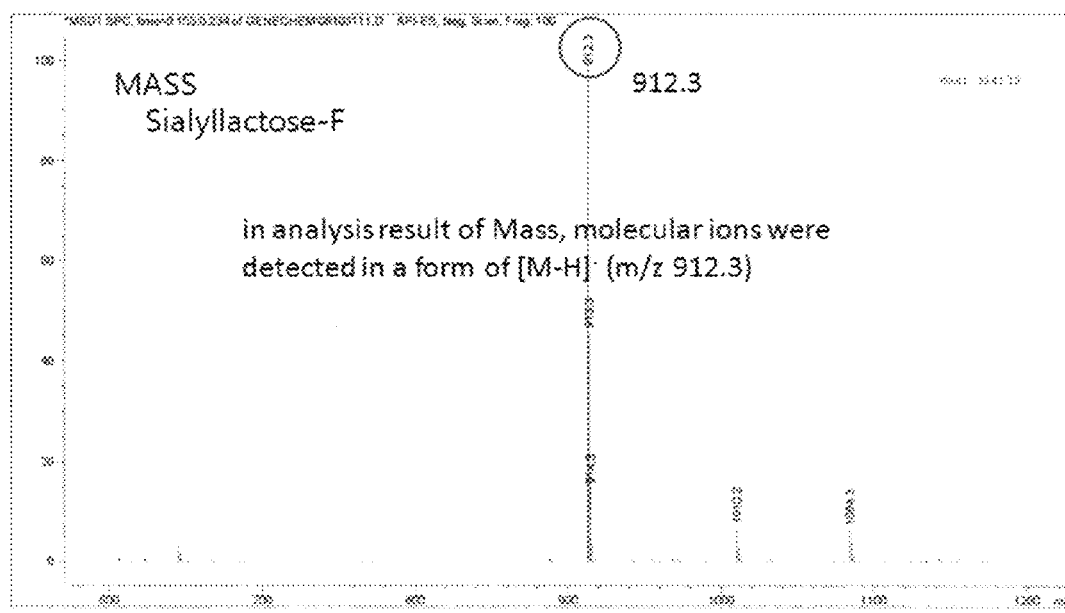

As analysis result of LC and Mass, it was confirmed that 2,3-sialyllactose-CSH-I-54 was synthesized, and in analysis result of Mass, molecular ions were detected in a form of [M-H]$^-$ (m/z 912.3) (FIG. 10).

Example 8

Preparation of Sialic Acid Derivative of Tacrolimus

Figure 11:
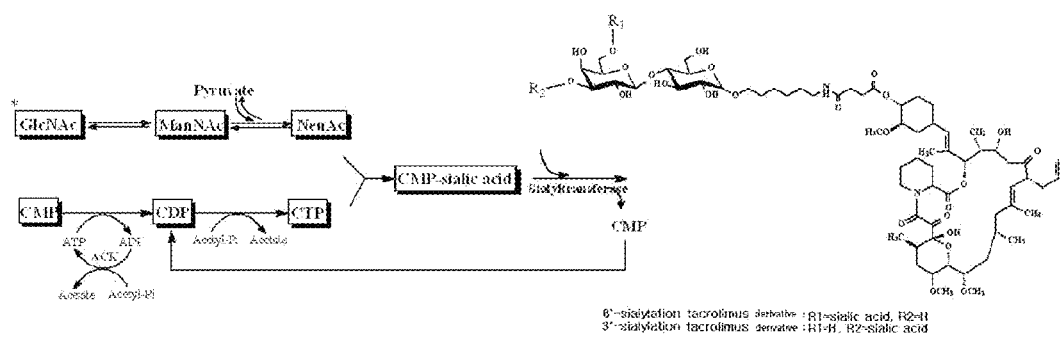
FIG. 11 shows a synthesis process of a sialic acid derivative of a galactose derivative of immunosuppressant, tacrolimus.

Sialylation of galactose derivative of immunosuppressant Tacrolimus having a structure of Chemical Formula 2 and galactose derivative of immunosuppressant Tacrolimus having a linker having a structure of Chemical Formula 3 was performed, and the sialylation was shown in FIG. 11.

Galactose Derivative of Tacrolimus

[Chemical Formula 2]

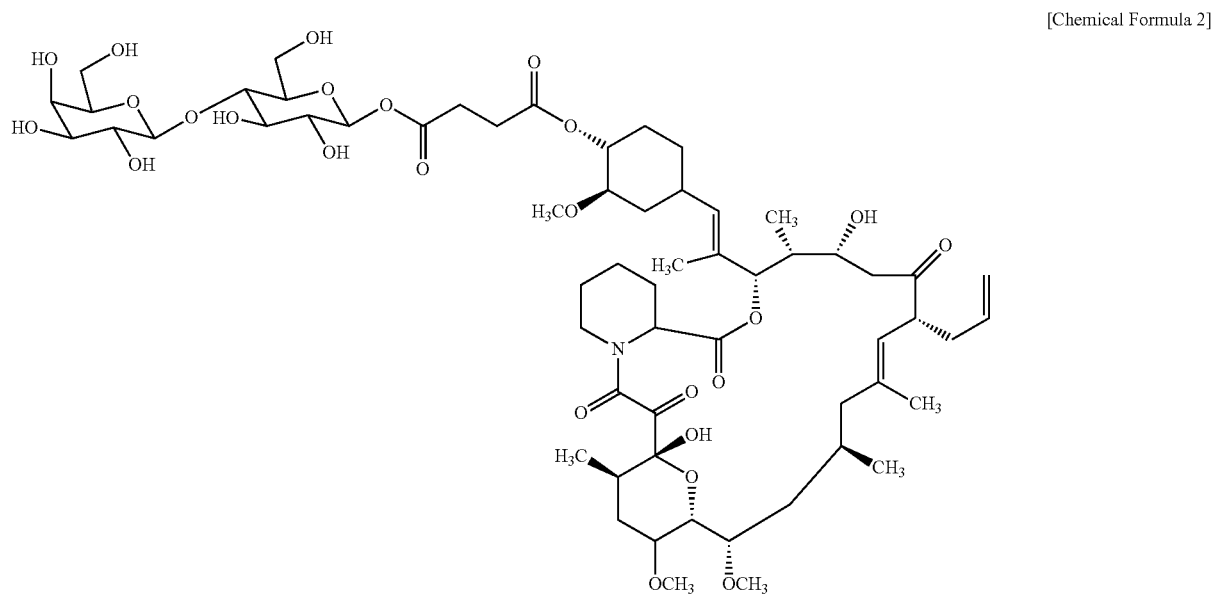

[Chemical Formula 3]

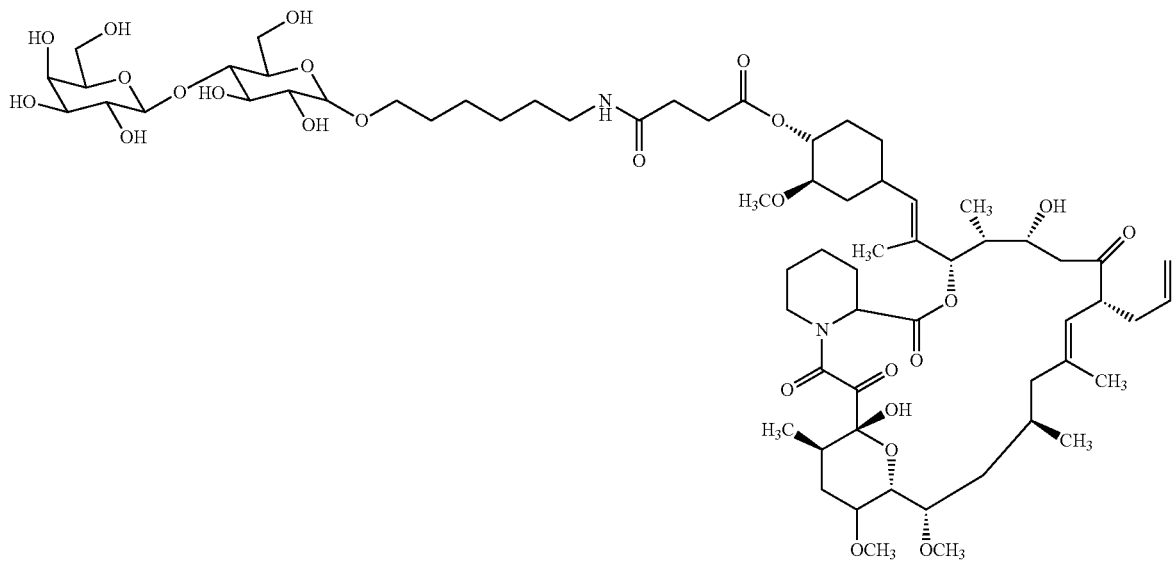

Reaction mixture [5~10 mM CMP, 20~80 mM GlcNAc, 40~120 mM Sodium pyruvate, 40~120 mM Tacrolimus galactose derivative, 20 mM MgCl$_2$.H$_2$O, 1 mM Nucleotide triphosphate (NTP), 80~300 mM Acetyl phosphate, 50 mM Tris HCl buffer (pH 7.0), pH was maintained to be 6.5~8.0 with 37° C. 2M NaOH] was mixed with CMK, ACK, NeuAc aldolase (NA), CMP-NeuAc synthetase (NEU) and Glc-NAc-2-epimerase (NANE), and α-2,3-sialyltransferase, respectively, followed by stirring in a reactor to perform reaction for 5 to 12 hours.

Synthesis of 2,3-sialyllactose-Tacrolimus was confirmed by LC and Mass, and LC analysis conditions were as follows (FIG. 12):

Column: Thermo ODS Hypersil (250*4.6 mm)

Detection: UV 225 nm

Temp.: 55° C.

Flow rate: 1 mL/min

Inj. Volume: 20 μl

Mobile phase: A buffer: H$_2$O

B buffer: CH$_3$CN

Initial: B conc. 30%

| | |
|---|---|
| 5 min | 30% |
| 35 min | 80% |
| 36 min | 80% |
| 38 min | 100% |
| 45 min | 100% |
| 46 min | 30% |
| 50 min | 30% |

Figure 12A:
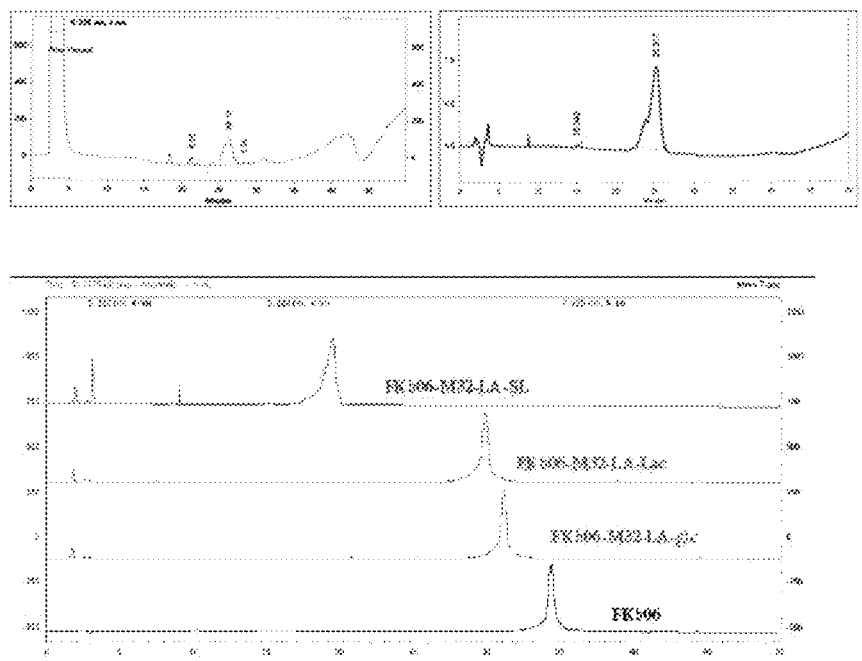
FIG. 12 shows results of 2,3-sialyllactose-tacrolimus synthesized by one-pot reaction of the present invention, confirmed by LC (FIG. 12a) and Mass (FIG. 12b).
Figure 12B:
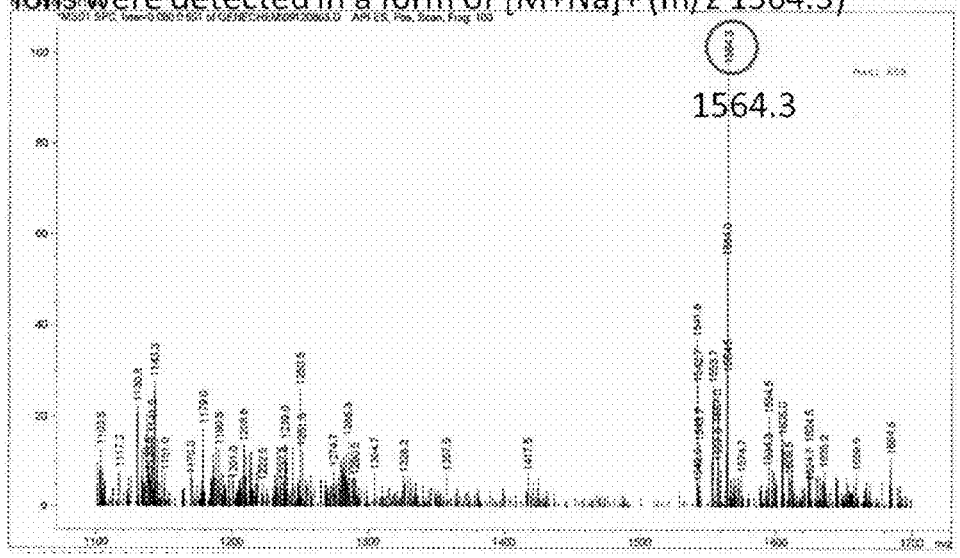

As analysis result of Mass, in galactose-Tacrolimus having a structure of Chemical Formula 2, molecular ions were detected in a form of [M+Na]$^+$ (m/z 1564.3), and in 2,3-sialyllactose-Tacrolimus having Aminohexyl linker in Chemical Formula 3, molecular ions were detected in a form of [M-2H]$^{2-}$ (m/z 1616.8) (FIG. 12).

Example 9

Preparation of Sialic Acid Derivative of Anti-Cancer Agent Taxol

Figure 13:
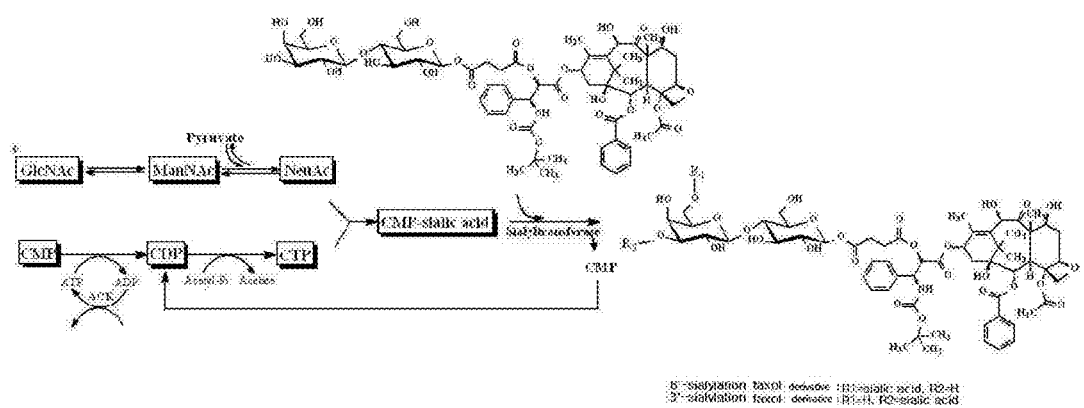
FIG. 13 shows a synthesis process of a sialic acid derivative of a galactose derivative of anti-cancer agent, Taxol.

Sialylation of galactose derivative of immunosuppressant Taxol having a structure of Chemical Formula 4 was performed, and the sialylation was shown in FIG. 13.

Galactose Derivative of Taxol

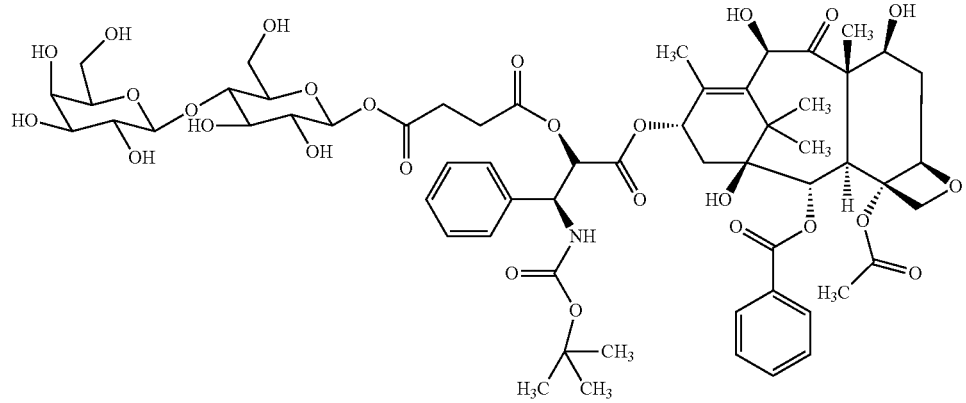

[Chemical Formula 4]

Reaction mixture [5~10 mM CMP, 20~80 mM GlcNAc, 40~120 mM Sodium pyruvate, 40~120 mM Taxol galactose derivative, 20 mM $MgCl_2.H_2O$, 1 mM Nucleotide triphosphate (NTP), 80~300 mM Acetyl phosphate, 50 mM Tris HCl buffer (pH 7.0), pH was maintained to be 6.5~8.0 with 37° C. 2M NaOH] was mixed with CMK, ACK, NeuAc aldolase (NAN), CMP-NeuAc synthetase (NEU) and GlcNAc-2-epimerase (NANE), and α-2,3-sialyltransferase, respectively, followed by stirring in a reactor to perform reaction for 5 to 12 hours.

Synthesis of 2,3-sialyllactose-taxol was confirmed by LC and Mass, and LC analysis conditions were as follows (FIG. 14):

Column: Thermo ODS Hypersil (4.6*250 mm)
Detection: UV 260 nm
Temp.: R.T
Flow rate: 1 mL/min
Inj. Volume: 20 μl
Mobile phase: A buffer: 0.1 M TEAA
B buffer: $CH_3CN$
Initial: B conc. 35%

| | |
|---|---|
| 30 min | 65% |
| 33 min | 65% |
| 35 min | 35% |
| 38 min | 35% |

Figure 14A:
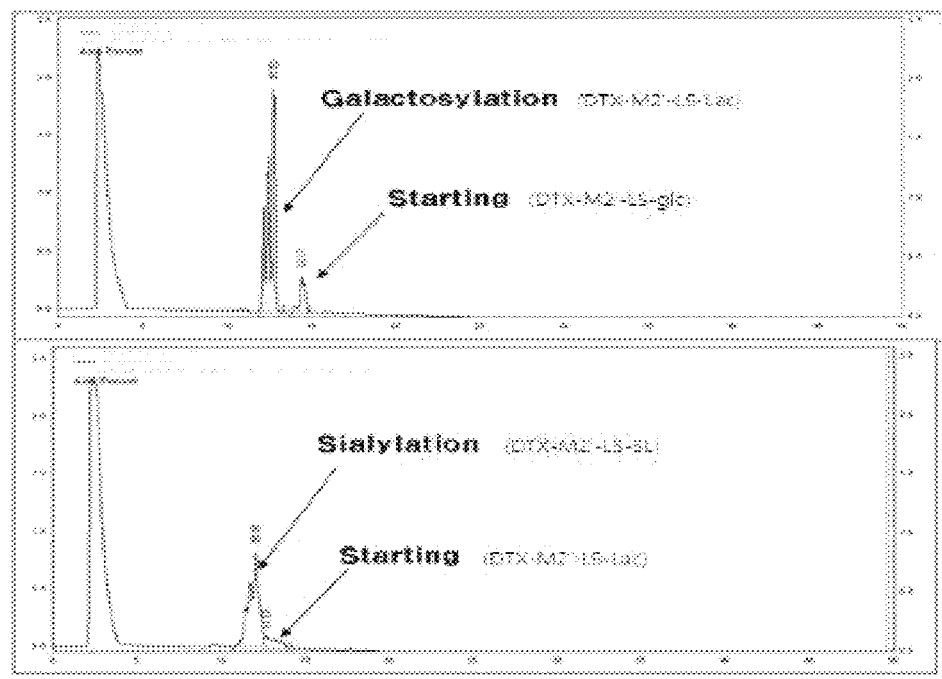
FIG. 14 shows results of 2,3-sialyllactose-taxol synthesized by one-pot reaction of the present invention, confirmed by LC (FIG. 14a) and Mass (FIG. 14b).
Figure 14B:
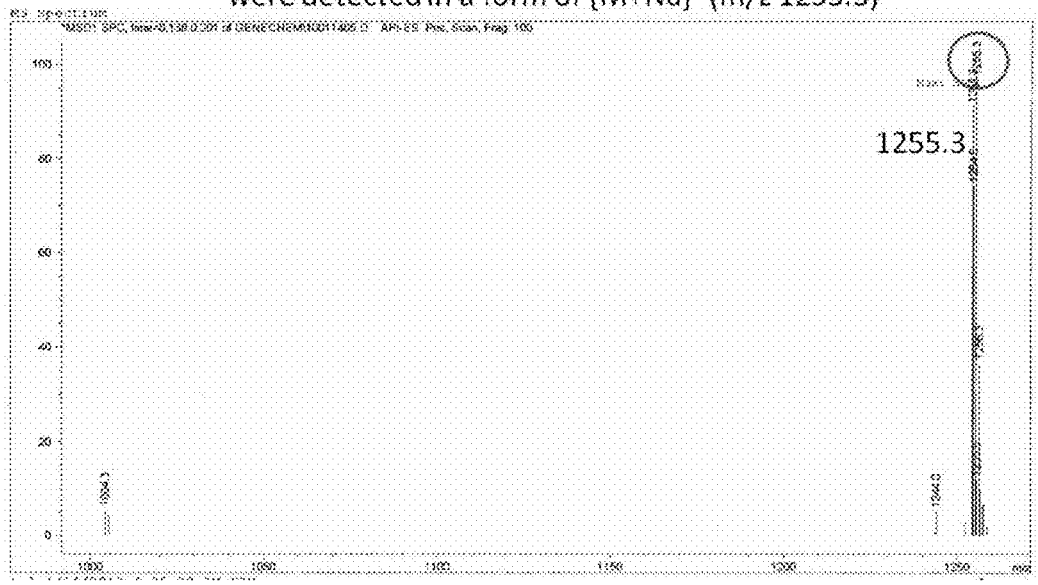
Figure 14B:
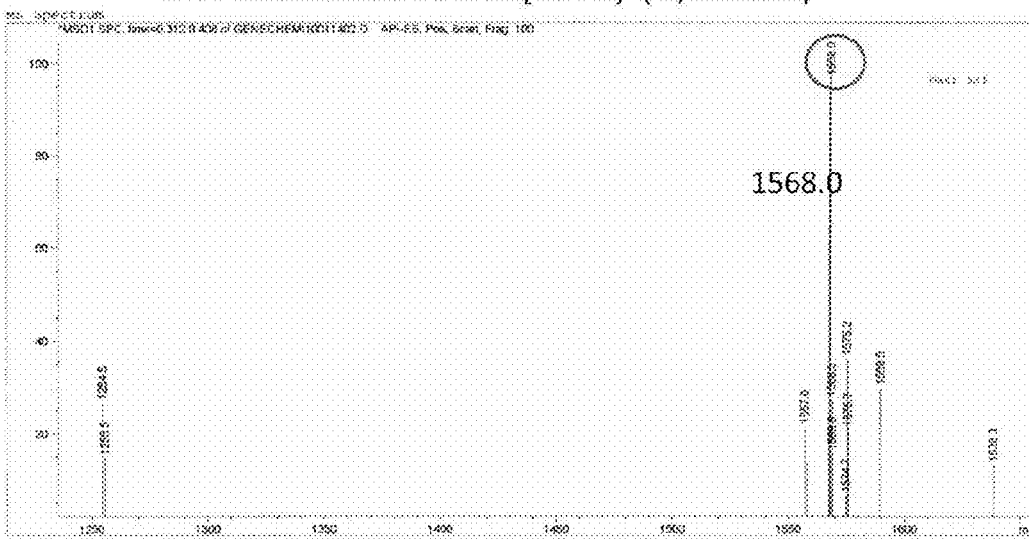

As analysis result of Mass, in galactose-taxol, molecular ions were detected in a form of $[M+Na]^+$ (m/z 1255.3), and in 2,3-sialyllactose-taxol, molecular ions were detected in a form of $[M+Na]^+$ (m/z 1568.0) (FIG. 14).

Example 10

Preparation of Sialic Acid Derivative of Antibiotic Vancomycin

Figure 15:
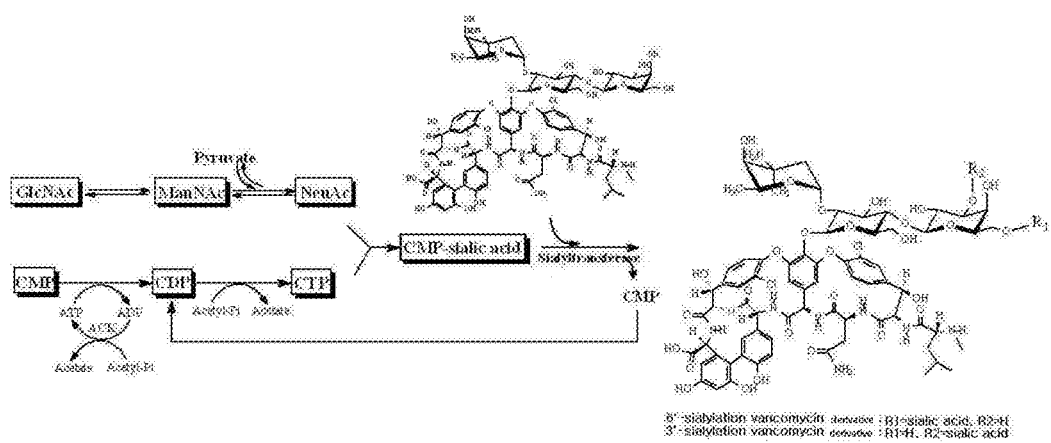
FIG. 15 shows a synthesis process of a sialic acid derivative of a galactose derivative of antibiotic, Vancomycin.

Sialylation of galactose derivative of antibiotic Vancomycin having a structure of Chemical Formula 5 was performed, and the sialylation was shown in FIG. 15.

Galactose Derivative of Vancomycin

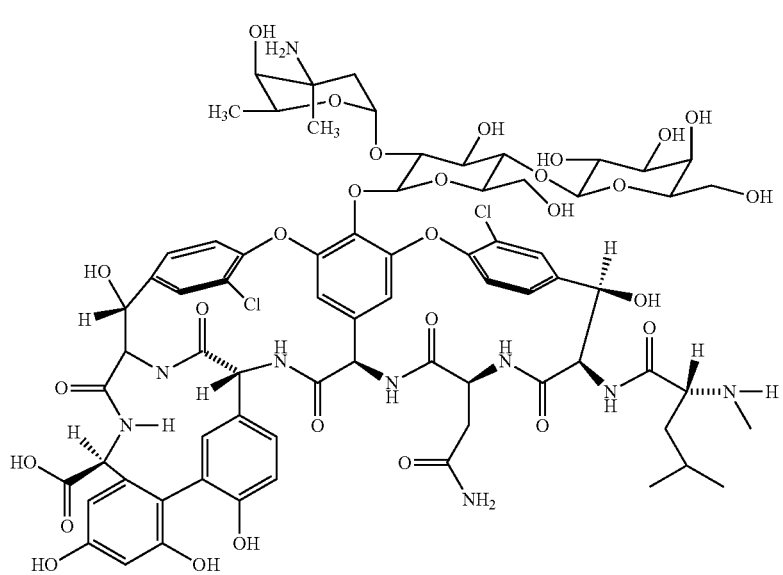

[Chemical Formula 5]

Reaction mixture [5~10 mM CMP, 20~80 mM GlcNAc, 40~120 mM Sodium pyruvate, 40~120 mM Vancomycin galactose derivative, 20 mM MgCl$_2$.H$_2$O, 1 mM Nucleotide triphosphate (NTP), 80~300 mM Acetyl phosphate, 50 mM Tris HCl buffer (pH 7.0), pH was maintained to be 6.5~8.0 with 37° C. 2M NaOH] was mixed with CMK, ACK, NeuAc aldolase (NAN), CMP-NeuAc synthetase (NEU) and Glc-NAc-2-epimerase (NANE), and α-2,3-sialyltransferase, respectively, followed by stirring in a reactor to perform reaction for 5 to 12 hours.

Figure 16A:
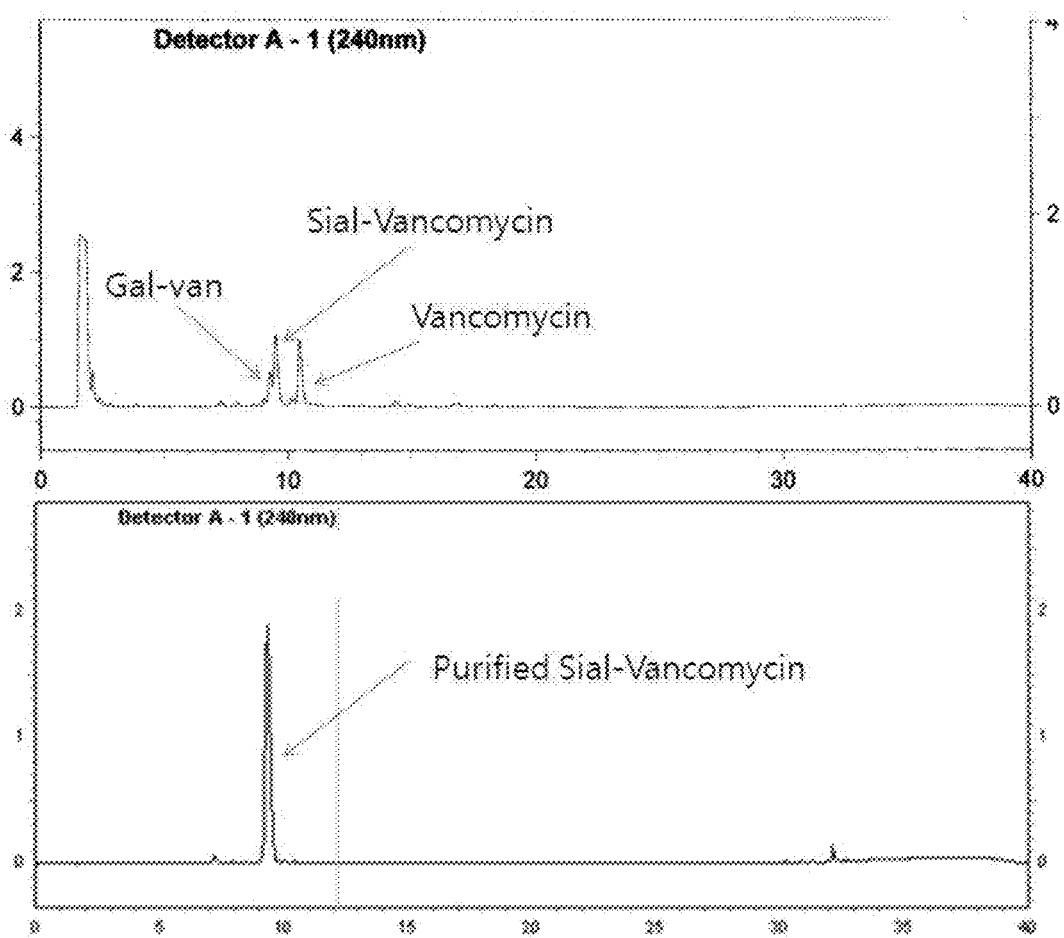
FIG. 16a shows result of 2,3-sialyllactose-vancomycin synthesized by one-pot reaction of the present invention, confirmed by LC.

Synthesis of 2,3-sialyllactose-vancomycin was confirmed by LC and Mass, and LC analysis conditions were as follows (FIG. 16a):

Column: Chromollth performance RP-18e, 4.6×100 mm
Detection: UV 260 nm
Temp.: R.T
Flow rate: 1 mL/min
Inj. Volume: 20 μl
Mobile phase: A buffer: H2O
B buffer: CH$_3$CN
Initial: B conc. 5%

| | |
|---|---|
| 3 min | 10% |
| 20 min | 20% |
| 25 min | 30% |
| 30 min | 80% |
| 35 min | 80% |
| 37 min | 5% |
| 40 min | 5% |

Figure 16B:
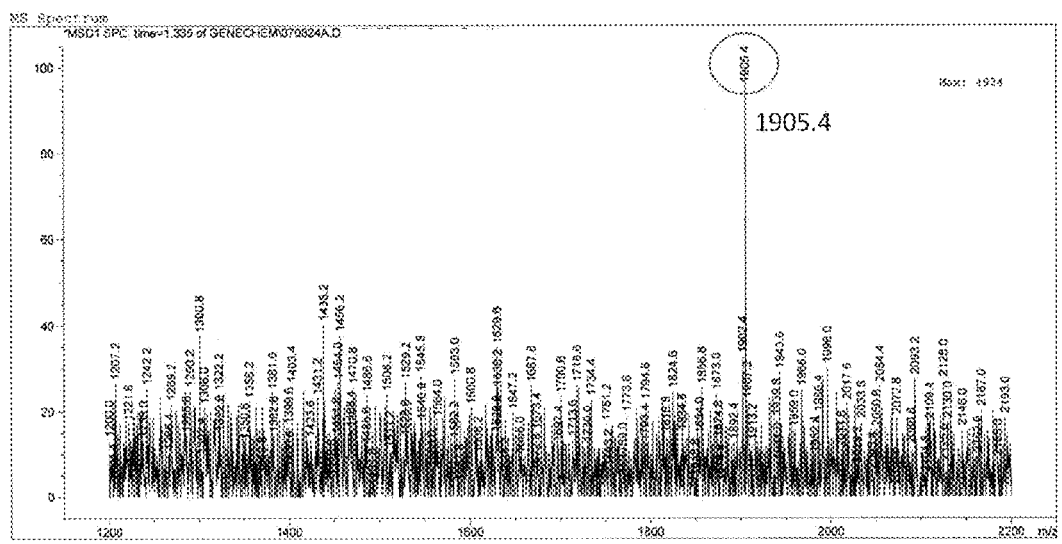
FIG. 16b shows result of 2,3-sialyllactose-vancomycin synthesized by one-pot reaction of the present invention, confirmed by Mass.

As the analysis result of Mass, in 2,3-sialyllactose-vancomycin, molecular ions were detected in a form of [M+4H]$^+$ (m/z 1905.4) (FIG. 16b).

INDUSTRIAL APPLICABILITY

According to the method for preparing a sialic acid derivative of the present invention, expensive cytidine 5'-monophosphate (CMP) is capable of being recycled in a reactor, such that an amount of the CMP introduced into the reactor may be reduced, and the sialic acid derivative is capable of being prepared at a significantly high efficiency by using cheap N-acetyl-D-glucosamine (GlcNAc), pyruvate as substrates.

Although specific embodiments of the present invention are described in detail, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

The invention claimed is:

1. A method for preparing a sialic acid derivative comprising: (a) preparing a sialic acid derivative of a compound including sialyllactose or galactose residues by adding a compound including cytidine 5'-monophosphate (CMP), acetyl phosphate, nucleotide triphosphate (NTP), N-acetyl-D-glucosamine (GlcNAc), Sodium pyruvate, and lactose or galactose residues as substrates, and reacting a reaction solution including cytidine 5'-monophosphate kinase (CMK), acetate kinase (ACK), CMP-N-acetylneuraminic acid synthetase (CMP-NeuAc synthetase: NEU), N-acetylglucosamine-2-epimerase (GlcNAc-2-epimerase: NANE), N-acetylneuraminic acid aldolase (NeuAc aldolase, NAN) and α-2,3-sialyltransferase mutant having an amino acid sequence represented by one selected from the group consisting of SEQ ID NOs: 2-6, or α-2,6-sialyltransferase mutant comprising T substitution from I in 411$^{th}$ amino acid of α-2,6-sialyltransferase having amino acid sequence of SEQ ID NO:13, or S or T substitution from L in 433$^{th}$ amino acid of α-2,6-sialyltransferase having amino acid sequence of SEQ ID NO:13, in a single reactor; and (b) obtaining the prepared sialic acid derivative of the compound including sialyllactose or galactose residues prepared according to the step (a).

2. The method according to claim 1, wherein the α-2,6-sialyltransferase has an amino acid sequence represented by one selected from the group consisting of SEQ ID NOs: 14-18.

3. The method according to claim 1, wherein the reaction is performed at a temperature of 25° C. to 38° C.

4. The method according to claim 1, wherein pH of the reaction solution is 7 to 9.

5. The method according to claim 1, wherein the N-acetyl-glucosamine-2-epimerase (GlcNAc-2-epimerase: NANE) has an amino acid sequence represented by SEQ ID NO: 25.

6. The method according to claim 1, wherein the compound including galactose residues is a galactose derivative of a compound selected from the group consisting of monosaccharides, oligosaccharides, linkers, flavonoids, anti-cancer agents, antibiotics, immunosuppressants and antibodies.

* * * * *

UNITED STATES PATENT AND TRADEMARK OFFICE
CERTIFICATE OF CORRECTION

PATENT NO. : 9,637,768 B2  
APPLICATION NO. : 14/894757  
DATED : May 2, 2017  
INVENTOR(S) : Jin Suk Woo et al.

Page 1 of 1

It is certified that error appears in the above-identified patent and that said Letters Patent is hereby corrected as shown below:

In the Specification

Column 4, Line 28: "BEST MODEL" should be --BEST MODE--.

Column 11, Line 26: "1411T exhibited" should be --I411T exhibited--.

Column 21, Lines 33-34: "NeuAc aldolase (NA)," should be --NeuAc aldolase (NAN),--.

Signed and Sealed this  
Sixth Day of June, 2017

Michelle K. Lee  
*Director of the United States Patent and Trademark Office*